US007358066B2

(12) United States Patent
Thill et al.

(10) Patent No.: US 7,358,066 B2
(45) Date of Patent: Apr. 15, 2008

(54) VARIANTS AND EXONS OF THE GLYT1 TRANSPORTER

(75) Inventors: Gilbert Thill, Bois Colombes (FR); Philippe Jais, Issy-les-Moylineaux (FR); Pascale Grel, Viry-Chatillon (FR); Sandrine Mace, Jouy-en-Josas (FR)

(73) Assignee: Serono Genetics Institute S.A., Evry (FR)

( * ) Notice: Subject to any disclaimer, the term of this patent is extended or adjusted under 35 U.S.C. 154(b) by 375 days.

(21) Appl. No.: 10/484,690

(22) PCT Filed: Jul. 22, 2002

(86) PCT No.: PCT/IB02/03386

§ 371 (c)(1),
(2), (4) Date: Sep. 27, 2004

(87) PCT Pub. No.: WO03/010196

PCT Pub. Date: Feb. 6, 2003

(65) Prior Publication Data

US 2005/0089855 A1 Apr. 28, 2005

Related U.S. Application Data

(60) Provisional application No. 60/307,685, filed on Jul. 24, 2001.

(51) Int. Cl.
| C12P 21/06 | (2006.01) |
| C12N 15/00 | (2006.01) |
| C12N 5/00 | (2006.01) |
| C12N 1/00 | (2006.01) |
| C12N 1/20 | (2006.01) |
| C07H 21/02 | (2006.01) |
| C07H 21/04 | (2006.01) |
| C07K 1/00 | (2006.01) |

(52) U.S. Cl. .................. 435/69.1; 435/320.1; 435/325; 435/243; 435/252.3; 536/23.1; 536/23.5; 530/350

(58) Field of Classification Search ...................... None
See application file for complete search history.

(56) References Cited

U.S. PATENT DOCUMENTS 5,968,823 A * 10/1999 Borden et al. .............. 435/349

FOREIGN PATENT DOCUMENTS

| EP | 0572287 A2 | 1/1993 |
| WO | WO 94/23026 | 10/1994 |
| WO | WO 97/45423 | 12/1997 |
| WO | WO 98/18522 | 5/1998 |

OTHER PUBLICATIONS

Barker, G.A. et al. "Neutral Amino Acid Transport in Bovine Articular Chondrocytes", *Journal of Physiology*, 1999, pp. 795-808, vol. 514.3.
Bergeron, R. et al. "Modulation of N-methyl-$_D$-aspartate Receptor Function by Glycine Transport", *Proc. Natl. Acad. Sci. USA*, Dec. 1998, pp. 15730-15734, vol. 95.
Clark, J. et al. "Amino Acid Neurotransmitter Transporters: Structure, Function, and Molecular Diversity", *BioEssays*, May 1993, pp. 323-332, vol. 15, No. 5.
Evans, J. et al. "Cloning, Functional Characterisation and Population Analysis of a Variant Form of the Human Glycine Type 2 Transporter", *FEBS Letters*, 1999, pp. 301-306, vol. 463.
Green, P. et al. "The Role of Antisense RNA in Gene Regulation", *Ann. Rev. Biochem.*, 1986, pp. 569-597, vol. 55.
Horiuchi, M. et al. "Surface-localized Glycine Transporters 1 and 2 Function as Monomeric Proteins in *Xenopus oocytes*", *PNAS*, Feb. 13, 2001, pp. 1448-1453, vol. 98, No. 4.
Izant, J. et al. "Inhibition of Thymidine Kinase Gene Expression by Anti-Sense RNA: A Molecular Approach to Genetic Analysis", *Cell*, Apr. 1984, pp. 1007-1015, vol. 36.
Kim, K. et al. "Cloning of the Human Glycine Transporter Type 1: Molecular and Pharmacological Characterization of Novel Isoform Variants and Chromosomal Localization of the Gene in the Human and Mouse Genomes", *Molecular Pharmacology*, 1994, pp. 608-617, vol. 45.
Liu, Q. et al. "Cloning and Expression of a Glycine Transporter from Mouse Brain", *FEBS*, 1992, pp. 110-114, vol. 305, No. 2.
Liu, W. et al. "Characterization of the Glycine Transport System GLYT 1 in Human Placental Choriocarcinoma Cells (JAR)", *Biochimica et Biophysica Acta*, 1994, pp. 176-184, vol. 1194.
Nunez, E. et al. "Differential Effects of the Tricyclic Antidepressant Amoxapine on Glycine Uptake Mediated by the Recombinant GLYT1 and GLYT2 Glycine Transporters", *British Journal of Pharmacology*, 2000, pp. 200-206, vol. 129.
Olivares, L. et al. "Analysis of the Transmembrane Topology of the Glycine Transporter GLYT1*", *The Journal of Biological Chemistry*, Jan. 10, 1997, pp. 1211-1217, vol. 272, No. 2.
Olney, J. et al. "Glutamate Receptor Dysfunction and Schizophrenia", *Arch. Gen. Psychiatry*, Dec. 1995, pp. 998-1007, vol. 52.
Rossi, J. et al. "The Potential Use of Catalytic RNAs In Therapy of HIV Infection and Other Diseases", *Pharmac. Ther.*, 1991, pp. 245-254, vol. 50.
Sczakiel, G. et al. "The Potential of Ribozymes as Antiviral Agents", *Trends in Microbiology*, 1995, pp. 213-217, vol. 3, No. 6.
Tsen, G. et al. "Receptors with Opposing Functions are in Postsynaptic Microdomains Under One Presynaptic Terminal", *Nature Neuroscience*, Feb. 2000, pp. 126-132, vol. 3, No. 2.
Uhl, G. "Neurotransmitter Transporters (plus): a Promising New Gene Family", *TINS*, 1992, pp. 265-268, vol. 15, No. 7.
Sulston, J. et al. "Toward a complete human genome sequence" *Genome Research*, 1998, pp. 1097-1108, vol. 8, No. 11.
Armer, R.E. et al. "Inhibitors of Mammalian Central Nervous System Selective Amino Acid Transporters", *Current Medicinal Chemistry*, 2000, pp. 199-209, vol. 7.

* cited by examiner

*Primary Examiner*—Olga N. Chernyshev
*Assistant Examiner*—Stacey MacFarlane
(74) *Attorney, Agent, or Firm*—Saliwanchik, Lloyd & Saliwanchik

(57) ABSTRACT

The present invention provides polypeptide and polynucleotide sequences for novel splice variants of the sodium and chloride-dependent glycine transporter type 1 (GlyT1). These polypeptides and polynucleotides are useful in the treatment and diagnosis of disorders such as neurological and psychiatric disorders including schizophrenia. The invention also provides antibodies directed specifically against these novel polypeptides, and kits comprising the herein-described polynucleotides, polypeptides, and/or antibodies.

27 Claims, 1 Drawing Sheet

VARIANTS AND EXONS OF THE GLYT1 TRANSPORTER

FIELD OF THE INVENTION

The present invention is directed to polynucleotides encoding novel exons and novel splice variants of the sodium and chloride-dependent glycine transporter type 1 (GlyT1), and their use in the treatment and diagnosis of neurological and psychiatric disorders such as schizophrenia. The invention also deals with antibodies directed specifically against these novel polypeptides which are useful, e.g., as diagnostic reagents.

BACKGROUND OF THE INVENTION

Neurotransmitter transporters play a critical role in the regulation of synaptic transmission. These transporters, which are located on the pre-synaptic terminal and surrounding glial cells, sequester neurotransmitter from the synapse, thereby regulating the synaptic concentration of neurotransmitter and influencing the duration and magnitude of synaptic transmission. Transporters also help to limit the extent of synaptic transmission by preventing the spread of transmitter to neighboring synapses. In view of the important role played by these transporters in neurological function, they represent attractive targets for pharmacological modulation, potentially providing novel methods of treatment for any of a number of psychological and neurological conditions.

The amino acid glycine functions at both inhibitory and excitatory synapses in the central and peripheral nervous systems of mammals. The excitatory and inhibitory functions of glycine are mediated by two different types of receptor, each of which is associated with a different type of glycine transporter. At excitatory synapses, glycine acts as an obligatory co-agonist at a class of glutamate receptors called N-methyl-D-aspartate (NMDA) receptors. Activation of these receptors in neurons increases sodium and calcium conductance, thereby depolarizing the neuron and increasing the likelihood that the neuron will fire an action potential.

The class of glycine transporter thought to be involved in excitatory synapses in conjunction with NMDA receptors is Glyt-1. At least four variants of GlyT-1 (GlyT-1a, GlyT-1b, GlyT-1c, and Glyt-1d), have been described. Both GlyT1 and GlyT2 transporters are members of a broader family of sodium- and chloride-dependent neurotransmitter transporters, the members of which typically have 12 transmembrane domains (Olivares et al. (1997) J. Biol. Chem. 272:1211-1217; Uhl, Trends in Neuroscience 15: 265-268, 1992; Clark et al, BioEssays 15: 323-332, 1993). Both the N- and C-termini of the members of this family are thought to be intracellular.

NMDA receptor activity has been implicated in a large number of psychological and neurological functions, such as learning and memory, and in a large number of diseases and conditions, including schizophrenia, dementias, attention-deficit hyperactive disorder, and various neurodegenerative disorders. Thus, modulators of GlyT1 proteins can used to treat these and other conditions. The present invention addresses these and other needs.

SUMMARY OF THE INVENTION

The present invention pertains to polynucleotides and polypeptides corresponding to cDNA sequences encoding 8 novel splice variants of the GlyT1 glycine transporter. Oligonucleotide probes or primers hybridizing specifically with the novel cDNA sequences are also part of the present invention, as are DNA amplification and detection methods using said primers and probes.

A further object of the invention consists of recombinant vectors comprising any of the nucleic acid sequences described herein, as well as of cell hosts and transgenic non human animals comprising these nucleic acid sequences or recombinant vectors.

The invention is also directed to methods for the screening of substances or molecules that interact with any of the present polypeptides or that modulate the activity of any of the present polypeptides.

As such, in one aspect, the present invention provides an isolated, purified, or recombinant polynucleotide comprising a nucleic acid sequence that is at least about 70%, 75%, 80%, 85%, 90%, 95%, 96%, 97%, 98%, 99%, or 100% identical to a contiguous span of at least 12, 25, 50, 100, 250, 500, 1000, or more nucleotides of any of the nucleic acid sequences shown as SEQ ID NOs:2-9 or 14-21, or a sequence complementary to any of these sequences. In another aspect, the present invention provides an isolated, purified, or recombinant polynucleotide comprising a nucleic acid sequence that encodes a functional GlyT1 transporter and which specifically hybridizes under stringent or moderate conditions with any of the nucleic acid sequences shown as SEQ ID NOs:2-9 or 14-21.

In another aspect, the present invention provides an isolated, purified, or recombinant polynucleotide comprising a nucleic acid sequence that is at least about 70%, 75%, 80%, 85%, 90%, 95% or more identical to any of the sequences shown as SEQ ID NOs:14-21, wherein the polynucleotide comprises a sequence at least about 90%, 95%, 96%, 97%, 98%, 99%, or 100% identical to any of the sequences shown as SEQ ID NOs:2-9.

In another aspect, the present invention provides an isolated, purified, or recombinant polynucleotide encoding a glycine transporter, wherein said polynucleotide hybridizes under stringent or moderate hybridization conditions with a nucleic acid comprising any of the sequences shown as SEQ ID NOs:14-21, and wherein said polynucleotide comprises any of the sequences shown as SEQ ID NOs:2-9.

In another aspect, the present invention provides an isolated, purified, or recombinant polynucleotide which encodes a polypeptide comprising an amino acid sequence that is at least about 70%, 75%, 80%, 85%, 90%, 95%, 96%, 97%, 98%, 99%, or more identical to a contiguous span of at least 6, 12, 25, 50, 100, 200, 300, 400, 500 or more amino acids of any of SEQ ID NOs:26-33. In one embodiment, the polypeptide comprises any of the amino acid sequences shown as SEQ ID NOs:26-33.

In another aspect, the present invention provides a method of producing a GlyT1 polypeptide, said method comprising the following steps: a) providing a host cell comprising a nucleic acid encoding any one of the polypeptides shown as SEQ ID NO:26-33, operably linked to a promoter; b) cultivating said host cell under conditions conducive to the expression of said polypeptide; and c) isolating said polypeptide from said host cell.

In one embodiment, the polynucleotide is attached to a solid support. In another embodiment, the polynucleotide further comprises a label. In another embodiment, the polynucleotide is operably linked to a promoter.

In another aspect, the present invention provides a biologically active fragment of any of the herein-described polynucleotides.

In another aspect, the present invention provides an array of polynucleotides comprising at least one of the herein-described polynucleotides. In one embodiment, the array is addressable.

In another aspect, the present invention provides a recombinant vector comprising any of the herein-described polynucleotides.

In another aspect, the present invention provides a host cell comprising any of the herein-described recombinant vectors or polynucleotides.

In another aspect, the present invention provides a non-human host animal or mammal comprising any of the herein-described recombinant vectors or polynucleotides.

In another aspect, the present invention provides an isolated, purified, or recombinant polypeptide comprising an amino acid sequence that is at least about 70%, 75%, 80%, 85%, 90%, 95%, 96%, 97%, 98%, 99%, or more identical to a contiguous span of at least 6, 12, 25, 50, 100, 250, 500, or more amino acids of any of the sequences shown as SEQ ID NOs:26-33. In one embodiment, the polypeptide comprises any of the sequences shown as SEQ ID NOs:26-33.

In another aspect, the present invention provides an isolated, purified, or recombinant polypeptide, wherein the polypeptide comprises an amino acid sequence encoded by any of the nucleic acid sequences shown as SEQ ID NOs:2-9 or 14-21.

In another aspect, the present invention provides a biologically active fragment of any of the herein-described polypeptides.

The invention further relates to methods of making the polypeptides of the present invention.

In another aspect, the present invention provides an isolated or purified antibody capable of selectively binding to an epitope-containing fragment of any of the herein-described polypeptides, such as the polypeptides encoded by any of the sequences shown as SEQ ID NOs: 2-9 or 14-21, or the polypeptides comprising any of the amino acid sequences shown as SEQ ID NOs:26-33.

In another aspect, the present invention provides a method of binding an anti-GlyT1 antibody to any of the herein-described polypeptides, e.g. polypeptides encoded by any of SEQ ID NOs;2-9 or 14-21, or comprising any of the sequences shown as SEQ ID NOs:26-33, said method comprising contacting said antibody with said polypeptide under conditions in which said antibody can specifically bind to said polypeptide.

The present invention further relates to transgenic plants or animals, wherein said transgenic plant or animal is transgenic for a polynucleotide of the present invention and expresses a polypeptide of the present invention, or in which a polynucleotide of the present invention has been specifically disrupted or replaced with an inactive version of the polynucleotide, or with a substitute version having altered properties.

In another aspect, the present invention provides a diagnostic kit comprising any of the herein described polynucleotides, polypeptides, or antibodies.

The invention also provides kits, uses and methods for detecting the expression and/or biological activity of any of the herein-described GlyT1 variants, e.g., in a biological sample. One such method involves assaying for expression using the polymerase chain reaction (PCR), e.g., RT-PCR, to detect mRNA encoding any of the variants. In another method, Northern blot hybridization is used. Alternatively, a method of detecting gene expression in a test sample can be accomplished using a compound which binds to any of the herein-described polypeptides, e.g. a GlyT1-specific antibody, preferably a variant-specific anti-GlyT1 antibody.

In another aspect, the present invention provides a method of detecting the expression of a GlyT1 gene within a cell, said method comprising the steps of: a) contacting said cell or an extract from said cell with either of: i) a polynucleotide that hybridizes under stringent conditions to any of the herein-described GlyT1 polynucleotides; or ii) a compound that specifically binds to any of the herein-described GlyT1 polypeptides; and b) detecting the presence or absence of hybridization between said polynucleotide and an RNA species within said cell or extract, or the presence or absence of binding of said compound to a protein within said cell or extract; wherein a detection of the presence of said hybridization or of said binding indicates that said GlyT1 gene is expressed within said cell.

In one embodiment, said polynucleotide is an oligonucleotide primer, and wherein said hybridization is detected by detecting the presence of an amplification product comprising the sequence of said primer. In another embodiment, said compound is an anti-GlyT1 antibody.

In another aspect, the present invention provides a method of identifying a candidate modulator of a GlyT1 polypeptide, said method comprising: a) contacting any of the herein-described GlyT1 polypeptides with a test compound; and b) determining whether said compound specifically binds to said polypeptide; wherein a detection that said compound specifically binds to said polypeptide indicates that said compound is a candidate modulator of said GlyT1 polypeptide.

In one embodiment, the method further comprises testing the activity of said GlyT1 polypeptide in the presence of said candidate modulator, wherein a difference in the activity of said GlyT1 polypeptide in the presence of said candidate modulator in comparison to the activity in the absence of said candidate modulator indicates that the candidate modulator is a modulator of said GlyT1 polypeptide.

In another aspect, the present invention provides a method of identifying a modulator of a GlyT1 polypeptide, said method comprising: a) contacting any of the herein-described polypeptides with a test compound; and b) detecting the activity of said polypeptide in the presence and absence of said compound; wherein a detection of a difference in said activity in the presence of said compound in comparison to the activity in the absence of said compound indicates that said compound is a modulator of said GlyT1 polypeptide.

In one embodiment of these methods, said polypeptide is present in a cell or cell membrane, and wherein said activity comprises glycine tranport activity.

In another aspect, the present invention provides a method for the preparation of a pharmaceutical composition comprising a) identifying a modulator of a GlyT1 polypeptide using any of the herein-described methods; and b) combining said modulator with a physiologically acceptable carrier.

The present invention also relates to diagnostic methods and uses of the present polynucleotides and polypeptides for identifying humans or non-human animals having elevated or reduced levels of expression of any one or combination of the herein-described variants, which individuals are likely to benefit from therapies to suppress or enhance the expression of the variant or variants, respectively, and to methods of identifying individuals or non-human animals at increased risk for developing, or at present having, diseases or disorders associated with expression or biological activity of any one or combination of the herein-described variants.

The present invention also relates to kits, uses and methods for screening compounds for their ability to modulate (e.g. increase or inhibit) the activity or expression of any of the present variants. Uses of such compounds are also within the scope of the present invention.

The present invention also relates to pharmaceutical or physiologically acceptable compositions comprising, an active agent, the polypeptides, polynucleotides or antibodies of the present invention, as well as, typically, a pharmaceutically acceptable carrier.

The present invention also provides the use of any of the herein-described GlyT1 polynucleotides, polypeptides, antibodies, modulators, or kits, in the diagnosis or treatment of any disorder, preferably a neurological or psychiatric disorder such as schizophrenia, or in the preparation of a medicament for the treatment of any disorder including neurological or psychiatric disorders such as schizophrenia.

In another aspect, the present invention provides a computer readable medium having stored thereon a sequence selected from the group consisting of a nucleic acid code comprising a contiguous span of at least 12, 15, 18, 20, 25, 30, 35, 40, 50, 60, 70, 80, 90, 100, 150, 200, 500, or 1000 nucleotides of any of the sequences shown as SEQ ID NOs:2-9 or 14-21.

In another aspect, the present invention provides a computer readable medium having stored thereon a sequence consisting of a polypeptide code comprising a contiguous span of at least 6, 8, 10, 12, 15, 20, 25, 30, 40, 50, or 100 amino acids of any of the amino acid sequences shown as SEQ ID NOs:26-33.

In another aspect, the present invention provides a computer system comprising a processor and a data storage device, wherein said data storage device comprises any of the herein-described computer readable media.

In one embodiment, the computer system further comprises a sequence comparer and a data storage device having reference sequences stored thereon. In another embodiment, the computer system further comprises an identifier which identifies features in said sequence.

BRIEF DESCRIPTION OF THE SEQUENCES PROVIDED IN THE SEQUENCE LISTING

Figure 1:
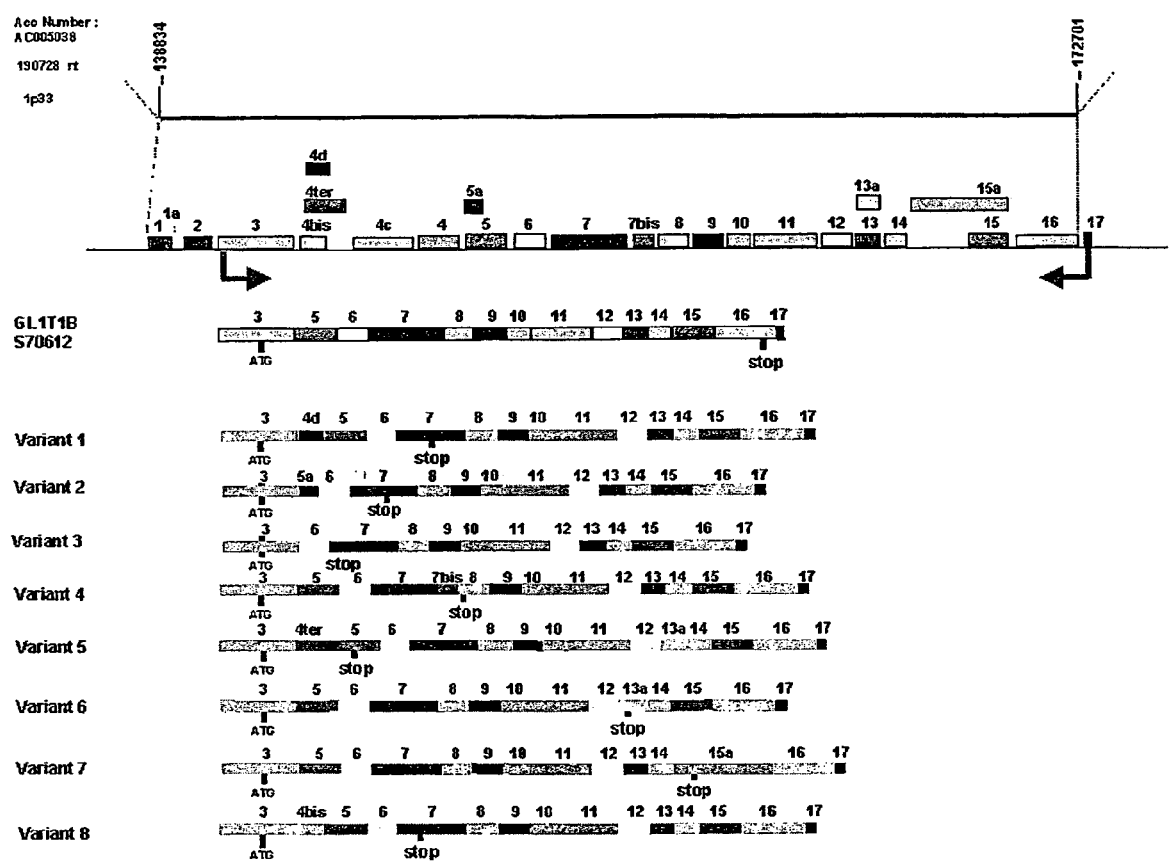
FIG. 1 shows the 8 novel GlyT1 splice variants of the present invention. The exon structure is shown for each variant in comparison with the structure for the previously described variant of Genbank accession no. S70612. The genomic structure for all of the exons is also indicated within the genomic sequence presented in Genbank accession no. AC005038.

SEQ ID NO: 1 provides genomic sequence of the GlyT1 gene, comprising the 5' regulatory region (upstream untranscribed region), the exons and introns, and the 3' regulatory region (downstream untranscribed region).

SEQ ID NOs: 2-9 provide novel exons of the GlyT1 gene.

SEQ ID NOs:10-13 provide DNA sequences encoding previously known GlyT1 variants (GlyT1a, GlyT1b, GlyT1c, GlyT1d).

SEQ ID NOs:14-21 provide novel DNA sequences encoding novel GlyT1 variants (Genset variants 1-8).

SEQ ID NOs:22-25 provide protein sequences of previously known GlyT1 variants.

SEQ ID NOs:26-33 provide protein sequences of the novel Genset GlyT1 variants.

SEQ ID NOs:34 and 35 provide the sequences of oligonucleotides SLC6A9LF and SLC6A9LR, which were used in the cloning of the presently-provided GlyT1 variants.

SEQ ID NO:36 provides a primer sequence containing the additional PU 5' sequence described further in Example 2.

SEQ ID NO:37 provides a primer sequence containing the additional RP 5' sequence described further in Example 2.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine.

In some instances, the polymorphic bases of biallelic markers alter the identity of one or more amino acids in the encoded polypeptide. This is indicated in the accompanying Sequence Listing by use of the feature VARIANT, placement of an Xaa at the position of the polymorphic amino acid, and definition of Xaa as the two alternative amino acids. For example if one allele of a biallelic marker is the codon CAC, which encodes histidine, while the other allele of the biallelic marker is CAA, which encodes glutunine, the Sequence Listing for the encoded polypeptide will contain an Xaa at the location of the polymorphic amino acid. In this instance, Xaa would be defined as being histidine or glutamine.

In other instances, Xaa may indicate an amino acid whose identity is unknown because of nucleotide sequence ambiguity. In this instance, the feature UNSURE is used, placement of an Xaa at the position of the unknown amino acid and definition of Xaa as being any of the 20 amino acids or a limited number of amino acids suggested by the genetic code.

DETAILED DESCRIPTION

The present invention concerns novel polynucleotides and polypeptides related to the GlyT1 gene. Oligonucleotide probes and primers hybridizing specifically with these novel polynucleotides are also part of the invention. A further object of the invention consists of recombinant vectors comprising any of the nucleic acid sequences described in the present invention, as well as cell hosts comprising said nucleic acid sequences or recombinant vectors. The invention also encompasses methods of screening for molecules which modulate the activity of the present proteins. The invention also deals with antibodies directed specifically against the present polypeptides, which are useful as diagnostic reagents.

Definitions

Before describing the invention in greater detail, the following definitions are set forth to illustrate and define the meaning and scope of the terms used to describe the invention herein.

The terms "GlyT1 gene", when used herein, encompasses genomic, mRNA and cDNA sequences encoding the GlyT1 protein, including the untranslated regulatory regions of the genomic DNA, and including any of the herein-described variants.

A GlyT1 "variant" can refer to any GlyT1 polynucleotide or polypeptide, in particular a GlyT1 polypeptide or polynucleotide differing at one or more nucleotides or amino acids from other GlyT1 sequences, especially differing from other GlyT1 sequences as a result of differential mRNA splicing. Most specifically, GlyT1 variants refer to the novel GlyT1 polynucleotides and polypeptides shown here as SEQ ID NOs: 14-21 and 26-33, and to conservatively substituted relatives thereof.

The term "heterologous protein", when used herein, is intended to designate any protein or polypeptide other than a GlyT1 protein of interest.

A "functional" glycine transporter refers to any polypeptide with one or more detectable activities of glycine transporters such as full-length GlyT1, such as the ability to transport glycine across a membrane in in vitro or in vivo assays, and also including glycine binding, neuronal activation in cells expressing the transporter, interaction with additional ligands, etc. Examples of such assays can be found in the section entitled, "methods for identifying modulators of GlyT1 activity."

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such q polynucleotide could be part of a vector and/or such polynucleotide or polypeptide could be part of a composition, and still be isolated in that the vector or composition is not part of its natural environment.

For example, a naturally-occurring polynucleotide present in a living animal is not isolated, but the same polynucleotide, separated from some or all of the coexisting materials in the natural system, is isolated. Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude. To illustrate, individual cDNA clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately 104-106 fold purification of the native message.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups; acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide, i.e. using recombinant DNA methods.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)2, and F(ab')2 fragments.

As used herein, an "antigenic determinant" is the portion of an antigen molecule, in this case a GLYT1 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope comprises at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

As used herein, the term "operably linked" refers to a linkage of polynucleotide elements in a functional relationship. For instance, a promoter or enhancer is operably linked to a coding sequence if it affects the transcription of the coding sequence.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, without being limited to, neurological and psychiatric conditions such as schizophrenia.

The term "allele" is used herein to refer to variants of a nucleotide sequence. A biallelic polymorphism has two forms. Diploid organisms may be homozygous or heterozygous for an allelic form.

The term "heterozygosity rate" is used herein to refer to the incidence of individuals in a population which are heterozygous at a particular allele. In a biallelic system, the heterozygosity rate is on average equal to 2Pa(1-Pa), where Pa is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker involves determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The term "upstream" is used herein to refer to a location which is toward the 5' end of the polynucleotide from a specific reference point, and "downstream" refers to locations in the 3' direction.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., Biochemistry, 4th edition, 1995).

The terms "complementary" or "complement thereof"0 are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

Variants and Fragments

1-Polynucleotides

The invention also relates to variants and fragments of the polynucleotides described herein.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of the nucleotide sequences of SEQ ID Nos: 2-9 or 14-21, or to any polynucleotide fragment of at least 12 consecutive nucleotides of a polynucleotide selected from the group consisting of the nucleotide sequences of SEQ ID Nos 2-9 or 14-21, and preferably at least 99% identical, more particularly at least 99.5% identical, and most preferably at least 99.8% identical to a polynucleotide selected from the group consisting of the nucleotide sequences of SEQ ID Nos 2-9 or 14-21, or to any polynucleotide fragment of at least 12 consecutive nucleotides of a polynucleotide selected from the group consisting of the nucleotide sequences of SEQ ID Nos: 2-9 or 14-21.

In particular, the present invention comprises polynucleotide and polypeptide sequences spanning regions comprising biallelic markers within the GlyT1 gene. Methods of identifying such markers, and of using them for diagnosis, gene mapping, association studies, and other applications are well known to those of skill in the art.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature GlyT1 protein, or those in which the polynucleotides encode polypeptides which maintain or increase a particular biological activity, while reducing a second biological activity.

A polynucleotide fragment is a polynucleotide having a sequence that is entirely the same as part but not all of a given nucleotide sequence, preferably the nucleotide sequence of a GlyT1 gene, and variants thereof. The fragment can be a portion of an intron or an exon of a GlyT1 gene. It can also be a portion of the regulatory regions of GlyT1.

Such fragments may be "free-standing", i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least 8, 10, 12, 15, 18, 20, 25, 35, 40, 50, 70, 80, 100, 250, 500 or 1000 nucleotides in length.

2-Polypeptides

The invention also relates to variants, fragments, analogs and derivatives of the polypeptides described herein, including mutated GlyT1 proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated GlyT1 is fused with another compound, such as a compound to increase the half-life of the polypeptide (for example, polyethylene glycol), or 4) one in which the additional amino acids are fused to the mutated GlyT1, such as a leader or secretory sequence or a sequence which is employed for purification of the mutated GlyT1 or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a GlyT1 gene and variants thereof.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr, (2) Cys, Ser, Tyr, Thr, (3) Val, Ile, Leu, Met, Ala, Phe; (4) Lys, Arg, His; (5) Phe, Tyr, Trp, His.

A specific embodiment of a modified GlyT1 peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2—O) methylene-oxy bond, a (CH2—S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH— bond. The invention also encompasses a human GlyT1 polypeptide or a fragment or a variant thereof in which at least one peptide bond has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. In one embodiment, the fragments contain at least one amino acid mutation in the GlyT1 protein.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

The BLAST programs may be used with the default parameters or with modified parameters provided by the user.

Stringent Hybridization Conditions

For the purpose of defining such a hybridizing nucleic acid according to the invention, the stringent hybridization conditions are the followings:

The hybridization step is realized at 65° C. in the presence of 6×SSC buffer, 5× Denhardt's solution, 0,5% SDS and 100 µg/ml of salmon sperm DNA.

The hybridization step is followed by four washing steps:

two washings during 5 min, preferably at 65° C. in a 2×SSC and 0.1% SDS buffer;

one washing during 30 min, preferably at 65° C. in a 2×SSC and 0.1% SDS buffer, one washing during 10 min, preferably at 65° C. in a 0.1×SSC and 0.1% SDS buffer, these hybridization conditions being suitable for a nucleic acid molecule of about 20 nucleotides in length. There is no need to say that the hybridization conditions described above are to be adapted according to the length of the desired nucleic acid, following techniques well known to the one skilled in the art. Suitable hybridization conditions may for example be adapted according to the teachings disclosed in the book of Hames and Higgins (1985).

GlyT1 cDNA Sequences

The expression of the GlyT1 gene has been shown to lead to the production of a number of distinct mRNA species, the novel nucleic acid sequences of eight of which are set forth herein as SEQ ID Nos: 14-21.

Another object of the invention is a purified, isolated, or recombinant nucleic acid comprising the nucleotide sequence of SEQ ID Nos: 14-21, complementary sequences thereto, as well as allelic variants, and fragments thereof. Moreover, preferred polynucleotides of the invention include purified, isolated, or recombinant GlyT1 cDNAs consisting of, consisting essentially of, or comprising the sequence of SEQ ID Nos:2-9. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID Nos:2-9 or 14-21, or the complements thereof.

The invention also pertains to a purified or isolated nucleic acid comprising a polynucleotide having at least 95% nucleotide identity with a polynucleotide of SEQ ID Nos:2-9 or 14-21, advantageously 99% nucleotide identity, preferably 99.5% nucleotide identity and most preferably 99.8% nucleotide identity with a polynucleotide of SEQ ID Nos: 2-9 or 14-21, or a sequence complementary thereto or a biologically active fragment thereof.

Another object of the invention relates to purified, isolated or recombinant nucleic acids comprising a polynucleotide that hybridizes, under the stringent hybridization conditions defined herein, with a polynucleotide comprising a sequence of SEQ ID Nos: 2-9 or 14-21, or a sequence complementary thereto, or a variant thereof or a biologically active fragment thereof.

The novel cDNAs of the present invention comprise novel combinations of previously identified exons, as well as novel exons. For example, Table I provides a list of the exons present in previously-identified variants GlyT1a-GlyT1d, as well as the presently provided novel variants. SEQ ID NO:1 provides the genomic DNA sequence of the GlyT1 gene, and notes the positions of each of the herein-referenced exons. The exon structure of the novel variants is also presented in FIG. 1.

TABLE I

Variants of the GlyT1 gene

| Variant | Exon configuration | Size of Encoded protein (aa) |
|---|---|---|
| 1a | 1, 2, 5-16 | 633 |
| 1b | 3, 5-16 | 638 |
| 1c | 3-16 | 692 |
| 1d | 1a, 2, 4-16 | 687 |
| Genset Variant 1 | 3, 4d, 5-16 | 184 |
| Genset Variant 2 | 3, 5a, 6-16 | 125 |
| Genset Variant 3 | 3, 6-16 | 64 |
| Genset Variant 4 | 3, 5-7, 7bis, 8-16 | 229 |
| Genset Variant 5 | 3, 4ter, 5-12, 13a, 14-16 | 94 |
| Genset Variant 6 | 3, 5-12, 13a, 14-16 | 456 |
| Genset Variant 7 | 3, 5-14, 15a, 16 | 550 |
| Genset Variant 8 | 3, 4bis, 5-16 | 188 |

The cDNA of SEQ ID No: 14 (Genset variant 1) includes a 5'-UTR region staring from the nucleotide at position 1 and ending at the nucleotide in position 234, an open reading frame spanning the nucleotide positions 235-789, and a 3'-UTR region starting from the nucleotide at position 790 and ending at the nucleotide at position 2265. The protein encoded by this cDNA comprises 184 amino acids and is shown as SEQ ID NO:26.

The cDNA of SEQ ID No: 15 (Genset variant 2) includes a 5'-UTR region starting from the nucleotide at position 1 and ending at the nucleotide in position 234, an open reading frame spanning the nucleotide positions 235-612, and a 3'-UTR region starting from the nucleotide at position 613 and ending at the nucleotide at position 2088. The protein encoded by this cDNA comprises 125 amino acids and is shown as SEQ ID NO:27.

The cDNA of SEQ ID No: 16 (Genset variant 3) includes a 5'-UTR region starting from the nucleotide at position 1 and ending at the nucleotide in position 234, an open reading frame spanning the nucleotide positions 235-429, and a 3'-UTR region starting from the nucleotide at position 430 and ending at the nucleotide at position 2014. The protein encoded by this cDNA comprises 64 amino acids and is shown as SEQ ID NO:28.

The cDNA of SEQ ID No: 17 (Genset variant 4) includes a 5'-UTR region starting from the nucleotide at position 1 and ending at the nucleotide in position 234, an open reading frame spanning the nucleotide positions 235-924, and a 3'-UTR region starting from the nucleotide at position 925 and ending at the nucleotide at position 2242. The protein encoded by this cDNA comprises 229 amino acids and is shown as SEQ ID NO:29.

The cDNA of SEQ ID No: 18 (Genset variant 5) includes a 5'-UTR region starting from the nucleotide at position 1 and ending at the nucleotide in position 234, an open reading frame spanning the nucleotide positions 235-519, and a 3'-UTR region starting from the nucleotide at position 520 and ending at the nucleotide at position 2322. The protein encoded by this cDNA comprises 94 amino acids and is shown as SEQ ID NO:30.

The cDNA of SEQ ID No: 19 (Genset variant 6) includes a 5'-UTR region starting from the nucleotide at position 1 and ending at the nucleotide in position 234, an open reading frame spanning the nucleotide positions 235-1605, and a 3'-UTR region starting from the nucleotide at position 1606 and ending at the nucleotide at position 2167. The protein encoded by this cDNA comprises 456 amino acids and is shown as SEQ ID NO:31.

The cDNA of SEQ ID No: 20 (Genset variant 7) includes a 5'-UTR region starting from the nucleotide at position 1 and ending at the nucleotide in position 234, an open reading frame spanning the nucleotide positions 235-1887, and a 3'-UTR region starting from the nucleotide at position 1888 and ending at the nucleotide at position 2371. The protein encoded by this cDNA comprises 550 amino acids and is shown as SEQ ID NO:32.

The cDNA of SEQ ID No: 21 (Genset variant 8) includes a 5'-UTR region starting from the nucleotide at position 1 and ending at the nucleotide in position 234, an open reading frame spanning the nucleotide positions 235-801, and a 3'-UTR region starting from the nucleotide at position 802 and ending at the nucleotide at position 2277. The protein encoded by this cDNA comprises 188 amino acids and is shown as SEQ ID NO:33.

Consequently, the invention concerns a purified, isolated, and/or recombinant nucleic acid comprising a nucleotide sequence of the 5'UTR of any of the herein-provided GlyT1 cDNAs, a sequence complementary thereto, or an allelic variant thereof. The invention also concerns a purified, isolated, and/or recombinant nucleic acid comprising a nucleotide sequence of the 3'UTR of any of the herein-provided GlyT1 cDNAs, a sequence complementary thereto, or an allelic variant thereof.

While this section is entitled "GLYT1 cDNA Sequences," it should be noted that nucleic acid fragments of any size and sequence may also be comprised by the polynucleotides described in this section, flanking the genomic sequences of GLYT1 on either side or between two or more such genomic sequences.

Coding Regions

The open reading frames of the novel GlyT1 cDNAs provided herein are contained in the corresponding mRNAs of SEQ ID Nos: 14-21, as outlined in the previous section. The present invention also embodies isolated, purified, and/or recombinant polynucleotides which encode a polypeptide comprising a contiguous span of at least 6 amino acids, preferably at least 8 or 10 amino acids, more preferably at least 12, 15, 20, 25, 30, 40, 50, 100, 200 or more amino acids of any of SEQ ID Nos:26-33.

Certain of the present novel GlyT1 cDNAs comprise novel exons, which are shown as SEQ ID Nos:2-9. Thus, the present invention also provides purified, isolated, or recombinant polynucleotides that comprise a nucleotide sequence of SEQ ID Nos: 2-9, complementary sequences thereto, as well as allelic variants and fragments thereof. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 300, or more nucleotides of SEQ ID Nos:2-9, the complements thereof, or which comprise a nucleotide sequence that is at least 70%, 75%, 80%, 85%, 90%, 95%, 96%, 97%, 98%, 99%, or more identical to any of the sequences shown as SEQ ID NOs:2-9. In a preferred embodiment, the present invention provides a nucleic acid sequence that is at least about 70%, 75%, 80%, 85%, 90%, 95%, 96%, 97%, 98%, 99%, or more identical to any of the sequences shown as SEQ ID NOs 14-21, or which hybridize under stringent or moderate conditions to any of the sequences shown as SEQ ID Nos: 14-21, wherein the nucleic acid sequence comprises any of the sequences shown as SEQ ID NOs:2-9.

Any of the above-disclosed polynucleotides containing a coding sequence of the GlyT1 gene may be expressed in a desired host cell or a desired host organism, when the polynucleotide is placed under the control of suitable expression signals. The expression signals may be either the expression signals contained in the regulatory regions in the GlyT1 gene of the invention, or, in contrast, the signals may be exogenous regulatory nucleic sequences. Such a polynucleotide, when placed under the suitable expression signals, may also be inserted in a vector for its expression and/or amplification.

Regulatory Sequences of GlyT1

As mentioned, the genomic sequence of the GlyT1 gene contains regulatory sequences both in the non-coding 5'-flanking region and in the non-coding 3'-flanking region that border the coding regions containing the exons of the various cDNAs. The positions of these 5'-regulatory sequence of the novel GlyT1 cDNAs are described in the section entitled, "GlyT1 cDNA sequences," supra.

Biologically active polynucleotide fragments or variants of any of the herein described novel cDNAs (e.g. the 5'UTRs or 3'UTRs) can be detected, e.g., by inserting a candidate sequence into a recombinant vector carrying a detectable marker gene (i.e. beta galactosidase, chloramphenicol acetyl transferase, etc.) (see, e.g., Sambrook et al. (1989)).

Polynucleotides derived from any of these 5' and 3' regulatory regions are useful, inter alia, in the detection of at least a copy of any of the nucleotide sequences of SEQ ID No:1 or 14-21, or a fragment thereof, in a test sample. Polynucleotides carrying the regulatory elements located at the 5' end and at the 3' end of the GLYT1 coding region may also be used to control the transcriptional and translational activity of an heterologous polynucleotide of interest. In addition, polynucleotides from regulatory regions of a GlyT1 gene can be used to identify GlyT1 or related genes elsewhere in the genome of the same species or in the genomes of heterologous species.

Thus, the present invention also concerns a purified or isolated nucleic acid comprising a polynucleotide which is selected from the group consisting of the 5' and 3' regulatory regions, a sequence complementary thereto, and biologically active fragments or variants thereof.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, a sequence complementary thereto, a variant thereof, and a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, a sequence complementary thereto, a variant thereof, and a biologically active fragment thereof.

Preferred fragments of the 5' regulatory region have a length of about 1500 or 1000 nucleotides, preferably of about 500 nucleotides, more preferably about 400 nucleotides, even more preferably 300 nucleotides and most preferably about 200 nucleotides.

Preferred fragments of the 3' regulatory region are at least 50, 100, 150, 200, 300 or 400 bases in length.

"Biologically active" regulatory polynucleotide derivatives of SEQ ID Nos: 14-21 are polynucleotides comprising or alternatively consisting of a fragment of said polynucleotide which is functional as a regulatory region for expressing a recombinant polypeptide or a recombinant polynucleotide in a recombinant cell host. It could act either as an enhancer or as a repressor of transcription or translation. For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information. Such sequences can then be "operably linked" to nucleotide sequences which encode the desired polypeptide or the desired polynucleotide.

The regulatory polynucleotides of the invention may be prepared from the nucleotide sequence of SEQ ID No: 1 or any of SEQ ID Nos:14-21 by cleavage using suitable restriction enzymes, as described for example in Sambrook et al. (1989). The regulatory polynucleotides may also be prepared by digestion of SEQ ID No:1 or any of SEQ ID Nos:14-21 by an exonuclease enzyme, such as Bal31 (Wabiko et al., 1986). These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

The desired nucleic acids encoded by the above-described polynucleotide, e.g. an RNA molecule, may be complementary to a desired coding polynucleotide, for example to the GlyT1 coding sequence, and thus useful as an antisense polynucleotide.

Such a polynucleotide may be included in a recombinant expression vector in order to express the desired polypeptide or the desired nucleic acid in host cell or in a host organism. Suitable recombinant vectors that contain a polynucleotide such as described herein are disclosed elsewhere in the specification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

In order to study the physiological and phenotypic consequences of a lack of synthesis of the GlyT1 protein, both at the cell level and at the multi-cellular organism level, the invention also encompasses DNA constructs and recombinant vectors enabling a conditional expression of specific cDNAs encoded by the GlyT1 genomic sequence or variants, derivatives, or fragments thereof.

The present invention embodies recombinant vectors comprising any one of the polynucleotides described in the present invention. Preferably, the polynucleotide constructs according to the present invention comprise any of the polynucleotides described in the "GlyT1 cDNA Sequences" section, the "Coding Regions" section, and the "Oligonucleotide Probes And Primers" section.

One preferred DNA construct is based on the tetracycline resistance operon tet from E. coli transposon Tn10 for controlling the GlyT1 gene expression, such as described by Gossen et al. (1992, 1995) and Furth et al. (1994). Such a DNA construct contains seven tet operator sequences from Tn10 (tetop) that are fused to either a minimal promoter and/or a 5'-regulatory sequence of the GlyT1 gene, said minimal promoter or said GlyT1 regulatory sequence being operably linked to a polynucleotide of interest that codes either for a sense or an antisense oligonucleotide or for a polypeptide, including a GlyT1 polypeptide (preferably a novel GlyT1 polypeptide provided herein) or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

The present DNA constructs may be used to introduce a desired nucleotide sequence of the invention, preferably a novel GlyT1 cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination).

Nuclear Antisense DNA Constructs

Other compositions containing a vector of the invention comprising an oligonucleotide fragment of any of the nucleic acid sequences shown as SEQ ID Nos: 2-9 or 14-21, preferably a fragment including the start codon of any of the present novel GlyT1 cDNAs, as an antisense tool that inhibits the expression of the corresponding GlyT1 cDNA. Preferred methods using antisense polynucleotide according to the present invention are the procedures described by Sczakiel et al. (1995) or those described in PCT Application No WO 95/24223, the disclosures of which are incorporated by reference herein in their entirety.

Preferably, the antisense tools are chosen among the polynucleotides (15-200 bp long) that are complementary to the 5' end of the GlyT1 mRNA. In one embodiment, a combination of different antisense polynucleotides complementary to different parts of the desired targeted gene are used. Preferred antisense polynucleotides according to the present invention are complementary to a sequence of any of the present GlyT1 mRNAs that contains either the translation initiation codon ATG or a splicing site. Further preferred antisense polynucleotides according to the invention are complementary of a splicing site of any of the present GlyT1 mRNAs.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these GlyT1 antisense polynucleotides also comprise, within the ribozyme cassette, a histone stem-loop structure to stabilize cleaved transcripts against 3'-5' exonucleolytic degradation, such as the structure described by Eckner et al. (1991).

Oligonucleotide Probes and Primers

Polynucleotides derived from the GlyT1 gene are useful in order to detect the expression of any of the novel cDNAs shown as SEQ ID Nos:14-21, or any cDNA comprising any of the novel exons shown as SEQ ID Nos:2-9, or fragments, complements, or variants thereof in a test sample.

Particularly preferred probes and primers of the invention include isolated, purified, or recombinant polynucleotides comprising, consisting of, or consisting essentially of, a contiguous span of at least 12, 15, 18, 20, 25, 30, 35, 40, 50, 60, 70, 80, 90, 100, 150, 200, 500, 1000 or more nucleotides of SEQ ID Nos:2-9 or 14-21, or the complements thereof.

Thus, the invention also relates to nucleic acid probes characterized in that they hybridize specifically, under the stringent hybridization conditions defined above, with any of the novel cDNAs or exons described herein, e.g. as shown as SEQ ID NOs:2-9 or 14-21, or sequences complementary thereto.

In a preferred embodiment, said probes comprises, consists of, or consists essentially of a sequence selected from SEQ ID NOs:34, 35, 36, and 37, and the complementary sequences thereto.

In an additional embodiment, the invention encompasses polynucleotides for use in hybridization assays, sequencing assays, and enzyme-based mismatch detection assays for determining the expression of particular cDNA species encoded by the GlyT1 gene, e.g. the expression of any of the herein provided novel cDNAs, or the expression of any cDNAs comprising any of the herein-provided novel exons.

The invention concerns the use of the polynucleotides according to the invention for detecting the expression of any of the herein-provided novel cDNAs, or the expression of any cDNAs comprising any of the herein-provided novel exons, preferably in hybridization assays, sequencing assays, microsequencing assays, enzyme-based mismatch detection assays, or by amplifying segments of nucleotides comprising any of the present novel exons, or spanning any novel exon-exon junctions found in any of the present novel cDNAs (i.e. novel junctions resulting from novel exon configurations; see, e.g., Table I).

A probe or a primer according to the invention preferably has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers typically ranges from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592.

Detection probes are generally nucleic acid sequences or uncharged nucleic acid analogs such as, for example peptide nucleic acids which are disclosed in PCT Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified; U.S. Pat. No. 4,869,905 describes modifications which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, 32P, 35S, 3H, 125I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in French patent No. FR-7810975 or by Urdea et al. (1988) or Sanchez-Pescador et al. (1988). In addition, the probes according to the present invention may have structural characteristics such that they allow the signal amplification, such structural characteristics being, for example, branched DNA probes as those described by Urdea et al. (1991) or in European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the GLYT1 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Oligonucleotide Arrays

A substrate comprising a plurality of oligonucleotide primers or probes of the invention may be used, e.g., to detect expression of a plurality of any of the herein-provided cDNAs, or to detect the expression of one or more of the present cDNAs in conjunction with the expression of one or more heterologous genes.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VSLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

Consequently, the invention concerns an array of nucleic acid molecules comprising at least one polynucleotide described above as probes and primers. Preferably, the invention concerns an array of nucleic acid comprising at least two polynucleotides described above as probes and primers.

GlyT1 Proteins and Polypeptide Fragments

The term "GlyT1 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies GlyT1 proteins from humans, including isolated or purified GlyT1 proteins consisting of, consisting essentially of, or comprising any of the sequences of SEQ ID Nos:26-33.

The invention concerns polypeptides encoded by a nucleotide sequence selected from the group consisting of SEQ ID Nos:2-9 or 14-21, a complementary sequence thereof or a fragment thereof.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID Nos:26-33. The present invention also embodies isolated, purified, and recombinant polypeptides comprising a contiguous span of at least 6 amino acids, preferably at least 8 to 1 amino acids, more preferably at least 12, 15, 20, 25, 30, 40, 50, or 100 amino acids encoded by any of the exons shown as SEQ ID NOs:2-9.

The invention also encompasses purified, isolated, or recombinant polypeptides comprising an amino acid sequence having at least 70, 75, 80, 85, 90, 95, 98 or 99% amino acid identity with any of the amino acid sequences of SEQ ID NO:26-33, or any of the amino acid sequences encoded by any of the nucleic acid sequences shown as SEQ D NO:2-9 or 14-21, or a fragment thereof.

GlyT1 proteins are preferably isolated from human or mammalian tissue samples or expressed from human or mammalian genes. The GlyT1 polypeptides of the invention can be made using routine expression methods known in the art. For example, a polynucleotide encoding the desired polypeptide is ligated into an expression vector suitable for any convenient host. Either eukaryotic or prokaryotic host systems can be used to produce recombinant polypeptides. The polypeptide is then isolated from lysed cells or from the culture medium and purified to the extent needed for its intended use. Purification can be carried out using any technique known in the art, for example, differential extraction, salt fractionation, chromatography, centrifugation, and the like. See, for example, Methods in Enzymology for a variety of methods for purifying proteins.

In addition, shorter protein fragments can be produced by chemical synthesis. Alternatively, the proteins of the invention can be extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, or gel electrophoresis.

Any GlyT1 polynucleotide, preferably a novel cDNA shown as SEQ ID Nos: 14-21, can be used to express GlyT1 proteins and polypeptides. The nucleic acid encoding the GlyT1 protein or polypeptide to be expressed can be operably linked to a promoter in an expression vector using conventional cloning technology. The GlyT1 insert in the expression vector may comprise the full coding sequence for the GlyT1 protein or a portion thereof. For example, the GlyT1 derived insert may encode a polypeptide comprising at least 10 consecutive amino acids of the GlyT1 protein of SEQ ID Nos: 26-33, or a protein encoded by any of the nucleic acids shown as SEQ ID NOs:2-9 or 14-21.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767, the disclosure of which is incorporated by reference herein in its entirety.

In one embodiment, the entire coding sequence of the cDNA through the poly A signal of the cDNA are operably linked to a promoter in the expression vector. Alternatively, if the nucleic acid encoding a portion of the GlyT1 protein lacks a methionine to serve as the initiation site, an initiating methionine can be introduced next to the first codon of the nucleic acid using conventional techniques. Similarly, if the insert from the GlyT1 cDNA lacks a poly A signal, this sequence can be added to the construct by, for example, splicing out the Poly A signal from pSG5 (Stratagene) using BgII and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The finished constructs may be transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

The expressed protein may be purified using conventional purification techniques such as ammonium sulfate precipitation or chromatographic separation based on size or charge. The protein encoded by the nucleic acid insert may also be purified using standard immunochromatography techniques. In such procedures, a solution containing the expressed GlyT1 protein or portion thereof, such as a cell extract, is applied to a column having antibodies against the GlyT1 protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the GlyT1 protein or a portion thereof, the proteins expressed from host cells containing an expression vector containing an insert encoding the GlyT1 protein or a portion thereof can be compared to the proteins expressed in host cells containing the expression vector without an insert The presence of a band in samples from cells containing the expression vector with an insert which is absent in samples from cells containing the expression vector without an insert indicates that the GlyT1 protein or a portion thereof is being expressed. Generally, the band will have the mobility expected for the GlyT1 protein or portion thereof. However, the band may have a mobility different than that expected as a result of modifications such as glycosylation, ubiquitination, or enzymatic cleavage.

Antibodies capable of specifically recognizing the expressed GlyT1 protein or a portion thereof can be prepared using standard methods and are described below.

If antibody production is not possible, the nucleic acids encoding the GlyT1 protein or a portion thereof may be incorporated into an expression vector designed for use in purification schemes employing chimeric polypeptides. In such strategies the nucleic acid encoding the GlyT1 protein or a portion thereof is inserted in frame with the gene encoding the other half of the chimera. The other half of the chimera is, e.g., beta-globin or a nickel binding polypeptide encoding sequence. A chromatography matrix having an antibody to beta-globin or nickel attached thereto is then used to purify the chimeric protein. Protease cleavage sites is engineered between the beta-globin gene or the nickel binding polypeptide and the GlyT1 protein or portion thereof. Thus, the two polypeptides of the chimera are separated from one another by protease digestion.

One useful expression vector for generating beta-globin chimeric proteins is pSG5 (Stratagene), which encodes rabbit beta-globin. Intron II of the rabbit beta-globin gene facilitates splicing of the expressed transcript, and the polyadenylation signal incorporated into the construct increases the level of expression. These techniques are well known to those skilled in the art of molecular biology. Standard methods are published in methods texts such as Davis et al. (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind GlyT1 Polypeptides of the Invention

Any GlyT1 polypeptide or whole protein may be used to generate antibodies capable of specifically binding to an expressed GlyT1 protein or fragment thereof as described.

In preferred embodiments, antibodies are prepared that specifically recognize any of the novel GlyT1 polypeptides of the invention (e.g. polypeptides comprising a sequence shown as SEQ ID NOs:26-33), or a polypeptide comprising a sequence encoded by any of the novel exons of the invention (SEQ ID NOs:2-9). For an antibody composition to specifically bind to a first variant of GlyT1, it must demonstrate at least a 5%, 10%, 15%, 20%, 25%, 50%, or 100% greater binding affinity for a full length first variant of the GlyT1 protein than for a full length second variant of the GlyT1 protein in an ELISA, RIA, or other antibody-based binding assay.

In a preferred embodiment, the invention concerns antibody compositions, either polyclonal or monoclonal, capable of selectively binding to an epitope-containing polypeptide comprising a contiguous span of at least 6 amino acids, preferably at least 8 to 10 amino acids, more preferably at least 12, 15, 20, 25, 30, 40, 50, or 100 amino acids of any of SEQ ID Nos:26-33, or encoded by SEQ ID NOs:2-9.

In a preferred embodiment, the invention concerns the use in the manufacture of antibodies of a polypeptide comprising a contiguous span of at least 6 amino acids, preferably at least 8 to 10 amino acids, more preferably at least 12, 15, 20, 25, 30, 40, 50, or 100 amino acids of any of SEQ ID NOs:26-33, or encoded by SEQ ID NOs:2-9.

Non-human animals or mammals, whether wild-type or transgenic, which express a different species of GlyT1 than the one to which antibody binding is desired, and animals which do not express GlyT1 (i.e. a GlyT1 knock out animal as described herein) are particularly useful for preparing antibodies. GlyT1 knock out animals will recognize all or most of the exposed regions of a GlyT1 protein as foreign antigens, and therefore produce antibodies with a wider array of GlyT1 epitopes. Moreover, smaller polypeptides with only 10 to 30 amino acids may be useful in obtaining specific binding to any one of the GlyT1 proteins. In addition, the humoral immune system of animals which produce a species of GlyT1 that resembles the antigenic sequence will preferentially recognize the differences between the animal's native GlyT1 species and the antigen sequence, and produce antibodies to these unique sites in the antigen sequence. Such a technique will be particularly useful in obtaining antibodies that specifically bind to any one of the GlyT1 proteins.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled using any of a large number of labels, including any one of the radioactive, fluorescent or enzymatic labels known in the art.

Consequently, the invention is also directed to a method for detecting specifically the presence of a GlyT1 polypeptide according to the invention in a biological sample, said method comprising bringing into contact the biological sample with a polyclonal or monoclonal antibody that specifically binds a GlyT1 polypeptide comprising an amino acid sequence of SEQ ID Nos:26-33, or encoded by any of the nucleic acid sequences shown as SEQ ID NOs:2-9 or 14-21; or to a peptide fragment or variant thereof; and detecting the antigen-antibody complex formed.

The invention also concerns a diagnostic kit for detecting in vitro the presence of a GlyT1 polypeptide according to the present invention in a biological sample, wherein said kit comprises a polyclonal or monoclonal antibody that specifically binds a GlyT1 polypeptide comprising an amino acid sequence of SEQ ID Nos:26-33, or encoded by any of the nucleic acid sequences shown as SEQ ID NOs:2-9 or 14-21; or to a peptide fragment or variant thereof, optionally labeled; and a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

Recombinant Vectors

The term "vector" is used herein to designate either a circular or a linear DNA or RNA molecule, which is either double-stranded or single-stranded, and which comprises at least one polynucleotide of interest that is sought to be transferred in a cell host or in a unicellular or multicellular host organism.

The present invention encompasses a family of recombinant vectors that comprise any regulatory or coding polynucleotide derived from any of the herein-provided novel GlyT1 cDNAs.

In a first preferred embodiment, a recombinant vector of the invention is used to amplify an inserted polynucleotide derived from a GlyT1 cDNA in a suitable cell host, this polynucleotide being amplified at every time that the recombinant vector replicates.

A second preferred embodiment of the recombinant vectors according to the invention comprises expression vectors comprising a regulatory polynucleotide and/or a coding nucleic acid of the invention. Within certain embodiments, expression vectors are employed to express the GlyT1 polypeptide which can then be purified and, for example, be used in ligand screening assays or as an immunogen in order to raise specific antibodies directed against the GlyT1 protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a GlyT1 protein, preferably a GlyT1 protein of any of the amino acid sequences of SEQ ID Nos:26-33, or variants or fragments thereof.

The invention also pertains to a recombinant expression vector useful for the expression of a GlyT1 coding sequence, wherein said vector comprises a nucleic acid of SEQ ID Nos:2-9 or 14-21.

Some of the elements which can be found in the vectors of the present invention are described in further detail elsewhere in the present specification.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene. Methods of making cells with altered expression, and polynucleotide constructs used to make the cells, are also provided.

Another method for altering the expression of a targeted gene, e.g. a GlyT1 gene, is by introducing into a cell capable of expressing GlyT1 a polynucleotide whose presence in the cell alters the expression of the GlyT1 gene. For example, the polynucleotide may act to replace the endogenous GlyT1 promoter with a more or less active promoter, or may comprise an enhancer element whose insertion into the genome in the vicinity of the GlyT1 gene results in an increase or decrease in the expression of the GlyT1.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles including Koller et al., (1989) Proc. Natl. Acad. Sci. USA 86:8932-8935.

1. General Features of the Expression Vectors of the Invention

Recombinant vectors that can be used in the present invention include, but are not limited to, YACs (Yeast Artificial Chromosome), BACs (Bacterial Artificial Chromosome), phages, phagemids, cosmids, plasmids, and linear DNA molecules which may comprise chromosomal, non-chromosomal, semi-synthetic or synthetic DNA. Such recombinant vectors can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation signal, splice donor and acceptor sites, transcriptional termination sequences, and 5'-flanking non-transcribed sequences. DNA sequences derived from the SV40 viral genome, for example SV40 origin, early promoter, enhancer, splice and polyadenylation signals may be used to provide the required non-transcribed genetic elements.

The in vivo expression of a GlyT1 polypeptide of SEQ ID Nos:26-33, or fragments or variants thereof, may be useful in order to correct a genetic defect related to the expression of the native gene in a host organism or to the production of a biologically inactive GlyT1 protein.

Consequently, the present invention also comprises recombinant expression vectors mainly designed for the in vivo production of a GlyT1 polypeptide of SEQ ID Nos: 26-33, or fragments or variants thereof, by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI LacZ, the T3 or 7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic egineering. For example, one may refer to Sambrook et al. (1989) or also to the procedures described by Fuller et al. (1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. Coli*, or levan saccharase for mycobacteria, this latter marker being a negative selection marker.

4. Preferred Vectors.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising GlyT1 nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising GlyT1 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 25.0 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of a GlyT1 polypeptide of SEQ ID Nos:26-33 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of the GlyT1 polypeptide of SEQ ID Nos:26-33 or fragments or variants thereof in a baculovirus expression system include those described by Chai et al. (1993), Vlasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application N° FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC N° VR-999), Friend (ATCC N° VR-245), Gross (ATCC N° VR-590), Rauscher (ATCC N° VR-998) and Moloney Murine Leukemia Virus (ATCC N° VR-190; PCT Application N° WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application N° WO 93/25234, PCT Application N° WO 94/06920, Roux et al. (1989), Julan et al. (1992) and Neda et al. (1991).

Yet another viral vector system that is contemplated by the invention comprises the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC vectors

The bacterial artificial chromosome (BAC) cloning system (Shizuya et al., 1992) has been developed to stably maintain large fragments of genomic DNA (100-300 kb) in E. coli. A preferred BAC vector comprises a pBeloBAC11 vector that has been described by Kim et al. (1996). BAC libraries are prepared with this vector using size-selected genomic DNA that has been partially digested using enzymes that permit ligation into either the Barn HI or HindIII sites in the vector. Flanking these cloning sites are 17 and SP6 RNA polymerase transcription initiation sites that can be used to generate end probes by either RNA transcription or PCR methods. After the construction of a BAC library in E. coli, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell (or cell extract capable of supporting protein expression). This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediated transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Universitéd'Ottawa) as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome using any of a wide variety of standard methods (see, e.g., Ghosh and Bacchawat, 1991; Wong et al., 1980; Nicolau et al., 1987).

In a specific embodiment, the invention provides a composition for the in vivo production of the GlyT1 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GlyT1 polypeptide or the desired fragment thereof is reintroduced into the animal body in order to deliver the recombinant protein within the body either locally or systemically.

Cell Hosts

Another object of the invention comprises a host cell that has been transformed or transfected with one of the polynucleotides described herein, and in particular a polynucleotide either comprising a GlyT1 regulatory polynucleotide or the coding sequence of the GlyT1 polypeptide selected from the group consisting of SEQ ID Nos:2-9 and 14-21, or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "Genomic Sequences Of The GlyT1 Gene" section, the "GlyT1 cDNA Sequences" section, the "Coding Regions" section, the "Polynucleotide constructs" section, and the "Oligonucleotide Probes And Primers" section.

An additional recombinant cell host according to the invention comprises any of the vectors described herein, more particularly any of the vectors described in the "Recombinant Vectors" section.

Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like *Pseudomonas, Streptomyces* and *Staphylocccus*.

b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N° CRL-1804), 3T3 (ATCC N° CRL-6361), CHO (ATCC N° CCL-61), human kidney 293. (ATCC N° 45504; N° CRL-1573) and BHK (ECACC N° 84100501; N° 84111301).

c) Other mammalian host cells.

The GlyT1 gene expression in mammalian, and typically human, cells may be inhibited or enhanced with the insertion of a GlyT1 genomic or cDNA sequence with the replacement of the GlyT1 gene counterpart in the genome of an animal cell by a GlyT1 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts-3 ng/µl —for P1 bacteriophage inserts—in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical break-age of this DNA, as described by Schedl et al. (1993b).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC n° CRL-1821), ES-D3 (ATCC n° CRL1934 and n° CRL-11632), YS001 (ATCC n° CRL-11776), 36.5 (ATCC n° CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein to designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention.

The transgenic animals of the invention all include within a plurality of their cells a cloned recombinant or synthetic DNA sequence, more specifically one of the purified or isolated nucleic acids comprising a GlyT1 coding sequence, a GlyT1 regulatory polynucleotide, a polynucleotide construct, or a DNA sequence encoding an antisense polynucleotide such as described in the present specification.

Generally, a transgenic animal according the present invention comprises any one of the polynucleotides, the recombinant vectors and the cell hosts described in the present invention. More particularly, the transgenic animals of the present invention can comprise any of the polynucleotides described in the "Genomic Sequences Of the GlyT1 Gene" section, the "GlyT1 cDNA Sequences" section, the "Coding Regions" section, the "Polynucleotide constructs" section, the "Oligonucleotide Probes And Primers" section, the "recombinant Vectors" section and the "Cell Hosts" section.

In a first preferred embodiment, these transgenic animals may be good experimental models in order to study the effects of GlyT1 activity, e.g. to study psychological disorders such as schizophrenia or other psychotic disorders. In one such embodiment, transgenic animals are produced in which one or several copies of a polynucleotide encoding any of the present novel GlyT1 proteins has been inserted into the genome.

In a second preferred embodiment, these transgenic animals may express a desired polypeptide of interest under the control of the regulatory polynucleotides of the GlyT1 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. Nos. 4,873,191; 5,464,764; or 5,789,215; these documents being herein incorporated by reference to disclose methods of producing transgenic mice.

Transgenic animals of the present invention are produced by the application of procedures which result in an animal with a genome that has incorporated exogenous genetic material. The procedure involves obtaining the genetic material, or a portion thereof, which encodes either a GlyT1 coding sequence, a GlyT1 regulatory polynucleotide or a DNA sequence encoding a GlyT1 antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention comprises recombinant host cells obtained from a transgenic animal described herein. In one embodiment the invention encompasses cells derived from non-human host mammals and animals comprising a recombinant vector of the invention or expressing any of the present novel GlyT1 polypeptides.

Recombinant cell lines may be established in vitro from cells obtained from any tissue of a transgenic animal according to the invention, for example by transfection of primary cell cultures with vectors expressing one-genes such as SV40 large T antigen, as described by Chou (1989) and Shay et al. (1991).

Methods for Screening Substances Interacting with a GlyT1 Polypeptide

For the purpose of the present invention, a ligand means a molecule, such as a protein, a peptide, an antibody or any synthetic chemical compound capable of binding to a GlyT1 protein or one of its fragments or variants or to modulate the expression of the polynucleotide coding for GlyT1 or a fragment or variant thereof.

In the ligand screening method according to the present invention, a biological sample or a defined molecule to be tested as a putative ligand of a GlyT1 protein is brought into contact with the corresponding purified GlyT1 protein, for example the corresponding purified recombinant GlyT1 protein produced by a recombinant cell host as described hereinbefore, in order to form a complex between this protein and the putative ligand molecule to be tested. In any of the herein-described assays, the GlyT1 may be present in a cell or cell membrane during the assay.

As an illustrative example, to study the interaction of any of the present novel GlyT1 proteins, or a fragment comprising a contiguous span of at least 6 amino acids, preferably at least 8 to 10 amino acids, more preferably at least 12, 15, 20, 25, 30, 40, 50, or 100 amino acids of SEQ ID NOs:26-33, or encoded by any of SEQ ID NOs:2-9 or 14-21, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with the GlyT1 protein, or a fragment comprising a contiguous span of at least 6 amino acids, preferably at least 8 to 10 amino acids, more preferably at least 12, 15, 20, 25, 30, 40, 50, or 100 amino acids of SEQ ID Nos:26-33, or encoded by any of SEQ ID NOs:2-9 or 14-21, may be identified using assays such as the following. The molecule to be tested for binding is labeled with a detectable label, such as a fluorescent, radioactive, or enzymatic tag and placed in contact with immobilized GlyT1 protein, or a fragment thereof under conditions which permit specific binding to occur. After removal of non-specifically bound molecules, bound molecules are detected using appropriate means.

Another object of the present invention comprises methods and kits for the screening of candidate substances that interact with a GlyT1 polypeptide.

The present invention pertains to methods for screening substances of interest that interact with a GlyT1 protein or one fragment or variant thereof. By their capacity to bind covalently or non-covalently to a GlyT1 protein or to a fragment or variant thereof, these substances or molecules may be advantageously used both in vitro and in vivo.

In vitro, said interacting molecules may be used as detection means in order to identify the presence of a GlyT1 protein in a sample, preferably a biological sample.

A method for the screening of a candidate substance comprises the following steps:

a) providing a polypeptide comprising, consisting essentially of, or consisting of a GlyT1 protein or a fragment comprising a contiguous span of at least 6 amino acids, preferably at least 8 to 10 amino acids, more preferably at least 12, 15, 20, 25, 30, 40, 50, or 100 amino acids of any of SEQ ID Nos:26-33, or encoded by any of SEQ ID NOs:2-9 or 14-21;

b) obtaining a candidate substance;

c) bringing into contact said polypeptide with said candidate substance;

d) detecting the complexes formed between said polypeptide and said candidate substance.

The invention further concerns a kit for the screening of a candidate substance interacting with the GlyT1 polypeptide, wherein said kit comprises:

a) a GlyT1 protein having an amino acid sequence selected from the group consisting of any of the amino acid sequences of SEQ ID Nos:26-33, or a peptide fragment comprising a contiguous span of at least 6 amino acids, preferably at least 8 to 10 amino acids, more preferably at least 12, 15, 20, 25, 30, 40, 50, or 100 amino acids of any of SEQ ID Nos:26-33, or an amino acid sequence encoded by any of SEQ ID NOs:2-9 or 14-21;

b) optionally means useful to detect the complex formed between the GlyT1 protein or a peptide fragment or a variant thereof and the candidate substance.

In a preferred embodiment of the kit described above, the detection means comprises a monoclonal or polyclonal antibodies directed against the GlyT1 protein or a peptide fragment or a variant thereof.

Various candidate substances or molecules can be assayed for interaction with a GlyT1 polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the herein-described screening methods. Preferably, such kits comprise a GlyT1 polypeptide or a fragment or a variant thereof, and optionally means useful to detect the complex formed between the GlyT1 polypeptide or its fragment or variant and the candidate substance. In a preferred embodiment the detection means comprise a monoclonal or polyclonal antibody directed against the corresponding GlyT1 polypeptide or a fragment or a variant thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Felici F. et al., 1991). According to this particular embodiment, the recombinant phage expressing a protein that binds to the immobilized GlyT1 protein is retained and the complex formed between the GlyT1 protein and the recombinant phage may be subsequently immunoprecipitated by a polyclonal or a monoclonal antibody directed against the GlyT1 protein.

Once the ligand library in recombinant phages has been constructed, the phage population is brought into contact with the immobilized GlyT1 protein. Then the preparation of complexes is washed in order to remove the non-specifically bound recombinant phages. The phages that bind specifically to the GlyT1 protein are then eluted by a buffer (acid pH) or immunoprecipitated by the monoclonal antibody produced by the hybridoma anti-GlyT1, and this phage population is subsequently amplified by an over-infection of bacteria (for example *E. coli*). The selection step may be repeated several times, preferably 2-4 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to the GlyT1 protein, or a fragment comprising a contiguous span of at least 6 amino acids, preferably at least 8 to 10 amino acids, more preferably at least 12, 15, 20, 25, 30, 40, 50, or 100 amino acids of any of SEQ ID NOs:26-33, or encoded by any of SEQ ID NOs:2-9 or 14-21, may be identified in competition experiments. In such assays, the GlyT1 protein, or a fragment thereof, is immobilized to a surface, such as a plastic plate. Increasing amounts of the peptides, drugs or small molecules are placed in contact with the immobilized GlyT1 protein, or a fragment thereof, in the presence of a detectable labeled known GlyT1 protein ligand. For example, the GlyT1 ligand may be detectably labeled with a fluorescent, radioactive, or enzymatic tag. The ability of the test molecule to bind the GlyT1 protein, or a fragment thereof, is determined by measuring the amount of detectably labeled known ligand bound in the presence of the test molecule. A decrease in the amount of known ligand bound to the GlyT1 protein, or a fragment thereof, when the test molecule is present indicated that the test molecule is able to bind to the GlyT1 protein, or a fragment thereof.

C. Candidate Ligands Obtained by Affinity Chromatography.

Proteins or other molecules interacting with the GlyT1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NOs:26-33, or encoded by any of SEQ ID NOs:2-9 or 14-21, can also be found using affinity columns which contain the GlyT1 protein, or a fragment thereof. The GlyT1 protein, or a fragment thereof, may be attached to the column using conventional techniques including chemical coupling to a suitable column matrix such as agarose, Affi Gel®, or other matrices familiar to those of skill in art. In some embodiments of this method, the affinity column contains chimeric proteins in which the GlyT1 protein, or a fragment thereof, is fused to glutathion S transferase (GST). A mixture of cellular proteins or pool of expressed proteins as described above is applied to the affinity column. Proteins or other molecules interacting with the GlyT1 protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with the GlyT1 protein, or a fragment comprising a contiguous span of at least 6 amino acids, preferably at least 8 to 10 amino acids, more preferably at least 12, 15, 20, 25, 30, 40, 50, or 100 amino acids of any of SEQ ID Nos:26-33, or encoded by any of SEQ ID NOs:2-9 or 14-21, can also be screened by using an Optical Biosensor as described in Edwards and Leatherbarrow (1997) and also in Szabo et al. (1995), the disclosures of which are incorporated herein by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the GlyT1 protein, or a fragment thereof, the GlyT1 protein, or a fragment thereof, is immobilized onto a surface. This surface comprises one side of a cell through which flows the candidate molecule to be assayed. The binding of the candidate molecule on the GlyT1 protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed GlyT1 protein at their surface.

The main advantage of the method is that it allows the determination of the association rate between the GlyT1 protein and molecules interacting with the GlyT1 protein. It is thus possible to select specifically ligand molecules interacting with the GlyT1 protein, or a fragment thereof, through strong or conversely weak association constants.

E. Candidate Ligands Obtained through a Two-Hybrid Screening Assay.

The yeast two-hybrid system is designed to study protein-protein interactions in vivo (Fields and Song, 1989), and relies upon the fusion of a bait protein to the DNA binding domain of the yeast Gal4 protein. This technique is also described in U.S. Pat. No. 5,667,973 and U.S. Pat. No. 5,283,173 (Fields et al.) the technical teachings of both patents being herein incorporated by reference.

The general procedure of library screening by the two-hybrid assay may be performed as described by Harper et al. (1993) or as described by Cho et al. (1998) or also Fromont-Racine et al. (1997).

The bait protein or polypeptide comprises, consists essentially of, or consists of a GlyT1 polypeptide or a fragment comprising a contiguous span of at least 6 amino acids, preferably at least 8 to 10 amino acids, more preferably at least 12, 15, 20, 25, 30, 40, 50, or 100 amino acids of any of SEQ ID NOs:26-33, or encoded by any of SEQ ID NOs:2-9 or 14-21.

More precisely, the nucleotide sequence encoding the GlyT1 polypeptide or a fragment or variant thereof is fused to a polynucleotide encoding the DNA binding domain of the GAL4 protein, the fused nucleotide sequence being inserted into a suitable expression vector, for example pAS2 or pM3.

Then, a human cDNA library is constructed in a specially designed vector, such that the human cDNA insert is fused to a nucleotide sequence in the vector that encodes the transcriptional domain of the GALA protein. Preferably, the vector used is the pACT vector. The polypeptides encoded by the nucleotide inserts of the human cDNA library are termed "prey" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the following:

Y190, the phenotype of which is (MATa, Leu2-3, 112 ura3-12, trp1-901, his3-D200, ade2-101, gal4Dgal180D URA3 GAL-LacZ, LYS GAL-1HIS3, cyh');

Y187, the phenotype of which is (MATa gal4gal80 his3 trp1-901 ade2-101 ura3-52 leu2-3,-112 URA3 GAL-lacZmef), which is the opposite mating type of Y190.

Briefly, 20 μg of pAS2/GlyT1 and 20 μg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of pAS2/GlyT1 plasmids bu retention of pACT-cDNA library plasmids. The resulting Y190 strains are mated with Y187 strains expressing GLYT1 or non-related control proteins; such as cyclophilin B, lamin, or SNF1, as Gal4 fusions as described by Harper et al. (1993) and by Bram et al. (Bram R J et al., 1993), and screened for beta galactosidase by filter lift assay. Yeast clones that are beta gal- after mating with the control Gal4 fusions are considered false positives.

In another embodiment of the two-hybrid method according to the invention, interaction between the GlyT1 or a fragment or variant thereof with cellular proteins may be assessed using the Matchmaker Two Hybrid System 2 (Catalog No. K1604-1, Clontech). As described in the manual aaccompanying the Matchmaker Two Hybrid System 2 (Catalog No. K1604-1, Clontech), the disclosure of which is incorporated herein by reference, nucleic acids encoding the GlyT1 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between GlyT1 and the protein or peptide encoded by the initially selected cDNA insert.

Methods for Identifying Modulators of GlyT1 Activity

Any of a large number of assays, agonists, and antagonists are known and can be used to assess the activity of any of the herein-described GlyT1 polypeptides. Assays include in vitro, ex vivo, and in vivo assays. For example, assays can be used in which the activity of the transporter is measured in cells (e.g. COS-7 cells, Xenopus oocytes, human embryonic kidney 293 cells) transfected with nucleic acids encoding the transporter, or using tissue homogenates or biological samples that contain cells naturally expressing the transporter (e.g. chondrocytes, placental choriocarcinoma cells, hippocampal pyramidal neurons), and using any of a large number of methods to assess transporter activity, including by detecting signal transduction molecule activity or levels, levels of transcription of genes responsive to transporter activity, etc. Compounds identified as a modulator of any of the GlyT1 polypeptides, and compounds found to physically interact with a GlyT1 polypeptide, have a large number of uses, including for the treatment of or prevention of a number of neurological and psychological disorders, e.g., disorders related to NMDA receptor signalling, such as schizophrenia.

The effect of a compound on GlyT1 activity can be assessed in any of a large number of ways, including, but not limited to, by examining glycine transport or uptake (e.g. using whole-cell patch-clamp recordings of hipposampal pyramidal neurons in vitro), synaptic transmission through vertebrate autonomic ganglia, postsynaptic nicotinic acetylcholine receptor (nAChRS) activity, N-methyl-D-aspartate receptor (NMDAR) function, any animal model for assessing NMDA receptor activity, e.g. using behavioral assays, or any other assay for assessing glycine transport in cells or in animals.

Examples of suitable ligands for use in the present assays, including agonists and antagonists, inhibitors or activators, include, but are not limited to, sarcosine (GlyT1 inhibitor), alpha-methylaminoisobutyric acid (MeAIB) (inhibitor of glycine transport), glycine methyl ester, glycine ethyl ester, 2-amino-5-phosphonovaleric acid (inhibitor of glycine transport), 7-chloro-kynurenic acid (inhibitor of glycine transport), doxepin, amitriptyline, N[3-(4'-fluorophenyl-3-4'-phenylphenoxy)propyl]sarcosine (NFPS; inhibitor), nortriptyline, as well as any compound structurally related to any of these compounds, or any other compound that interacts with or modulates any of the presently described glycine transporters. Such compounds can either be used as positive or negative controls in the herein-described assays, or can be included in the assay, as the test compound is assessed for its ability to modulate the known effect of a ligand on the transporter. These compounds having known activity on GlyT1 transporters can also preferably be used as "lead compounds" to identify related compounds with potentially enhanced properties, e.g. in terms of activity or absence of side effects.

As described above, the ability of a compound to alter the binding of a known ligand (e.g. glycine), to any of the herein-described glycine transporter, in vitro, in vivo, or ex vivo, can also be used.

Methods of assaying glycine transporter activity, and glycine transporter interacting ligands, are described in, inter alia, Horiuchi et al. (2001) PNAS 98(4):1448-53; Tsen et al. (2000) Nat Neurosci 3(2):126-32; Evans et al. (1999) FEBS Lett 463(3):301-6; Barker et al. (1999) J Physiol 514 (Pt 3):795-808; Liu et al. (1994) Biochim Biophys Acta 1194 (1):176-84; Kim et al. (1994) Mol Pharmacol 45(4):608-17; Liu et al. (1992) FEBS Lett 305(2):110-4; Bergeron et al. (1998) Proc Natl Acad Sci U S A 95(26):15730-4; Nunez et al. (2000) Br J Pharmacol 129(1):200-6; the entire disclosure of each of which is herein incorporated by reference.

Methods for Inhibiting the Expression of a GlyT1 cDNA

Other therapeutic compositions according to the present invention comprise advantageously an oligonucleotide fragment of the nucleic acid sequence of GlyT1 as an antisense tool to inhibit the expression of the corresponding GlyT1 cDNA.

Preferred methods using antisense polynucleotide according to the present invention are the procedures described by Sczakiel et al. (1995).

Preferably, the antisense tools are chosen among the polynucleotides (15-200 bp long) that are complementary to the 5' end of the GlyT1 mRNA of interest. In another embodiment, a combination of different antisense polynucleotides complementary to different parts of the desired targeted gene are used.

Preferred antisense polynucleotides according to the present invention are complementary to a sequence of the mRNAs of GlyT1 that contains either the translation initiation codon ATG or a splicing donor or acceptor site.

The antisense nucleic acids should have a length and melting temperature sufficient to permit formation of an intracellular duplex having sufficient stability to inhibit the expression of the GlyT1 mRNA in the duplex. Strategies for designing antisense nucleic acids suitable for use in gene therapy are disclosed in Green et al. (1986) and Izant and Weintraub (1984), the disclosures of which are incorporated herein by reference.

In some strategies, antisense molecules are obtained by reversing the orientation of the GlyT1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of GlyT1 antisense nucleic acids in vivo by operably linking DNA containing the antisense sequence to a promoter in a suitable expression vector.

Alternatively, suitable antisense strategies are those described by Rossi et al. (1991), in International Application Nos. WO 94/23026, WO 95/04141, WO 92/18522 and in European Patent Application No. EP 0 572 287 A2.

An alternative to the antisense technology that is used according to the present invention comprises using ribozymes that will bind to a target sequence via their complementary polynucleotide tail and that will cleave the corresponding RNA by hydrolyzing its target site (e.g., "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

Treatment of Neurological and Psychiatric Disorders

The present GlyT1 polypeptides, polynucleotides, and modulators thereof, can be used to treat or prevent any of a large number of diseases or conditions. For example, any disease, disorder, or condition associated with an elevated or reduced level of glycine or glycine transporter activity can be treated or prevented by modulating the activity or expression of any of the herein-described polypeptides.

In one, preferred embodiment, any of the present polypeptides, polynucleotides, or modulators is used to treat or prevent a condition associated with abnormal NMDA receptor activity.

NMDA receptors have been implicated in a large number of neurological and psychological functions, including memory and learning. For example, as decreased function of NMDA-mediated neurotransmission has been suggested to contribute to the symptoms of schizophrenia (Olney and Farber, Archives General Psychiatry 52: 998-1007 (1996), agents that inhibit GlyT1 transporters (and thus increase glycine activation of NMDA receptors), can be used to treat schizophrenia or other psychotic conditions. Such inhibitors can also be used to treat dementia-associated disorders, as well as other conditions such as attention deficit disorders and organic brain syndromes. In addition, activators of the transporters (which cause decreased glycine-activation of NMDA receptors) can be used to treat neuronal death associated with stroke or head trauma, as well as neurodegenerative diseases such as Alzheimer's disease, multiinfarct dementia, AIDS dementia, Parkinson's disease, Huntington's disease, or amyotrophic lateral sclerosis.

Pharmaceutical and Physiologically Acceptable Compositions and Administration Thereof To treat or present any of the herein-described disorders using any of the compounds described herein, the compounds may be prepared utilizing readily available starting materials and employing common synthetic methodologies well-known to those skilled in the art.

The effective dose of the compound can vary, depending upon factors such as the condition of the patient, the severity of the symptoms of the disorder, and the manner in which the pharmaceutical composition is administered. For human patients, the effective dose of typical compounds generally requires administering the compound in an amount of at least about 1, often at least about 10, and frequently at least about 25 mg/24 hr./patient For human patients, the effective dose of typical compounds requires administering the compound which generally does not exceed about 500, often does not exceed about 400, and frequently does not exceed about 300 mg/24 hr./patient. In addition, administration of the effective dose is such that the concentration of the compound within the plasma of the patient normally does not exceed 500 ng/ml, and frequently does not exceed 100 ng/ml.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is sufficient. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art. One preferred dosage is about 10 mg to about 70 mg per day. In choosing a regimen for patients suffering from psychotic illness it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds useful according to the method of the present invention have the ability to pass across the blood-brain barrier of the patient. As such, such compounds have the ability to enter the central nervous system of the patient The log P values of typical compounds useful in carrying out the present invention generally are greater than 0, often are greater than about 1, and frequently are greater than about 1.5. The log P values of such typical compounds generally are less than about 4, often are less than about 3.5, and frequently are less than about 3. Log P values provide a measure of the ability of a compound to pass across a diffusion barrier, such as a biological membrane. See, Hansch, et al., J. Med. Chem., Vol. 11, p. 1(1968). Alternatively, the compositions of the present invention can bypass the blood brain barrier through the use of compositions and methods known in the art for bypassing the blood brain barrier (e.g., U.S. Pat. Nos. 5,686,416; 5,994,392, incorporated by reference in their entireties) or can be injected directly into the brain. Suitable areas include the cerebral cortex, cerebellum, midbrain, brainstem, hypothalamus, spinal cord and ventricular tissue, and areas of the PNS including the carotid body and the adrenal medulla. The compositions can be administered in as a bolus or through the use of other methods such as an osmotic pump.

The compounds of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one customary inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like. Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like. Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservative, buffers, or propellants as may be required. Ophthalmic formulations, eye ointments, powders, and solutions are also contemplated as being within the scope of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Aqueous suspensions contain the active materials in admixture with excipients suitable for the manufacture of aqueous suspensions. Such excipients are suspending agents, for example sodium carboxymethylcellulose, methylrlcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin. Oily suspensions may be formulated by suspending the active ingredients in a vegetable oil, for example arachis oil olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monolcate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Computer-Related Embodiments

As used herein the term "nucleic acid codes of the invention" encompass the nucleotide sequences comprising, consisting essentially of, or consisting of any one of the following: a) a contiguous span of at least 12, 15, 18, 20, 25, 30, 35, 40, 50, 60, 70, 80, 90, 100, 150, 200, 500, or 1000 nucleotides of SEQ ID NO:1, wherein said contiguous span comprises at least 1, 2, 3, 5, or 10 of the following nucleotide positions of any of SEQ ID NOs:2-9; b) a contiguous span of at least 12, 15, 18, 20, 25, 30, 35, 40, 50, 60, 70, 80, 90, 100, 150, 200, 500, 1000 nucleotides of any of SEQ ID NOs:2-9, or the full-length sequence thereof; c) a contiguous span of at least 12, 15, 18, 20, 25, 30, 35, 40, 50, 60, 70, 80, 90, 100, 150, 200, 500, or 1000 nucleotides of any of SEQ ID NOs:14-21, or the full-length sequence thereof; and, d) a nucleotide sequence complementary to any one of the preceding nucleotide sequences. The "nucleic acid codes of the invention" further encompass nucleotide sequences homologous to any of the above-described sequences. Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, $3^{rd}$ edition. W. H Freeman & Co., New York.) or in any other format or code which records the identity of the nucleotides in a sequence.

As used herein the term "polypeptide codes of the invention" encompass the polypeptide sequences comprising a contiguous span of at least 6, 8, 10, 12, 15, 20, 25, 30, 40, 50, 100 or more amino acids of any of SEQ ID NOs:26-33, or a sequence encoded by any of SEQ ID NOs:2-9 or 14-21. It will be appreciated that the polypeptide codes of the invention can be represented in the traditional single character format or three letter format (See the inside back cover of Stryer, Lubert, Biochemistry, 3rd edition. W. H Freeman & Co., New York.) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disk, a floppy disk a magnetic tape, CD-ROM, Digital Versatile Disk (DVD), Random Access Memory (RAM), or Read Only Memory (ROM) as well as other types of other media known to those skilled in the art.

Embodiments of the present invention include systems, particularly computer systems which store and manipulate the sequence information described herein. As used herein, "a computer system" refers to the hardware components, software components, and data storage components used to analyze the nucleotide sequences of the nucleic acid codes of the invention or the amino acid sequences of the polypeptide codes of the invention. In one embodiment, the computer system is a Sun Enterprise 1000 server (Sun Micro-systems, Palo Alto, Calif.). The computer system preferably includes a processor for processing, accessing and manipulating the sequence data. The processor can be any well-known type of central processing unit, such as the Pentium m from Intel Corporation, or similar processor from Sun, Motorola, Compaq or International Business Machines.

Preferably, the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory (preferably implemented as RAM) and one or more internal data storage devices, such as a hard drive and/or other computer readable media having data recorded thereon. In some embodiments, the computer system further includes one or more data retrieving devices for reading the data stored on the internal data storage devices.

The data retrieving device may represent, for example, a floppy disk drive, a compact disk drive, a magnetic tape drive, etc. In some embodiments, the internal data storage device is a removable computer readable medium such as a floppy disk, a compact disk a magnetic tape, etc. containing control logic and/or data recorded thereon. The computer system may advantageously include or be programmed by appropriate software for reading the control logic and/or the data from the data storage component once inserted in the data retrieving device.

The computer system includes a display which is used to display output to a computer user. It should also be noted that the computer system can be linked to other computer systems in a network or wide area network to provide centralized access to the computer system.

Software for accessing and processing the nucleotide sequences of the nucleic acid codes of the invention or the amino acid sequences of the polypeptide codes of the invention (such as search tools, compare tools, and modeling tools etc.) may reside in main memory during execution.

In some embodiments, the computer system may further comprise a sequence comparer for comparing the above-described nucleic acid codes of the invention or the polypeptide codes of the invention stored on a computer readable medium to reference nucleotide or polypeptide sequences stored on a computer readable medium. A "sequence comparer" refers to one or more programs which are implemented on the computer system to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

In one embodiment, a process is used for comparing a new nucleotide or protein sequence with a database of sequences in order to determine the homology levels between the new sequence and the sequences in the database. The database of sequences can be a private database stored within the computer system, or a public database such as GENBANK, PIR OR SWISSPROT that is available through the Internet.

The process begins at a start state and then moves to a state wherein the new sequence to be compared is stored to a memory in a computer system. As discussed above, the memory could be any type of memory, including RAM or an internal storage device.

The process then moves to a state wherein a database of sequences is opened for analysis and comparison. The process then moves to a state wherein the first sequence stored in the database is read into a memory on the computer. A comparison is then performed to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed, a determination is made at a decision state whether the two sequences are the same. Of course, the term "same" is not limited to sequences that are absolutely identical. Sequences that are within the homology parameters entered by the user will be marked as "same" in the process.

If a determination is made that the two sequences are the same, the process moves to a state wherein the name of the sequence from the database is displayed to the user. This state notifies the user that the sequence with the displayed name fulfills the homology constraints that were entered. Once the name of the stored sequence is displayed to the user, the process moves to a decision state wherein a determination is made whether more sequences exist in the database. If no more sequences exist in the database, then the process terminates at an end state. However, if more sequences do exist in the database, then the process moves to a state wherein a pointer is moved to the next sequence in the database so that it can be compared to the new sequence. In this manner, the new sequence is aligned and compared with every sequence in the database.

It should be noted that if a determination had been made at the decision state that the sequences were not homologous, then the process would move immediately to the decision state in order to determine if any other sequences were available in the database for comparison.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify motifs implicated in biological function and structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be-implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

In another embodiment, a process is carried out in a computer for determining whether two sequences are homologous. The process begins at a start state and then moves to a state wherein a first sequence to be compared is stored to a memory. The second sequence to be compared is then stored in a memory. The process then moves to a state wherein the first character in the first sequence is read and then to a state wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state whether the two characters are the same. If they are the same, then the process moves to a state wherein the next characters in the first and second sequences are read. A determination is then made whether the next characters are the same. If they are, then the process continues this loop until two characters are not the same. If a determination is made that the next two characters are not the same, the process moves to a decision state to determine whether there are any more characters either sequence to read.

If there are no more characters to read, then the process moves to a state wherein the level of homology between the first and second sequences is displayed to the user. The level of homology is determined by calculating the proportion of characters between the sequences that were the same out of the total number of sequences in the first sequence. Thus, if every character in a first nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method described supra. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

In another embodiment, an identifier process is used to detect the presence of a feature in a sequence. The process begins at a start state and then moves to a state wherein a first sequence that is to be checked for features is stored to a memory in the computer system. The process then moves to a state wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com).

Once the database of features is opened, the process moves to a state wherein the first feature is read from the database. A comparison of the attribute of the first feature with the first sequence is then made. A determination is then made at a decision state whether the attribute of the feature was found in the first sequence. If the attribute was found, then the process moves to a state wherein the name of the found feature is displayed to the user.

The process then moves to a decision state wherein a determination is made whether more features exist in the database. If no more features do exist, then the process terminates at an end state. However, if more features do exist in the database, then the process reads the next sequence feature and loops back to the state wherein the attribute of the next feature is compared against the first sequence.

It should be noted, that if the feature attribute is not found in the first sequence at the decision state, the process moves directly to the decision state in order to determine if any more features exist in the database.

In another embodiment, the identifier may comprise a molecular modeling program which determines the 3-dimensional structure of the polypeptides codes of the invention. In some embodiments, the molecular modeling program identifies target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of the polypeptide codes of the invention. (See e.g., U.S. Pat. No. 5,557,535). Conventional homology modeling techniques have been used routinely to build models of proteases and antibodies. (Sowdhamini et al., (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., (1997)).

The results of the molecular modeling analysis may then be used in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, 1990), FASTA (Pearson and Lipman, 1988), FASTDB (Brutlag et al., 1990), Catalyst Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/ Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Throughout this application, various publications, patents and published patent applications are cited. The disclosures of these publications, patents and published patent specification referenced in this application are hereby incorporated by reference into the present disclosure to more fully describe the state of the art to which this invention pertains.

EXAMPLES

Example 1

DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells pellet) were collected after centrifugation for 10 minutes at 2000 rpm. Red cells were lysed by a lysis solution (50 ml final volume: 10 mM Tris pH7.6; 5 mM MgCl2; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0 4 M
200 µl SDS 10%
500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Amplification of Genomic DNA by PCR

The amplification of specific genomic sequences of the DNA samples of example 1 was carried out on the pool of DNA obtained previously. In addition, 50 individual samples were similarly amplified.

PCR assays were performed using the following protocol:

| Final volume | 25 µl |
| --- | --- |
| DNA | 2 ng/µl |
| MgCl2 | 2 mM |
| dNTP (each) | 200 µM |

-continued

| primer (each) | 2.9 ng/µl |
| --- | --- |
| Ampli Taq Gold DNA polymerase | 0.05 unit/µl |
| PCR buffer (10× = 0.1 M TrisHCl pH8.3 0.5M KCl) | 1× |

Each pair of first primers was designed using the sequence information of the GLYT1 gene disclosed herein and the OSP software (Hillier & Green, 1991). This first pair of primers was about 20 nucleotides in length and had the sequences shown as SEQ ID NOs:36 and 37.

"Primers PU contain the following additional PU 5' sequence: TGTAAAACGACGGCCAGT (SEQ ID NO:36); primers RP contain the following RP 5' sequence: CAG-GAAACAGCTATGACC (SEQ ID NO:37)."

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed Each cycle comprised: 30 sec at 95° C., 54° C. for 1 min, and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

In addition, RT-PCR was used to identify novel cDNAs present in the cells of normal and/or schizophrenic individuals. 8 novel splice variants were identified, and are shown as SEQ ID NOs:14-21 (nucleotide sequences) and SEQ ID NOs: 26-33 (polypeptide sequences) and diagrammed in FIG. 1. Certain of the novel variants include novel exons, which are presented herein as SEQ ID NOs:2-9.

Example 3

Identification of Biallelic Markers—Sequencing of Amplified Genomic DNA

The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

Example 4

Preparation of Antibody Compositions to the GlyT1 Protein

Substantially pure protein or polypeptide is isolated from transfected or transformed cells containing an expression vector encoding the GlyT1 protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the GlyT1 protein or a portion thereof can be prepared from murine hybridomas according to the classical method of Kohler, G. and Milstein, C., (1975) or derivative methods thereof. See, also, Harlow and Lane (1988).

Briefly, a mouse is repetitively inoculated with a few micrograms of the GlyT1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York Section 21-2.

B. Polyclonal Antibody Production by Immunization

Polyclonal antiserum containing antibodies to heterogeneous epitopes in the GLYT1 protein or a portion thereof can be prepared by immunizing suitable non-human animal with the GlyT1 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for GlyT1 concentration can be used to generate antibodies. Such proteins, fragments or preparations are introduced into the non-human mammal in the presence of an appropriate adjuvant (e.g. aluminum hydroxide, RIBI etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 □M). Affinity of the antisera for the antigen is determined by preparing competitive binding curves, as described, for example, by Fisher, D., (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

While the preferred embodiments of the invention has been illustrated and described, it will be appreciated that various changes can be made therein by the one skilled in the art without departing from the spirit and scope of the invention.

REFERENCES

Abbondanzo S J et al., 1993, Methods in Enzymology, Academic Press, New York pp 803-823
Ajioka R. S. et al., *Am. J. Hum. Genet.,* 60:1439-1447, 1997
Altschul et al., 1990, J. Mol. Biol. 215(3):403-410
Altschul et al., 1993, Nature Genetics 3:266-272
Altschul et al., 1997, Nuc. Acids Res. 25:3389-3402
Anton M. et al., 1995, J. Virol., 69: 4600-4606
Araki K et al. (1995) *Proc. Natl. Acad. Sci. USA.* 92(1): 160-4.
Aszódi et al., Proteins: Structure, Function, and Genetics, Supplement 1:38-42 (1997)
Ausubel et al. (1989) Current Protocols in Molecular Biology, Green Publishing Associates and Wiley Interscience, N.Y.
Baubonis W. (1993) *Nucleic Acids Res.* 21(9):2025-9.
Beaucage et al., *Tetrahedron Lett* 1981, 22: 1859-1862
Bradley A., 1987, Production and analysis of chimaeric mice. In: E. J. Robertson (Ed.), Teratocarcinomas and embryonic stem cells: A practical approach. IRL Press, Oxford, pp. 113.
Bram R J et al., 1993, Mol. Cell Biol., 13: 4760-4769
Brown E L, Belagaje R, Ryan M J, Khorana H G, *Methods Enzymol* 1979;68:109-151
Brutlag et al. Comp. App. Biosci. 6:237-245, 1990
Bush et al., 1997, J. Chromatogr., 777: 311-328.
Chai H. et al. (1993) *Biotechnol Appl. Biochem.* 18:259-273.
Chee et al. (1996) *Science.* 274:610-614.
Chen and Kwok *Nucleic Acids Research* 25:347-353 1997
Chen et al. (1987) *Mol. Cell. Biol.* 7:2745-2752.
Chen et al. *Proc. Natl. Acad. Sci. USA* 94/20 10756-10761, 1997
Cho R J et al., 1998, Proc. Natl. Acad. Sci. USA, 95(7): 3752-3757.
Chou J. Y., 1989, Mol. Endocrinol., 3: 1511-1514.
Clark A. G. (1990) *Mol. Biol. Evol.* 7:111-122.
Coles R, Caswell R, Rubinsztein D C, *Hum Mol Genet* 1998;7:791-800
Compton J. (1991) *Nature.* 350(6313):91-92.
Davis L. G., M. D. Dibner, and J. F. Battey, Basic Methods in Molecular Biology, ed., Elsevier Press, NY, 1986
Dempster et al., (1977) *J. R. Stat. Soc.,* 39B:1-38.
Dent D S & Latchman D S (1993) The DNA mobility shift assay. In: *Transcription Factors: A Practical Approach* (Latchman D S, ed.) pp1-26. Oxford: IRL Press
Eckner R. et al. (1991) *EMBO J.* 10:3513-3522.
Edwards et Leatherbarrow, *Analytical Biochemistry,* 246, 1-6 (1997)
Engvall, E., Meth. Enzymol. 70:419 (1980)
Excoffier L. and Slatkin M. (1995) *Mol. Biol. Evol.,* 12(5): 921-927.

Feldman and Steg, 1996, Medecine/Sciences, synthese, 12:47-55
Felici F., 1991, J. Mol. Biol., Vol. 222:301-310
Fields and Song, 1989, Nature, 340: 245-246
Fisher, D., Chap. 42 in: Manual of Clinical Immunology, 2d Ed. Rose and Friedman, Eds.) Amer. Soc. For Microbiol., Washington, D.C. (1980)
Flotte et al. (1992) *Am. J. Respir. Cell Mol. Biol.* 7:349-356.
Fodor et al. (1991) *Science* 251:767-777.
Fraley et al. (1979) *Proc. Natl. Acad. Sci. USA.* 76:3348-3352.
Fried M, Crothers D M, *Nucleic Acids Res* 1981;9:6505-6525
Fromont-Racine M. et al., 1997, Nature Genetics, 16(3): 277-282.
Fuller S. A. et al. (1996) *Immunology in Current Protocols in Molecular Biology*, Ausubel et al. Eds, John Wiley & Sons, Inc., USA.
Furth P. A. et al. (1994) *Proc. Natl. Acad. Sci USA.* 91:9302-9306.
Garner M M, Revzin A, *Nucleic Acids Res* 1981;9:3047-3060
Geysen H. Mario et al. 1984. Proc. Natl. Acad. Sci. U.S.A 81:3998-4002
Ghosh and Bacchawat, 1991, *Targeting of liposoines to hepatocytes*, IN: *Liver Diseases, Targeted diagnosis and therapy using specific receptors and ligands.* Wu et al. Eds., Marcel Dekeker, New York, pp. 87-104.
Gonnet et al., 1992, Science 256:1443-1445
Gopal (1985) *Mol. Cell. Biol.,* 5:1188-1190.
Gossen M. et al. (1992) *Proc. Natl. Acad. Sci. USA.* 89:5547-5551.
Gossen M. et al. (1995) *Science.* 268:1766-1769.
Graham et al. (1973) *Virology* 52:456-457.
Green et al., *Ann. Rev. Biochem.* 55:569-597 (1986)
Griffin et al. *Science* 245:967-971 (1989)
Grompe, M. (1993) *Nature Genetics.* 5:111-117.
Grompe, M. et al. (1989) *Proc. Natl. Acad. Sci. U.S.A.* 86:5855-5892.
Gu H. et al. (1993) *Cell* 73:1155-1164.
Gu H. et al. (1994) *Science* 265:103-106.
Guatelli J C et al. *Proc. Natl. Acad. Sci. USA.* 35:273-286.
Hacia J G, Brody L C, Chee M S, Fodor S P, Collins F S, *Nat Genet* 1996;14(4):441-447
Hall L. A. and Smirnov I. P. (1997) *Genome Research,* 7:378-388.
Hames B. D. and Higgins S. J. (1985) *Nucleic Acid Hybridization: A Practical Approach.* Hames and Higgins Ed., IRL Press, Oxford.
Harju L, Weber T, Alexandrova L, Lukin M, Ranki M, Jalanko A, *Clin Chem* 1993;39(11pt 1):2282-2287
Harland et al. (1985) *J. Cell. Biol.* 101:1094-1095.
Harlow, E., and D. Lane. 1988. Antibodies A Laboratory Manual. Cold Spring Harbor Laboratory. pp. 53-242
Harper J W et al., 1993, Cell, 75: 805-816
Hawley M. E. et al. (1994) *Am. J. Phys. Anthropol.* 18:104.
Henikoff and Henikoff, 1993, Proteins 17:49-61
Higgins et al., 1996, Methods Enzymol. 266:383-402
Hillier L. and Green P. *Methods Appl.,* 1991, 1: 124-8.
Hoess et al. (1986) *Nucleic Acids Res.* 14:2287-2300.
Huang L. et al. (1996) *Cancer Res* 56(5):1137-1141.
Huygen et al. (1996) *Nature Medicine.* 2(8):893-898.
Izant J G, Weintraub H, *Cell* 1984 April; 36(4):1007-15
Julan et al. (1992) *J. Gen. Virol.* 73:3251-3255.
Kanegae Y. et al., *Nucl. Acids Res.* 23:3816-3821(1995).
Karlin and Altschul, 1990, Proc. Natl. Acad. Sci. USA 87:2267-2268

Khoury J. et al., *Fundamentals of Genetic Epidemiology,* Oxford University Press, NY, 1993
Kim U-J. et al. (1996) *Genomics* 34:213-218.
Klein et al. (1987) *Nature.* 327:70-73.
Kohler, G. and Milstein, C., Nature 256:495 (1975)
Koller et al. (1992) *Annu. Rev. Immunol.* 10:705-730.
Kozal M J, Shah N, Shen N, Yang R, Fucini R, Merigan T C, Richman D D, Morris D, Hubbell E, Chee M, Gingeras T R, Nat Med 1996;2(7):753-759
Lander and Schork, *Science,* 265, 2037-2048, 1994
Landegren U. et al. (1998) *Genome Research,* 8:769-776.
Lange K. (1997) *Mathematical and Statistical Methods for Genetic Analysis.* Springer, New York.
Lenhard T. et al. (1996) *Gene.* 169:187-190.
Linton M. F. et al. (1993) *J. Clin. Invest.* 92:3029-3037.
Liu Z. et al. (1994) *Proc. Natl. Acad. Sci. USA.* 91:4528-4262.
Livak et al., *Nature Genetics,* 9:341-342, 1995
Livak K J, Hainer J W, *Hum Mutat* 1994;3(4):379-385
Lockhart et al. *Nature Biotechnology* 14: 1675-1680, 1996
Lucas A. H., 1994, In: Development and Clinical Uses of Haempophilus b Conjugate;
Mansour S. L. et al. (1988) *Nature.* 336:348-352.
Marshall R. L. et al. (1994) *PCR Methods and Applications.* 4:80-84.
McCormick et al. (1994) *Genet. Anal. Tech. Appl.* 11:158-164.
McLaughlin B. A. et al. (1996) *Am. J. Hum. Genet.* 59:561-569.
Morton N. E., *Am. J. Hum. Genet.,* 7:277-318, 1955
Muzyczka et al. (1992) *Curr. Topics in Micro. and Immunol.* 158:97-129.
Nada S. et al. (1993) *Cell* 73:1125-1135.
Nagy A. et al., 1993, Proc. Natl. Acad. Sci. USA, 90: 8424-8428.
Narang S A, Hsiung H M, Brousseau R, *Methods Enzymol* 1979;68:90-98
Neda et al. (1991) *J. Biol. Chem.* 266:14143-14146.
Newton et al. (1989) *Nucleic Acids Res.* 17:2503-2516.
Nickerson D. A. et al. (1990) *Proc. Natl. Acad. Sci. U.S.A.* 87:8923-8927.
Nicolau C. et al., 1987, *Methods Enzymol.,* 149:157-76.
Nicolau et al. (1982) *Biochim. Biophys. Acta.* 721:185-190.
Nyren P, Pettersson B, Uhlen M, *Anal Biochem* 1993;208 (1):171-175
O'Reilly et al. (1992) *Baculovirus Expression Vectors: A Laboratory Manual.* W. H. Freeman and Co., New York.
Ohno et al. (1994) *Science.* 265:781-784.
Oldenburg K. R. et al., 1992, *Proc. Natl. Acad. Sci.,* 89:5393-5397.
Orita et al. (1989) *Proc. Natl. Acad. Sci. U.S.A.*86:2776-2770.
Ott J., *Analysis of Human Genetic Linkage, John Hopkins University Press, Baltimore,* 1991
Ouchterlony, O. et al., Chap. 19 in: Handbook of Experimental Immunology D. Wier (ed) Blackwell (1973)
Parmley and Smith, Gene, 1988, 73:305-318
Pastinen et al., *Genome Research* 1997; 7:606-614
Pearson and Lipman, 1988, Proc. Natl. Acad. Sci. USA 85(8):2444-2448
Pease S. ans William R. S., 1990, Exp. Cell. Res., 190: 209-211.
Perlin et al. (1994) *Am. J. Hum. Genet.* 55:777-787.
Peterson et al., 1993, Proc. Natl. Acad. Sci. USA, 90:7593-7597.
Pietu et al. *Genome Research* 6:492-503, 1996

Potter et al. (1984) *Proc. Natl. Acad. Sci. U.S.A.* 81(22): 7161-7165.
Ramunsen et al., 1997, Electrophoresis, 18: 588-598.
Reid L. H. et al. (1990) *Proc. Nat. Acad. Sci. U.S.A.* 87:4299-4303.
Risch, N. and Merikangas, K. (*Science,* 273:1516-1517, 1996
Robertson E., 1987, Embryo-derived stem cell lines. In: E. J. Robertson Ed. *Teratocarcinomas and embrionic stem cells: a practical approach.* IRL Press, Oxford, pp. 71.
Rossi et al., *Pharmacol. Ther.* 50:245-254, (1991)
Roth J. A. et al. (1996) *Nature Medicine.* 2(9):985-991.
Roux et al. (1989) *Proc. Natl. Acad. Sci. U.S.A.* 86:9079-9083.
Ruano et al. (1990)*Proc. Natl. Acad. Sci. U.S.A.* 87:6296-6300.
Sambrook, J., Fritsch, E. F., and T. Maniatis. (1989) *Molecular Cloning: A Laboratory Manual.* 2ed. Cold Spring Harbor Laboratory, Cold Spring Harbor, N.Y.
Samson M, et al. (1996) *Nature,* 382(6593):722-725.
Samulski et al. (1989) *J. Virol.* 63:3822-3828.
Sanchez-Pescador R. (1988) *J. Clin. Microbiol.* 26(10): 1934-1938.
Sarkar, G. and Sommer S. S. (1991) *Biotechniques.*
Sauer B. et al. (1988) *Proc. Natl. Acad. Sci. U.S.A.* 85:5166-5170.
Schaid D. J. et al., *Genet. Epidemiol.,*13:423-450, 1996
Schedl A. et al., 1993a, Nature, 362: 258-261.
Schedl et al., 1993b, Nucleic Acids Res., 21: 4783-4787.
Schena et al. *Science* 270:467-470, 1995
Schena et al., 1996, Proc Natl Acad Sci USA,. 93(20): 10614-10619.
Schneider et al. (1997) *Arlequin: A Software For Population Genetics Data Analysis.* University of Geneva.
Schwartz and Dayhoff, eds., 1978, Matrices for Detecting Distance Relationships: Atlas of Protein Sequence and Structure, Washington: National Biomedical Research Foundation
Sczakiel G. et al. (1995) *Trends Microbiol.* 3(6):213-217.
Shay J. W. et al., 1991*, Biochem. Biophys. Acta,* 1072: 1-7.
Sheffield, V. C. et al. (1991) *Proc. Natl. Acad. Sci. U.S.A.* 49:699-706.
Shizuya et al. (1992) *Proc. Natl. Acad. Sci. U.S.A.* 89:8794-8797.
Shoemaker D D, et al., *Nat Genet* 1996;14(4):450-456
Smith (1957) *Ann. Hum. Genet.* 21:254-276.
Smith et al. (1983) *Mol. Cell. Biol.* 3:2156-2165.
Sosnowski R G, et al., *Proc Natl Acad Sci USA* 1997;94: 1119-1123
Sowdhamini et al., Protein Engineering 10:207, 215 (1997)
Spielmann S. and Ewens W. J., *Am. J. Hum. Genet.,* 62:450-458, 1998
Spielmann S. et al., *Am. J. Hum. Genet.,* 52:506-516, 1993
Sternberg N. L. (1992) Trends Genet. 8:1-16.
Sternberg N. L. (1994) *Mamm. Genome.* 5:397-404.
Stryer, L., *Biochemistry,* 4th edition, 1995
Syvanen A C, *Clin Chim Acta* 1994;226(2):225-236
Szabo A. et al. *Curr Opin Struct Biol* 5, 699-705 (1995)
Tacson et al. (1996) *Nature Medicine.* 2(8):888-892.
Te Riele et al. (1990) Nature. 348:649-651.
Terwilliger J. D. and Ott J., *Handbook of Human Genetic Linkage, John Hopkins University Press, London,* 1994
Thomas K. R. et al. (1986) *Cell.* 44:419-428.
Thomas K. R et al. (1987) *Cell.* 51:503-512.
Thompson et al., 1994, Nucleic Acids Res. 22(2):4673-4680
Tur-Kaspa et al. (1986) *Mol. Cell. Biol.* 6:716-718.
Tyagi et al. (1998) *Nature Biotechnology.* 16:49-53.
Urdea M. S. (1988) *Nucleic Acids Research.* 11:4937-4957.
Urdea M. S. et al. (1991) *Nucleic Acids Symp. Ser.* 24:197-200.
Vaitukaitis, J. et al. J. Clin. Endocrinol. Metab. 33:988-991 (1971)
Valadon P., et al., 1996, J. Mol. Biol., 261:11-22.
Van der Lugt et al. (1991) *Gene.* 105:263-267.
Vlasak R. et al. (1983) *Eur. J. Biochem.* 135:123-126.
Wabiko et al. (1986) *DNA.*5(4):305-314.
Walker et al. (1996) *Clin. Chem.* 42:9-13.
Wang et al., 1997, Chromatographia, 44: 205-208.
Weir, B. S. (1996) *Genetic data Analysis II: Methods for Discrete population genetic Data, Sinauer Assoc., Inc., Sunderland, Mass., U.S.A.*
Westerink M. A. J., 1995, *Proc. Natl. Acad. Sci.,* 92:4021-4025
White, M. B. et al. (1992) *Genomics.* 12:301-306.
White, M. B. et al. (1997) *Genomics.* 12:301-306.
Wong et al. (1980) *Gene.* 10:87-94.
Wood S. A. et al., 1993, Proc. Natl. Acad. Sci. USA, 90: 4582-4585.
Wu and Wu (1987) *J. Biol. Chem.* 262:4429-4432.
Wu and Wu (1988) *Biochemistry.* 27:887-892.
Wu et al. (1989) *Proc. Natl. Acad. Sci. U.S.A.* 86:2757.
Yagi T. et al. (1990) *Proc. Natl. Acad. Sci. U.S.A.* 87:9918-9922.
Zhao et al., *Am. J. Hum. Genet.,* 63:225-240, 1998
Zou Y. R. et al. (1994) *Curr. Biol.* 4:1099-1103.

What is claimed is:

1. An isolated, purified, or recombinant polynucleotide comprising SEQ ID NO: 20, or a sequence complementary thereto.

2. An isolated, purified, or recombinant polynucleotide encoding a functional glycine transporter, wherein said polynucleotide comprises a nucleic acid sequence that is at least about 95% identical, over its full length, to the polynucleotide of SEQ ID NO: 20.

3. An isolated, purified, or recombinant polynucleotide which encodes a polypeptide comprising SEQ ID NO: 32.

4. The polynucleotide of claim 1, wherein said polynucleotide is attached to a solid support.

5. An array of polynucleotides comprising:
   a) the nucleic acid sequence of SEQ ID NO: 20, or a sequence complementary thereto;
   b) a nucleic acid sequence encoding a functional glycine transporter, wherein said polynucleotide comprises a nucleic acid sequence that is at least about 95% identical, over its full length, to the polynucleotide of SEQ ID NO: 20; or
   c) a nucleic acid sequence encoding a polypeptide comprising SEQ ID NO: 32.

6. The array of claim 5, wherein said array is addressable.

7. The polynucleotide of claim 1, further comprising a label.

8. The polynucleotide of claim 1, wherein said polynucleotide is operably linked to a promoter.

9. A recombinant vector comprising:
   a) the nucleic acid sequence of SEQ ID NO: 20;
   b) a nucleic acid sequence encoding a functional glycine transporter, wherein said polynucleotide comprises a nucleic acid sequence that is at least about 95% identical, over its full length, to the polynucleotide of SEQ ID NO: 20 or
   c) a nucleic acid sequence encoding a polypeptide comprising SEQ ID NO: 32.

10. A host cell comprising:
    a) the nucleic acid sequence of SEQ ID NO: 20;
    b) a nucleic acid sequence encoding a functional glycine transporter, wherein said polynucleotide comprises a nucleic acid sequence that is at least about 95% identical, over its full length, to the polynucleotide of SEQ ID NO: 20;
    c) a nucleic acid sequence encoding a polypeptide comprising SEQ ID NO: 32;
    d) a recombinant vector comprising SEQ ID NO: 20;
    e) a recombinant vector comprising a nucleic acid sequence encoding a functional glycine transporter, wherein said polynucleotide comprises a nucleic acid sequence that is at least about 95% identical, over its full length, to the polynucleotide of SEQ ID NO: 20; or f) a recombinant vector comprising a nucleic acid sequence encoding a polypeptide comprising SEQ ID NO: 32.

11. A method of producing a glycine transporter type 1 (GlyT1) polypeptide, said method comprising the following steps: a) providing a host cell comprising: i) the nucleic acid sequence of SEQ ID NO: 20; ii) a nucleic acid sequence encoding a functional glycine transporter, wherein said polynucleotide comprises a nucleic acid sequence that is at least about 95% identical, over its full length, to the polynucleotide of SEQ ID NO: 20; or iii) a nucleic acid sequence encoding a polypeptide comprising SEQ ID NO: 32, operably linked to a promoter; b) cultivating said host cell under conditions conducive to the expression of said polypeptide; and c) isolating said polypeptide from said host cell.

12. A diagnostic kit comprising the nucleic acid sequence of SEQ ID NO: 20, or a sequence complementary thereto.

13. The array of claim 5, wherein said polynucleotide comprises SEQ ID NO: 20, or a sequence complementary thereto.

14. The array of claim 5, wherein said polynucleotide comprises a nucleic acid sequence encoding a functional glycine transporter, wherein said polynucleotide comprises a nucleic acid sequence that is at least about 95% identical, over its full length, to the polynucleotide of SEQ ID NO: 20.

15. The array of claim 5, wherein said polynucleotide comprises a nucleic acid sequence encoding a polypeptide comprising SEQ ID NO: 32.

16. The recombinant vector of claim 9, wherein said polynucleotide comprises SEQ ID NO: 20.

17. The recombinant vector of claim 9, wherein said polynucleotide comprises a nucleic acid sequence encoding a functional glycine transporter, wherein said polynucleotide comprises a nucleic acid sequence that is at least about 95% identical, over its full length, to the polynucleotide of SEQ ID NO: 20.

18. The recombinant vector of claim 9, wherein said polynucleotide comprises a nucleic acid sequence encoding a polypeptide comprising SEQ ID NO: 32.

19. The host cell of claim 10, wherein said host cell comprises the nucleic acid sequence of SEQ ID NO: 20.

20. The host cell of claim 10, wherein said host cell comprises a nucleic acid sequence encoding a functional glycine transporter, wherein said polynucleotide comprises a nucleic acid sequence that is at least about 95% identical, over its full length, to the polynucleotide of SEQ ID NO: 20.

21. The host cell of claim 10, wherein said host cell comprises a nucleic acid sequence encoding a polypeptide comprising SEQ ID NO: 32.

22. The host cell of claim 10, wherein said host cell comprises a recombinant vector comprising SEQ ID NO: 20.

23. The host cell of claim 10, wherein said host cell comprises a recombinant vector comprising a nucleic acid sequence encoding a functional glycine transporter, wherein said polynucleotide comprises a nucleic acid sequence that is at least about 95% identical, over its full length, to the polynucleotide of SEQ ID NO: 20.

24. The host cell of claim 10, wherein said host cell comprises a recombinant vector comprising a nucleic acid sequence encoding a polypeptide comprising SEQ ID NO: 32.

25. The method of claim 11, wherein said host cell comprises the nucleic acid sequence of SEQ ID NO: 20.

26. The method of claim 11, wherein said host cell comprises a nucleic acid sequence encoding a functional glycine transporter, wherein said polynucleotide comprises a nucleic acid sequence that is at least about 95% identical, over its full length, to the polynucleotide of SEQ ID NO: 20.

27. The method of claim 11, wherein said host cell comprises a nucleic acid sequence encoding a polypeptide comprising SEQ ID NO: 32; operably linked to a promoter.

* * * * *

UNITED STATES PATENT AND TRADEMARK OFFICE
CERTIFICATE OF CORRECTION

PATENT NO. : 7,358,066 B2
APPLICATION NO. : 10/484690
DATED : April 15, 2008
INVENTOR(S) : Gilbert Thill et al.

It is certified that error appears in the above-identified patent and that said Letters Patent is hereby corrected as shown below:

Column 6,
Line 34, "glutunine" should read --glutamine--.

Column 11,
Lines 64-65, ""complement thereof" 0" should read --"complement thereof"--.

Column 14,
Line 29, "art Such" should read --art. Such--.

Column 16,
Line 29, "region staring from" should read --region starting from--.

Column 24,
Line 28, "(VSLSIPS$^{TM}$)" should read --(VLSIPS$^{TM}$)--.

Column 25,
Line 6, "8 to 1 amino acids" should read --8 to 10 amino acids--.

Column 31,
Line 20, "7 bacteriophage" should read --T7 bacteriophage--.

Column 33,
Line 53, "Barn HI" should read --Bam HI--.
Line 55, "17 and" should read --T7 and--.

Column 38,
Line 12, "one-genes" should read --onc-genes--.

Column 42,
Line 32, "GAL-1HIS3" should read --GAL-HIS3--.
Line 36, "lacZmef" should read --lacZmet$^-$--.

Column 43,
Line 42, "(nAChRS)" should read --(nAChRs)--.

Column 51,
Line 5, "m from" should read --III from--.

UNITED STATES PATENT AND TRADEMARK OFFICE
CERTIFICATE OF CORRECTION

PATENT NO. : 7,358,066 B2
APPLICATION NO. : 10/484690
DATED : April 15, 2008
INVENTOR(S) : Gilbert Thill et al.

It is certified that error appears in the above-identified patent and that said Letters Patent is hereby corrected as shown below:

Column 61,
Line 23, "Geysen II." should read --Geysen H.--.
Line 25, "liposoines" should read --liposomes--.

Signed and Sealed this

Twenty-sixth Day of August, 2008

JON W. DUDAS
*Director of the United States Patent and Trademark Office*

SEQUENCE LISTING

```
<160> NUMBER OF SEQ ID NOS: 37

<210> SEQ ID NO 1
<211> LENGTH: 37889
<212> TYPE: DNA
<213> ORGANISM: Homo sapiens
<220> FEATURE:
<221> NAME/KEY: misc_feature
<222> LOCATION: 1..2000
<223> OTHER INFORMATION: 5'regulatory region
<220> FEATURE:
<221> NAME/KEY: exon
<222> LOCATION: 2001..2097
<223> OTHER INFORMATION: exon 1
```

```
<220> FEATURE:
<221> NAME/KEY: exon
<222> LOCATION: 2078..2097
<223> OTHER INFORMATION: exon 1a
<220> FEATURE:
<221> NAME/KEY: exon
<222> LOCATION: 9040..9154
<223> OTHER INFORMATION: exon 2
<220> FEATURE:
<221> NAME/KEY: exon
<222> LOCATION: 16083..16361
<223> OTHER INFORMATION: exon 3
<220> FEATURE:
<221> NAME/KEY: exon
<222> LOCATION: 16848..16953
<223> OTHER INFORMATION: exon 4bis
<220> FEATURE:
<221> NAME/KEY: exon
<222> LOCATION: 16860..16953
<223> OTHER INFORMATION: exon 4d
<220> FEATURE:
<221> NAME/KEY: exon
<222> LOCATION: 16860..17014
<223> OTHER INFORMATION: exon 4ter
<220> FEATURE:
<221> NAME/KEY: exon
<222> LOCATION: 18565..18789
<223> OTHER INFORMATION: exon 4c
<220> FEATURE:
<221> NAME/KEY: exon
<222> LOCATION: 21686..21847
<223> OTHER INFORMATION: exon 4
<220> FEATURE:
<221> NAME/KEY: exon
<222> LOCATION: 22526..22599
<223> OTHER INFORMATION: exon 5a
<220> FEATURE:
<221> NAME/KEY: exon
<222> LOCATION: 22526..22682
<223> OTHER INFORMATION: exon 5
<220> FEATURE:
<221> NAME/KEY: exon
<222> LOCATION: 23312..23443
<223> OTHER INFORMATION: exon 6
<220> FEATURE:
<221> NAME/KEY: exon
<222> LOCATION: 24786..25056
<223> OTHER INFORMATION: exon 7
<220> FEATURE:
<221> NAME/KEY: exon
<222> LOCATION: 26827..26897
<223> OTHER INFORMATION: exon 7bis
<220> FEATURE:
<221> NAME/KEY: exon
<222> LOCATION: 30421..30553
<223> OTHER INFORMATION: exon 8
<220> FEATURE:
<221> NAME/KEY: exon
<222> LOCATION: 30760..30894
<223> OTHER INFORMATION: exon 9
<220> FEATURE:
<221> NAME/KEY: exon
<222> LOCATION: 30990..31093
<223> OTHER INFORMATION: exon 10
<220> FEATURE:
<221> NAME/KEY: exon
<222> LOCATION: 31779..32016
<223> OTHER INFORMATION: exon 11
<220> FEATURE:
<221> NAME/KEY: exon
<222> LOCATION: 32108..32242
<223> OTHER INFORMATION: exon 12
<220> FEATURE:
<221> NAME/KEY: exon
<222> LOCATION: 32351..32450
<223> OTHER INFORMATION: exon 13
<220> FEATURE:
<221> NAME/KEY: exon
<222> LOCATION: 32355..32450
```

```
<223> OTHER INFORMATION: exon 13a
<220> FEATURE:
<221> NAME/KEY: exon
<222> LOCATION: 32539..32639
<223> OTHER INFORMATION: exon 14
<220> FEATURE:
<221> NAME/KEY: exon
<222> LOCATION: 35181..35551
<223> OTHER INFORMATION: exon 15a
<220> FEATURE:
<221> NAME/KEY: exon
<222> LOCATION: 35381..35551
<223> OTHER INFORMATION: exon 15
<220> FEATURE:
<221> NAME/KEY: exon
<222> LOCATION: 35667..35897
<223> OTHER INFORMATION: exon 16
<220> FEATURE:
<221> NAME/KEY: misc_feature
<222> LOCATION: 35882..37889
<223> OTHER INFORMATION: 3'regulatory region

<400> SEQUENCE: 1
ggccccaagc ccctaggcct gagggcatcc tggaagtctg gcttgcagca ccctacacct      60
gcctcccttc atatggattc cctgagccat gaaaactctc ggaatcttca ctgagtgttc     120
ttagcgctca gtgccctctt ctaggcctgt ccccacccca gcctactgct ggaagggaga     180
aggagggagg cctttccccc ttcatactct tccttgtccg ccttcctcta cttgggggcc     240
tcttcgacat cctccatctg ccttccctgg ggtggtatcc cttttgatga gccccagcga     300
ggaggcaagg aggaagatcc taaaaaaaac ttatggagga agttacgtcc tgcaggagaa     360
gatatagagg gcttggaccc catctgccca gtcccaggaa ttgagcacac acataactac     420
acagacctgc tgcagtgcac acaatcagtc ttccacagat gtacctacac aaatacacaa     480
tcggggctca ggtgtctggg ggcacagaca caacaggttg cctagatcca ggtgtgtgtg     540
cacacaactc acgcaagaaa cacctgcact tggcttgtag gagactaaaa atcccaaaca     600
tgctatacct actaggtttg gggacaaagt aaaagtgaaa ataatctcgc tgataagact     660
aaggtgtctt cccagatctg atcaggagtc aatgtgaat aggagacaac agagagctgt      720 cttttgtactt tggctctgag gaaggtttgt ggaatggacc gcgtgtggcc tgagagagct    780
cgcatttcag ggaatgcctg ggcttgatgc ctgttatctt gttcagtgcc tctgataaat     840
taataaactg gaatctcact caacaattgg tttcacgtga gtttggcatg tgtgcactcg     900
cttcttggag gctgactgtc ccaaggaaaa aaattaaact gtttcctggc cagaaaatgg     960
tgaggactca gggtccaaag tagaaattgc ctctgtgggc tgggccccct ccctgagcag    1020
atgccctact caggttgggg caaaaccag ttcctctgac agaactaact ggccactctc      1080
catgaaaggt ggtggctctc acaaggtatg caaatgtggg aggctcattc caaatgccag    1140
ccaccactcc ccagaggcag cctggagcaa tgggctttat atacacacac atgcatttcc    1200 ttagccccctt ctctctgttt cacagaggag gaaaccgagg ctcaccatgc tccttttggc    1260
aaagactctt ttttagctga gattgtaacc caggtctgtc tcaccatgga aggaggaggg    1320
atcccaggtt ggtgtctgca gcccctgtaa caccacctca aaagtagagc tgaccaagcc    1380
ggtggtccag gagggaaatt tgagaaaggg ctaccccgag ccctccagtt ccaaggagta    1440
ggacctaggc cttacccagc aatgcccaca gtctctagcg gctctgctcc aaagggaatg    1500
gaatttgctc tgacttctct ctaggggaaa cgcaggcgca gaaggccagg ggcctggagg    1560
gctaactcca gcctcagccc cccatagtgc cccaggcctt ctggcttcat tccagcctag    1620
cccgaagggg cccacatctg cttgctcaag ggccccagct ggagggcagc gaggcagggg    1680
```

-continued

```
cggagaaggg gactcctttg tggcgctcac tcccagggt tcgtgggat caatcatctg    1740 aaagctggag agacttgtaa ttttattccc tgggaggagg agcctgagaa gtcggcacgg    1800
gaggagggga tgggatggag aggggaggac ggccagggga gccgttcggg taggggaggg    1860
acttggctag atctcccaag ccttctccac tcttcaaact ttcaccaaac tcttagcccc    1920 cgcctcccg aaaccaaaac acaacaggct gtggaagagc tgcgagcggc gcggcgggc    1980 gggcgaactc ggcgcggcac agagcctcgg gaggctgatg caactttccc tttaagaaag    2040
ccacctgggc gcaccgcggt gcggacccag cacgcctggg ccgggggctg cagcatggta    2100 aggggctgg gggaagggac gctggggccc gcgcctccgt ctgtcctgcc gtcggtctga    2160
gtgttcggcg ctccgcggg gctgagcccc aggaccagcg tgtgcgtgtg tgtgtgtgtg    2220
tgtgtgtgtg tgtgatcgcg catgtatgcg ggcatctgtg ggtaagagtg tgggtgcacg    2280
caccgggatg tctgtctcgc cgcaaaggtc ggggtaggtg cgcgcgtctg ggtgtcaccg    2340
ctgtcaccaa ggagctgaag cgggagggag agggaagtgg ggggagctcc tgcgtggggt    2400
ggcggggggg cgccagacgc cggttcgatc ggggcggcg ggcgcaggct gtgcgggtag    2460
cgccggagcc agagcgtggc actgtccgtc cgaggagcca gtggttctgc gctctggggg    2520
cctgcagggg tcgacagtcg gccgtgcctg cacccagcgt gcgggctccc gctcgctcca    2580
tcgcctctca gcgaccgcca gcctggctgc ctatctggcc cctccagccg gcctgcctcc    2640
ctatctgccc tcccggtgcc ggttccagtg cccgtgcgcc cgcgggaccc gggaagccgc    2700
gcgggagagt cctggcgcac tcagcctctc tttgtccgcg ctctggccgc ggctttggga    2760
agggactgcg agcgagccgg gagttctctg ggggttgcta ccctgggaag aatccgtgcc    2820
ctccccaccc caaccctcat taccggcaca cctaggcgg ggccgggcgg ccgcaggtga    2880
gggcaggggc ctagcagccc tggagagccc accccggcc ggcgctccgc acccggcagc    2940
cactgcagat ctcgagcagg cggcggggcc gggccgggcg ggagagtggg gcttgcccgg    3000
agggccggga ggggccggtg ccggcccggg ggcggggccg tggggcgggg acctcggcgc    3060
cccggtactt ttccaccgca gggggccgggg gcggggccgc cgcctccacg ccagcttagg    3120
cccacacgtg gcggctgatg taacgcccgt gccccacat ctctctcccc gattaaagcg    3180
gacgcgcccc acttcgagga accgggacgc tgcgggcggt gccgctgctc ccagaccgac    3240 cgcgccctg cccgccggcc ggaggcctcc gcgcctcggg ccggcggata cttaaaggag    3300 ccgcacccc tttcgggcct gctctccgca agccacaccc cctcgcggat cactcttaaa    3360
ggagacggga cgcttgctcg ctgacagctt ccgcacaaag cgcggtctat ttctccgctg    3420
aaaggagcgt gagggtgcgg ccgttgggaa ataaaggctg cagggcgagg agtggggaaa    3480
gagaaaaacc tgaaaggtta aagactgcca aagtgaggga gcatcagaag gttggagagt    3540
agtgggtgag gggactggtt ctagggacta atgggcgaca ctgagcatgc ccaagtgttt    3600
ccaaggaccg cagagaaaac gccccctta cttggcctat gcggcgactg cggctgtacc    3660
tgctcagttc ccggctctgg ggacacagaa gaatcacgcc tctgccctgg tagaactctc    3720
catctagtgg ggagccagac ttgggcacaa ggaagcatgc ctcaattgct acgtgtggca    3780
agcgtggggg tacagtagga aggctgacag caacggggag gacctaggaa ggcttcatga    3840
agataatagc attgggatag gttttgagga tgggtaggat acatacaggt ggaagtggag    3900
acaagggtgc tcaaaaaaca tggaacgggt gccggggcaa aggcatgaag caggagccct    3960
ctgcaagtgc tgggtagtct cacgtggcgg cagatggccg caggctgctg acctgggctc    4020
```

```
ccaggtagaa ctaagggctg tttcctgctc ccacagctcc tccacttcct ccaacacagt    4080
gaatggaaat tatgcttctt cctctgtcta ctaaactgtg cggtccttca agctaggaaa    4140
agagcctgtc acctttccat cccccgtgag gactccaggg cttggccaag atggaccgtt    4200
aaaactgatt gacctgacag tcctgtctga tactcagcgg tgagactgtc aaggtgggcc    4260
agggttctgt ggctgatgtc tcaacatctg gctcacaagc agctcagacc agcttgtcca    4320
agccagccct cctgtccccg caccaaacct gcagcctcac cagcattcgt cctctgggtc    4380
gggcaccggt ttcctcccac tgcaccagca gaaaccagag actccttctt atccctcccc    4440
ctacccagtc cgattcatca ccaagtctcg ccatgttgcc ttttatattt ctctgaaatc    4500
tgtgcacctc tcctcaccct gttgtcacct tcctaacctg agccccttca tttttggcct    4560
ggctccttcc ttccttcctt ccttcttttc ttccttcctt tctttcttt tctctctctc     4620 tttctttttt cttttctttt ttcttttgac ggagttttgc tcttgttgcc caggcaatag    4680
tgcaatggca caatcttgac tcactgcaac ctctgtctcc caagttcaag caattctcat    4740
gactcagcct cctgagcagc tgggattaca ggtgcctgcc accacgccca gctaatttcg    4800
tatttttagt agagacaggg tttctccatg tcggtcaggc tggtctcgga ctcctgacct    4860
caggtgatcc acccacctcg gcctcccaaa gtgctgggat tacaggtgtg agccactgcg    4920
cccagcctgg cctggcccat ttctaattga cttcctctct tcaacttcag cctccctcca    4980
gtcctttctc cacactgtat ctaggggat ggtttcaaga tgcacattcc accaatggct     5040
cctccttgaa gttgatcttc tgcttaaaag ctttcaatag gcaccttgcc ctcaagatga    5100
agaccaaaat ccagacccca aaggccctgg ccaggcctct ctgtccactt taatctttga    5160
ccatttcccc ctgactgtct gagctccagc ctcagagcct ttccacatat tgttccattt    5220
gcttgactct ctcttcctct tctcttcctc attattgcca ctttgcctaa ttaacttctt    5280 tagacccttca aacatcactt catcagggaa gccctcccct agtcttacac aaggccaggc   5340 cccctattg tagagtctca taacacaatc tttgtctttt acacccttta tctcagtagg     5400 cagttctttta ttttttatt tttgagataa gagtttcact cttttgccc aggctggggt     5460 gcaatggcgt gacctcggct cactgcaacc tctgcctcct ggattcaagt gattctcctg    5520
cctcagcctc ccaagtagtt gggattacag gcgcctacca ccacgcccag ctaattttgt    5580 gttttagta gagacgggcc ttcaccatgt tagccaggct ggtctcgaac tcctgacctc     5640
aggtgatttg cctgccttgg cctcccaaag tgctaggatt acaggcgtga gccaccactc    5700
ctggtctcag tttgtaattc tttaaatttt agtcattggt ttaactcttg cccttagtc     5760 tgtaagctgc aggagtgcag ataccttga gttcttggtg cctagcacag gtctggtcca     5820
gagcagacct gcaatcaata ttgtggaata aatgagtcca gctgtggcca gccttaaacg    5880
cctgctaagc aatttaggcc atatcctgtt ggctgtggaa aactgttgga gagaatcagg    5940
gatttagggc tttgggaaga ttaacagatt ggaggggagg aacatgtgga gggcttgtgg    6000
aaaggataaa aattaggcag aaacttcaga acttacgagg aaactactgt tagccccatc    6060
ttccagactg agaaaactaa ggctcaaaga ggttaagtaa cttactcgaa atcacatacc    6120
tggtgagtag ctgagccaga aatccagccc aggcctacca gatcccagag cctgagctct    6180
ttatcatgtc ctaaactgcc tctgtgaccc actactgctt gtcaacagtg gcccacaagt    6240
gcttcagggg catgtgtggg gcctggtgtt gtggatcttc cacacgtaga agagactgga    6300
cgccacgggc aatcagttgg tgttttctga atggacggat gggaccatgt aacaggaatg    6360
tcaaaggcag gagaagcagc aaagctttac acccagctca ttctcctgga agccgccatg    6420
```

```
aagcagtctt ttccctccag tccacgaact acctgagggc agggactgca tttgcagtca   6480
gaaatgtcag agtcagagat gtagggtctg aaaacctagt tcaagtcctc actcgagcac   6540
ttacaaggaa ggcatgtgac ctctccgagt ctgtctctct gatggtaata ggaggaattg   6600
gaggaattcc aggataacct gggtgagggc cctctgcagc ctaagttctg agacacagtg   6660
tcctcagttt acttacctga ccagcgggct taataatttc caacctgtga cgtggctttt   6720
ttgtggctct ttttttttt ttagacaatg tcttgctctg tcgcccaggc tggagtacag   6780
tggtgtgatc tcggctcact gcaatctctg cctcccagat tcaagccatt ctccgtctc   6840
agcctcccga gtagctggga ctacaggcgc ataccaccat acctggttaa ttttatatt   6900
tttagtagag acgggatttc gccatattgg tcaggctggt cttgaactcc tgacctcagg   6960
tgatccgccc gcctcggcct cccaaagtgc tgggattaca gccgtgagcc actgcttcca   7020
gctgacatgg ctcttctaa tgccatctgc tgttattact atcatcattg tcattattag   7080
tccttgactg cagacagatg gctttaagga agtcaaatat agagtttaca cctggagagg   7140
gaggcacagg ggtgagagag acaaggtgt gatctacttt taaggagca cacccgcgct   7200
tcccctactt gcccccagaa gaccaaagcc atgagcagga acctctttag gaggacaagt   7260
tgagccacag gccagcctgg gtcacatctt gtccccaccc tgccctgaag agaagctctg   7320
caggagacca ggcagccagg gcaaagggcc taaaatgcc aaggcctgat ttgcataggc   7380
aaagagcagc ctcctcatct ctcctccagc cttccagaga cttcctgcat ttgtaggtga   7440
gaagggccc ttgacaggtg gctgtgggtg gggcagagtt gcccagagta gccttgggaa   7500
cagagttgac tccctgggaa ggcaagaaag gctccagaaa ggcagagccg aatccttcct   7560
ggggtttcct cccatgagtc aattcttttt ttttttttt gagacggagt cttgctctgt   7620
cacccaagct agagtgcagt cgcgcaatct cggctcactg caacctctgc ctcccaggtt   7680
ccagcgattc ttctgcctca gcctcccgag tagctgggat tacaggcacc tgccaccatg   7740
cccagctaat ttttgtaatt ttagtagaga caggggtttca ccatgttggc caggatggtc   7800
tcaaactcct gagctcaggt aatccacctg ccttggcctc ctaaagtgct gggattacag   7860
gtgtgagcca ccacgtctgg ccaagataac tttttttttt ttttttttga cacggaacct   7920
tgctctgtcg cccaggctgg agtgcaatga ggcaactctt taaggctgtc tgaagatgga   7980
tttctcccga ggcctgtcaa aaactaacct ttcttccgtc ccatctgaca ttaatccagt   8040
gtgcaccagc attgccatga gactgttcct tccacgtggc tgctgccccc agctcgcca   8100
gccccaccttt gccactcaga tgcttcccac aagatcctgg gctggcctgg acccctcatt   8160
tcagaggtcc cgacttcgct atttccctcc atttcaattc aaataacaaa cacatcttgc   8220
aagtccagtg ctgtgctaca tgctgggcac agagggtaaa agaaacacag tcccaagccc   8280
tcggggaact cactgactca tagttgacga acttataagc aaataagtgt catatgaaat   8340
aagagtactc gtagagattt gcacaaaaca gaaaggagga agcaacttt tcattctttt   8400
gagagagagg gtcagaaaag gctgcagaga agaggtgaca tttagcccgg tgcagtgccg   8460
aagatttgta gaatttcacc tggtgaactg ctgtggaggg gacagctggg agtgcaagga   8520
ggtgcggctg cacatgggtg tgtggcaggc ccagaactcg gttcaagtga atgcatgac   8580
aacaaaccca gctgccctgg agcccacact gagtgccacc cagataggaa aggaccatcc   8640
tggctgcctg gctggggtga ggatggggag agtgtgctga tctgagctga ttcccctcct   8700
ggggaaaggc tgaagccatt cacacagacc atgaaggaat tggactccat cccagtttgg   8760
```

-continued

```
tattcatttt ttatctttta taggattggg catctggaaa gtcaaaaata gacctttgcc   8820
cattgggaca ggaagcctgg agatcaagag atccaggggga aaggttgggg ggactgggaa   8880
ggagctggat ctgagggtct tccagaaagg agcaggatat ggacatggcc tggcagaggg   8940
cctgggcagg ctggtggtgg gtggctcggc actacctgtc tggagagccc tgtgggccac   9000
acggccaagt cctcacctca ccctctgctc tctccacagc tcttgagatc tgtggcctga   9060
aaggcgctgg aagcagagcc tgtgagtgtg gtccccgtca ccagagcccc aacccaccgc   9120
cgccatggta ggaaaaggtg ccaaagggat gctggtgagt acagaggcca gactgcggga   9180
aggaacggga gtcccaagcc ctgcccccag gacctcctgc cagctgcttg gaaggcttag   9240
gaaggccggc actgccaggg ctcctgagtg cccagctgac cccggcctgg gcaggtagcc   9300
cctcatctag caggtcagag agcatcaggc tccaagcccg cagagcccgc aaagacctgc   9360
cagaaggcag gaggtgtggg ccccatcctt gtcacagagg tgctccagac agaaggaggc   9420
cactcatatg ctgagaggac agtggacgcg gggctgtgca ggcgccttca gtctgtgctg   9480
atcaagggt cctccctcag accctgcctg gttttctcc acttctttgg gtccttctca    9540
gtctgaaaag taacaaagaa catttgttt tgaatcctct cctgaggcct cccagaaaat   9600
gtccctccac ccttttcccca agtcctggct cttctttgcc ctcagcctta gagcacagga   9660
gaggtagtgg tgaggccacg agacacggga gaggtagtgg tgaggccacg agacacagag   9720
gggtggatga gattcttttt atttttttta atttttttga gactaagtct cactctgttg   9780
cccaggctag agtgcagtgg cgtgatctca gctcactgca acctctgccc ctgccgggtt   9840
caagcgattc tcatgcctca gcctcccaaa tagctggggt tacaggcatg agccaccatg   9900
cctagctaat tttgtatttt tagtagagac ggggtttcac catgttggcc aggctggtct   9960
caaactcctg accttaggtg atccacacgc ctcggccttc caaagtgctg agattacagg  10020
tgtgagccac cgcacccggc ctgggtgagg ttcttgaagg agcaagactc gctgatggat  10080
ggaccaggtc agcaccagaa gcaagaacca agaaaatgat gccaaatcct gtcccagagg  10140
caatggttgt cttccttctc ttgagatctt ccctggggac aggctagact ggacggctgc  10200
cggggtggg gacctgggac tgagcatgga cagtccctcc ctcagcagct cccatccttt  10260
caatcccctg tgttgctttt ctcatttagt gaaagagtca ttggcctggt gtctctactg  10320
agccctcccc aaacgagccc tgtctctcac caaagatttc tgggactcaa agtacctggt  10380
ttaaaagaac aacttgggct gggcagggtg gctcacgcct gtaatcccag cactttggga  10440
ggctgaggag ggcagatcac ttgagatcag gagtttgaga ccagcctgac caacatggtg  10500
aaaccttgtc tctactaaaa atacaaaaat tagccagatg tggtggtgcg cacctgtaat  10560
cccagctact tgggaggctg tggcacgaaa atcacttgaa cccgggttgc agtgaggcaa  10620
gcgccactgc actccagcct gggcaataga gcagggctct gtctcaaaaa aaaaaaaaa  10680
aaaaaagaa agaaagaaag aaagaaagaa aattaaaaa acagcagttt gtgggagaga  10740
accggtggtt ctgctccaag ctcaggatct tctatctggc cctgttctga acctccagca  10800
tccaaccct ggccccaacc ctcaggccag ctctggtcta gccccctact gattgactga  10860
ttggagcaag tctgattgaa ccaagctcct gaaagtattc ctgagattcc tgaaatctgg  10920
gtgctcagaa atgggcccag atggagatct tatgacctga acacttgcta ggggtgaatc  10980
ccatctgaga acccaaacat ggccccacct ttcctggaga agtcttggaa ttgccatggg  11040
cttgtgataa gaagcgggt gtggccctgc cccttcctac catggagatt ctgagcccca  11100
tgaaacctct gagtcctccc tggttgctct ttcttctctg gagtgacctg gaaggactgg  11160
```

```
gaggagggca ggcaggagag atgtgagcag cacagagggc atggctccca gtgtcccaga   11220
gtccctgcct gagctgagct tcccggactg tgctctgccg gtcggcccgg ccagcctgtc   11280
tatggatggg aatgctgcct tgggactcct gttcccagca ccaggatgtg cctaaagata   11340
gctggggctc gctctcctcc ccgctctctg ccctttggct tttgcccact gttgctgcgt   11400
ttgaggccca tagcatctgt cccatgggca cccccagtgg ttgcttggag attctattcc   11460
tgcttccttt tcagttctgc tgatgacctt ggagtactcc actctattct tgggttccag   11520
tttgggactg aagccacctc cattcagtgc ttgtctctag acacagcctc tgaggtgcat   11580
agggcagctg gtccctgctg agccccgtct cttctaacac aggcagccca gtcagcacat   11640
ttgtgtcttc tgtgtcttcc tatggctagt aactaaggaa gcttcattct gacagggttc   11700
ttctttggat accctggtag atcagaagag aggatgttaa ggggcgtgtg tgtgagccat   11760
gcacttggac catcccagtt ctccgtggct tctgctgctc tatttgtgcc ctggcatgca   11820
tggagcaggc actggcccct accatgggat cctcacttct atccccctttt acccaggttt   11880 gggtgtgagg acactggccc tccaagtctc ttcagtgtcg gcagacaccc tgtgttatcc   11940
ttggagcttc tgctggatgc tacagccagt gccccatggg taacaagcag cttaccagca   12000
cgtgcccagg cccacatgcc tgctgcacgt gtccctccct cactccagcc cagatggtct   12060
ctgccaggcc agctcagctg cctccctcac gcctcagcag ctcctaggac agggctgtgc   12120
gagaacccag ctggccaggg tgcctccaag cctgggagca gctgggatgc ttgggggcac   12180 taggggggtgg gtggggtggt cctcccgtgg agacctaggg cctcatacac gtgcggagca   12240
gggccaccta ggtctcaaag acaaggggc tggaggagag ggacccagga caggaggcaa   12300
gagagccccc actagctcag ttttaatcct ccacccacca atgtcacacc atttcccagg   12360
ctggccacct cagtcccctc cctagtgcca ctgcccactc atgcagagtc ttgggcagtt   12420
caggccttgg tgagctttgt tgacctcttc ccatgtctga gcacactgat tgtttctgcc   12480
actgggaagc cttacaatga acaggaacag actcatttgg attagggttc tgggtgccag   12540
agtgtccaaa tccaaggagg ccttgcaagc accacaggcc gccaggggct gccccaccct   12600
gacgcgttct catatgtttt tccctgaggg tttgggcacc tcctgtctgt agcatccgtc   12660
ataggacctg gcacatagtg gggactcacc cagcccaagt gttggcatgt agcaagagct   12720
caactagtgc aggcttggtg cattattggg aggtcaccaa gcacagggtt tggcacacct   12780
tggacactcc cttggtagag ggcctgtccc tgcctgggca ctcacctaac cgaagtctta   12840
gcgtgtggca aatgctcaac tagtgcagac ttggcacaca ttaaacactc ccttagaaga   12900
cagcctgtca ccctgtaggc attcatctag cacactgcca ggtacacagt gggtgctcac   12960
ccagctcaga gctgggcgca cattgggtcc ttacctggca cagaattcga catacccggg   13020
gtactcccct agtacaggac ctagcacacc acagggctc cccacctggg gctgacacac   13080
aatgagtgct gtctcagcat cggacttggc acacaagagg cactctgctg atcagcatcg   13140
gatttggcac acggtgggca ctctgctgat gcaggttctc acacacagca ggtgcttcca   13200
gcacaagatt tgacatccag taagtgctat cccggctcag ggcctggcac acagtgggca   13260
ttctccttag ataaggccta gtacagtgga ggtgctcttc tagccaggac agcctaagca   13320
atgaccttcc gctgatccta gattagcagc taccccatcc tccgtgaaat gggcaatatc   13380
tagatccaga ggaaaagttc cagccttcct cagcttcctc tctggtcggg ggccctgccc   13440
tccctccccc tccccactc ctgtctagcc cacctactca accctgtagc ccggcctccc   13500
```

```
acacagcctc cctgcagccc tcccccatcc ccggcacttc tcagtcccag ctcagcggga   13560
ccttccctcc agagtcacag gggacaacaa agacccctagc ctccttgccc ctctggaagc   13620
atgcccactc ttattaggca aagtcagagg cgggagctgg gggagtcagc atccctaagt   13680
ggggctagag cagctggatc tcgctaatga ggcctcatta cggccagggc ccagctgggc   13740
tgctgccgcc tcctgtcccc atggccagag ccagggaaag ccgtccagcc atggctgcct   13800
gttctgggca cccggcccag gccagggcag ccagagccca gagcccaccc tcggtgcaag   13860
tgagcatttg gcatcatgg gtgacgggac cttcctggag ccagtggccc agccagcgcc   13920
ttggccctca gtctgcgccc atgggaagtc aggggagtgt gtctggggac caggcgcatg   13980
aggctggctc agtgagcagc tgagtcggta ggatctgagg ccatccttag gacacttgct   14040
tgagccaagg cctgtcccca tcttccccaa accaacatgg agataataat ggacctacct   14100
catgggacag ctgggaggac ccaatgagtt aagatatggg aagttaactt gtaccatact   14160
aggtgagtgc ccacagggtg atgggctgtc tgtgaagcaa gcgtcccatg tatgctgagc   14220
caggacagtg cctggcccac agcaagcact tactatgtat tttctattac cattattact   14280
aatgctcact agattcaatg attggtgggg ggtttcccg ttttagagat ggagaaactg   14340
agatccgaca tgttaatgga cttgcctaag gttatatatg gtgagaaact gacaaagcta   14400
gggtttgaac ccaggactgt caaactctaa aggctgtgac ttttatctt attttaaaat   14460
ttattttta ttaattttt gaaacaaggt ctcactttgt cacccagttt ggagtgcagt   14520
ggtgtgatca tagctcacta caacttccaa cgtctgggct caagcaaaac tccctcctca   14580
gtctcctgag tagctgggac tataggtaca caccaccaca ccttgccagt tttttgtaga   14640
gacacggtct cactatgttg cccaggctgg tcatgaactc ctgacctcaa gcgaccctcc   14700
tgccttggct tcccaaagca ctggcattac aggcctaagc cactgtgccc cacctgtctt   14760
tttatttta tttattatta ttattattat tattattatt attattatta ttttagagag   14820
agagttttgc tcttgctgcc caggctggaa tgcaatggcg cgatctcggc tcactgcaac   14880
ctccacctcc cgggttcaag cgattctccc gcctcagcct cccgagtagc tgggattaca   14940
ggcatgtgcc accacgccca gctaattttg tatttttagt agagatgggg ttggtctcac   15000
catgttggtc aggttggtct caaactcctg accttgtgat ctgccctcct cagcctccca   15060
aagtgctggg attacaggcg tgagccaccg tacctggccc tgttttttaaa tttttaatgt   15120
catcctgtgc ttgacaaaac tccttatgtt ccctacgggg ttgccacact caccaaactc   15180
acaggaaagc tgttcttaca ccagaattca tgcacgtgtc catctgactg atatttcctg   15240
aggtcctgtg gtaagccagg ccttctgctg actgaccagt ttccaaaggg cctgacacat   15300
tcctggcacc ggaatgcata tgcccacctt ccgagccact ggtctgaggt atcttgggt   15360
cagcaggaga ctggccagtg tgtgtggcct cagagaaagg gactggatgg gtctgagtgg   15420
catcccacta cagtagtggt gactatagtc atggtgacga caccactgga cctaccagcc   15480
cacgccacgc acactcccag actagcacct cagcttctgg gcatcacggt gcaaatcctc   15540
acgggttctt attccacagt ccccctttgt ctggactctg ggatgacttg ccccctgcc   15600
taatgccatc tttgtccaga cagctgacag cgtggttcac taggccaggg cttttcttgca   15660
tggtcagttg cattctccta ggaagacgcc ccatcaccct ggcagtttgg gagtccccat   15720
ctctggttgg tgggggtgt caggtacagc cctagggctt ggtttctccc agcccgcacc   15780
cctccgtgga gcctgagctg ctctggtggt gccctgtgga ctgtgccttc catcctcctg   15840
ccggtcacca tccagggccc aatggggcag accccgtcac tcatcagaca cccaactacc   15900
```

```
ctagcaggag cccacccagt gctaggcctg tgggctcaga cagcgtctgg tcagctccgt   15960
ggggggagtg agccaccctc tcgcctgctc tgccccagtc tgtgtgtgtg tgtgtgtgtg   16020
tgtgtgtgtg tgtgtgtgtt gttccagtta cttgctggga acaagggaaa acacaacaa   16080
accccacaca ccccactcca gctccggagc acccgtgctg ggctgcatgg ggactggccg   16140
gaggggcagg gccaggggag cgggtaggca gagcttcggg aggagatgag gtgaaagtaa   16200
ttgacgctgc ccagcccggc agtgggagag gcaggggatg cgtcagtgtc gcgctggagc   16260
tggcagaggt gtgaatgagc ggcggagaca cgcgggctgc gatcgctcgc ccaggatgg    16320
ccgcggctca tggacctgtg gcccctctt cccagaaca ggtcagtcac cttccaggaa     16380
gttgagcccc ctccttggtg ccaggcaggc tgagaggctg gctgcggat ggggagaggg    16440
gctgagtggt ctgtgccagg gaggggcagg cacagccagc aagcaagaca gacaccagcc   16500
aaagtgaccc agaaagttgc aactgtgcaa aggagtgtag gaagagttag ctgtgtggtg   16560
ggggtgaggg ggaggagagt gggggtgtga gggctccccc agcccaagga cctgctgaga   16620
atctgctctg tgtatcaaag ctgcattgtc ctagctcccg gggagacggg ccggaggtgc   16680
ccaggaattg tactaatcaa tacagcctca ttgtctgtgc cacggcagtt actcctatgg   16740
gaagagtggg tgagggggca ggggaacgtg gtacatggtt tcagtggcaa ggggtggggg   16800
aagggatgg ggcaagagtc tcagctggga agagagagac cccacagaac attttccagg    16860
gtccagggca agtgcccgca tgggctggga gccggtgtgt cctcatccct ggacgccggg   16920
gacgggtgga gatgtcagcg gatggcagcg agggtgagga gactcgaaag ctacacttct   16980
cccctgtagg acatcctgac ttgaccttca aaaggcaaga gagggaatgt cctctgaggc   17040
gatgtgggat gggtctggga ggaacagtac gcagggctgc cctcaagcct cagtactgct   17100
agggtcaaga accaaagcca cttttccagag tgcctgcctg ctgctagcca gtgagggtag   17160
acgccgcccc cagccgctgc agcacaggac atgaccattg cctccagtct ccctcctgg    17220
gcttgtctgg ggtgggaagc gaggagctgg ccagggtcca cccagggtcc tccatcactc   17280
accccagggc ctggagtgga gcccggcatg cctgggggtg ccagtcatct gtctgcagcc   17340
cacaatattg gcaggtccct tgctgccagt cagggctctg caatggataa gcacaaggcg   17400
tattcttgcc tctctcatct gctatatgaa ggcctggact ctgaaggcac ctggagtcct   17460
gagaggtgcc cagagatggc tctgaggttt gccttgaggc aggaggcatg aatggccact   17520
gggggctgct cggcccgggg gagattttcc catgttctgc ccctccaccc cggcccagat    17580
ctctcccata tccaggtaac tgaggccaga gatcagagct gcagctgggt ctctctgccc   17640
ctactcagtg ccatgtaggt gaaggacaga agattctgtc attgcagggt aggtgctgcc   17700
tgtgggccag gctgggccct gcactgatag gagagaacaa aaactgaggg gtgcctggcc   17760
ggaaggaggt cgtggggtct tctgaggcag ccacaattta ctgtaatggc tgttctgtct   17820
agattcccca ttggggctta gagaaagttg ccagtgatct gatttggctc aaagtcagtc   17880
tgggatgtga ggtcttgccc attctcctcc ataaagtttg tcttggatgg gacttcatcc   17940
catgagcaaa ccctggggct ggagagtcct aaacacaaag cctgctgggt cccagagggg   18000
cccgcccatc cagggcagct ccaggattcc tcagtgtcca cccagagcag gaggggaag    18060
ctcacaattc acaaaaatat ccactggcca ctgatctagg aggcgggagt gtcacaccag   18120
agcacagtca ccgtccaggg tggagagctg ggctccctga gtctgtgcaa cagcaaaagg   18180
caggagtgca tcctggggct ggcccggttc gctctgggag taggctttgt tgctgcattt   18240
```

-continued

```
cctctttacc ttttttctgta ttttctaatt tttttgtgtg tgatagctta ttatgctttt    18300
ataatcagga aaaaaaaggg caaaattgtt tttagtaatc tagaaagcta gtgggaacta    18360
atggaatgta caggggaaag tcagaaatag caaaattcca ggtgagggag agctatggaa    18420
tatgagtagc tacagaggct atctagcctg ggaatctggc agatcgattg aaagtgaggt    18480
tatctagtct atggccatac catcctgaac gcacccgatc ttgtctgata gtgaggttat    18540
ctagtctgtc ccctgctttt gtagacagca gtgctgagat accaagagtg gaagtggctt    18600
gcccagggct ctactggagg agcgggccct agagcaccag ggctctcacc tgcaccggtg    18660
tcccgcctct gccaagccca gggctgagtg ggagatctgg attctgccct cggagctgag    18720
cagccttaat tccaggggct cagccagagc agtaaataag ccaagcagag ggctgtgtaa    18780
aggacttatg taagtgactt tgctcagtgt ggctctccca gctaggcagg aaggggtgg     18840
gaggctgtta aaccaggaaa gatcataagt ccttgtgcca gggtggacac tcctgtctca    18900
atgactggtt ctaagggtaa gggaacatct gaggggtgtg tgtgtgtgtg tatgggtgta    18960
tatgtgtcag ccagctcacc ccaccccgcc atggaaggaa agcctccatt ccttccatgg    19020
ctgggagagc ttggggacag gcagggtag tcctgtcctg gagaccacct gctgagccca     19080
tggcagtggc aagtggaggc tgctttgtcc tggcagtggc ctctcagagc tgccaggaag    19140
ggtgacaggg cacatagggg ctgcctaggg agcctgcaga gaggggggcc aagccagagg    19200
gaaccatgcc gctatggttt aattccccac tgagatgtca gcaagtgagt gagggtgagc    19260
agaggggggc agatggtggt gatggtggtg ggggttagga aagcctgga gcagagccca     19320
tccatggggc tgagctggct caggcagacg ggcagccagt ctgagtcaaa tcgtgagcac    19380
aaagggattt ttccgtgggt acctcagctg atgaccactg cagggacagt tcatatcagt    19440
gacacagccg tccacccagc agatcaagaa aaactagagg cttagaatag gaaagattat    19500
gcaaggaggg agaaaaaaag ccatacagta ttgaaaaaga tttagctgct caggagggaa    19560
gtcagagggt ggtccccaga ggagatctgg acaaggaagg gaactagaac acccagaaag    19620
tgcctggatt ttttttttgga gagtctttcc tccagtttgc ttggagaaag gtaggcctgc    19680
tctgtcgtcc gctgagagct cagccctccc cagccaagcc acctgagcgt agacagccct    19740
ggagttgaag acagaggcca agcctgggcc agattcccgt ggtcgagcgc cacagtgctg    19800
ggacccaggc ccaagcagaa gtgggtgctg cttctgcaag gatcctctgc atacagcaga    19860
cctttagtgt tgtcagaaac ttcctgccag agccccgtcg ccaacccgg ttcagccctg     19920
tcgcgggggc tgtggcctcc ctgggttaca gcccgcacgg ctaagctggt tagcacacgg    19980
ctcattaacg gagcagtggc tggctcttga gggctcaggc aggcggctgt ctgtggcacg    20040
tggctggaag catcaccacc ttcccgtac ctccccctgc cagggaagga gcagacttca     20100
gggatccaaa tgtggtccca cttggtcagg gggtatgggg catctgtccc tcatcctgct    20160
gggaacagga gacaggcctt gatcttcaag ccttgggaac ctggatctct gcaaagggcc    20220
ttgcccttac cctgcccatg ggtccatcct ggaccatcag ttgtccctt tacagctgta     20280
actgctgctc tgtgacccca tccgtgtact gtgctgctgg cacaatcagg cattgtgccc    20340
ctaagtaaac aaccctggga cagaataaaa ctggtattgt agggtcaaca tataggagcc    20400
ctatttggct ggcatttgtt tgggaccaga tagaccaccc ccagcaggcc tcacaccctc    20460
caaaaaatgg gcccttgact ctgtgatctt gccacacctg ccccagtgaa ggccccagga    20520
ggtggtgaca tgctcagaca ggattctgta ggggcatgtc acagagggca cactcaggcc    20580
gggggggcacc ctctaccagg gccaagcatg tcttcaagcc tcttcatcag ggagaccttc    20640
```

```
cttgacctca gccctgcttt cctgccttgt cctccttcca tactcttgtg attttgagat   20700
gatcccctct gtggtcaccc tgaagccaca tctaaagatg atgggtgtat acatttcatt   20760 gcaccccac tagatttcca gctccgaatg ggtaggagct ctctgctgaa gtcccacttc    20820
ctggcacagt gcctggcaca tagccagtgt caataaatct gccattgcat gaatgaatca   20880
atgaatgaat gaaagaaggc ttgttcagcc actgatttgc tctgggtgct ccttgaagga   20940
aacccatggt ccctggcact gcacccctgc cctctgtgga gggtgtgagg atcacatctc   21000
ggcagggtcg atgctggatt gagagcacag ggtggctgcc ccacaaaggt gtctgtgctg   21060
cagtgcccac ccatcaggcc ttggtgcctc ctttgcccac attcccacct ggcctatcca   21120
aggcgcttgg ggcccaggga ggccattcat tccgtctgtg tttgttcatc agcatcaggg   21180
tctgatagca tttcacctgc accaggctgc cttgcttatt gaccagagtg actgctgtcg   21240
aatatgtctc tttcaagcgg agggtgaatg tcacatcact ggcatctctc tgaggctacg   21300
gggctccatc tctgatgcca ggtctgtctg tttctctcag gggaatagct cacctctggg   21360
aggctgtctc tggcactaag gtctgtctgt gtttctgttg gtgacactga gcccctgtct   21420
ccttagtgag acccctgggg cccttgggc tctgattaat ttcctgctca ctgtgggagg    21480
gaggtggaag gagcatggca cttattaagg gacttcttta accaagggac ttgcagagcc   21540
agttccagct tttgggcctg gggttccaca aggggctgtc ctcagtgggg cccaggccac   21600
cagctcagtc ctgcaggccc acattcttc cctggggcaa atccccgcat ctgcctctcc    21660
tgaccttcgg cccctcccc tgcaggtgac gcttctccct gttcagagat ccttcttcct    21720
gccacccttt tctggagcca ctccctctac ttccctagca gagtctgtcc tcaaagtctg   21780
gcatggggcc tacaactctg gtctccttcc ccaactcatg gcccagcact ccctagccat   21840
ggcccaggtc agctccccag ggcccctccc cagccatggg cagtgtagct agctccccgg   21900
accctcccac ctagagtccc agaatgccct cccccatgtct gtcccggctc agctgctccc   21960
ccatttcccc ccagccctgc ccactctgtg cccccaggaa gaagccttca gctgggggag   22020
gggtctaacc tcccctcccc cgcagtcgcc tgccagggg cagcgtgctc agcctggtga    22080
tgtggtaggc gacgggtggg ggggctgtct ggacacaggc cccttttgtgc ccagcctgac   22140 ttggctgctt ggtatgaggc tcagctgctc ccagatcctt acccagaggg gcaagggag    22200 gttttggagg ggcttggggg ctcctggccc tagctccctc ttcagtgtcc cgcctcccgg   22260
atgctggtag cagctcctca ggtgggctgt gcacctggca ctgggtgctg tggggctggt   22320
gagggaagct ctgcttggcg ccctctggca gccactactc tctgcttccc tcctttgcca   22380
ggcctgcctg aagctcctgc cagcagaggg gaagcccggg gaggggtgtt ggagggcca    22440 cggtttccct gctggggggag gcccagaggg tcaggcatgg agcacaaatg ccttgctgat   22500
ggtagcttct ctcctgtccc cacagaatgg tgctgtgccc agcgaggcca ccaagaggga   22560
ccagaacctc aaacggggca actggggcaa ccagatcgag tttgtactga cgagcgtggg   22620
ctatgccgtg ggcctgggca atgtctggcg cttcccatac ctctgctatc gcaacgggggg  22680 aggtacccag tgggcacagg gcagggacca cccacttggg tagagcccac ccaccagggc   22740
ctgggccacc ctctccctgg cacagaccca ctccagataa aggctggcct ctggccctgg   22800
cctccttcgc ccccatccct ggcttaggca ccctttgcct aaggcaggcc accccagacc   22860
ctggcagtct gttgttgggg gctggccctg ccagttggcc cccttttgagg tgaggagagg   22920 tgagaaaagg acctaacccc ccccccccc cgcccacaag gctccctgtt ctattccctg    22980
```

```
gggttcagca gccccccctaa atggttcagg gatgttgagg atctcagcaa cttatgcttg   23040
tgaaatcgct tgtttaaacc atcaaatccc acccaagtat ggaggctctg ggacctggat   23100
tccactccaa gcagaattcc tgagagcctc tgtcaagttg aaagacaggc tggggggtggt  23160 gtgcctcagc ccaggctcct gctcaagcct ggcacactcc tccctgggtc ctacccaatc   23220
gcgaaggttt tgctgttgag ttctgagcag gaagcccagg gtgagatccc tccaagccca   23280
ctcctgagcc agacctctcc ctgcctacca ggcgccttca tgttcccctc cttcatcatg   23340
ctcatcttct gcgggatccc cctcttcttc atggagctct ccttcggcca gtttgcaagc   23400
caggggtgcc tggggtctg gaggatcagc cccatgttca aggtgaggc ctgggcgggg    23460 cactcgctca cacatacaca aacacacaac ggcctctgag ggccgtgcca actcgcccat   23520
ctgtacaaac atggctgacc tctgtagagc cctgatgctg accccaagcc ccacatcaac   23580
ggcctaagcc atggatgcat gctgggaccc atgtttactt ggctgccacc ctcccctcct   23640
accacgtgta cacacaaaac tcctttgcgc cacccccgc caacttaccc ctaccaagac    23700
cttgacctgg ccttcctttg gccctccatc tcagcctgcc ccttgggccc ttagaaatta   23760
ttaacctcgg gccaggcaca gtggctcacg cctgtaatcc cagcactttg ggaggccaag   23820
gcaggcagat cacctgaggt caggagtttg agaccagcct gaccaacatg gagaaacccc    23880
atcttggccg ggcgcggtgg cttacccctg taatcccagc actttgggag gccaaggcag   23940
gcggatcaca aggtcaggag atcaagacca tactggctaa tacggtgaaa ccctgtctct   24000
actaaaaata caaaaacaaa attagcttgg tgtggtggca ggtgcctgca gtcctagcta   24060 ctctggggc tgaggcggga gaatggcgtg aacccgggag gcagagcttg tagtgagcca    24120
agatcatgcc acagcactcc agcctgggcg acagagggag actccatgtc aaaaaaaaaa  24180 aaaggaaac cccatctcta ctaaaaatac aaaattatcc agatatggtg gcgcatgcct    24240
ctaatcccag ctactcggga ggctgaggca ggagaatcgc ttgaacctgg gaggcggagg   24300
ttgcagtgag ccgagatcgc gccattgcac tccagcctgg gcaagaaaag caaaaactcc   24360
gtctcaaaaa aaaaaaaaaa aaaaaaaaag gccgggcgcg gtggctcacg cctgtaatcc   24420
cagcacttcg ggaggccgag gcaggcggat cacgaggtca ggagatcaag accatcctgg   24480
ctaacacagt gaaaccccgt ctctactaaa aatacaaaaa aattagccag gcgtggtggt   24540
gggcgcctgt agtcccagct actcggtagg ttgaggcagg agaatggcat gaacccagga   24600
ggtggagctt gcagtgagcc aagattccgc cactgcactc cagcctgggt gtcagagcct   24660
gggcaacaga gctagactcc atctcaaaaa aaaaaaaaga aagaaaaga aaaaaaagaa    24720 attattaacc tcacctcctc ctgctggatg ctgaggctcc tccccccacc cctcccctcc   24780
tgcaggagtg ggctatggta tgatggtggt gtccacctac atcggcatct actacaatgt   24840
ggtcatctgc atcgccttct actacttctt ctcgtccatg acgcacgtgc tgccctgggc   24900
ctactgcaat aaccccctgga acacgcatga ctgcgccggt gtactggacg cctccaacct   24960
caccaatggc tctcggccag ccgccttgcc cagcaacctc tcccacctgc tcaaccacag   25020
cctccagagg accagcccca gcgaggagta ctggaggtga ggcacctgca ggacctgggg   25080 tgggggggaac ctggtggcaa ccctgtcccc actgggcaac catctgaaga caaagtaggg  25140
tgcctgctgc aggttcagcc cgctgctggg ctggagagg gtagaggtga gtgaagagtt   25200
taggagaaga gcctgatgta cagaaagcaa tggaagatgg aggccgggca cggtggctca   25260
tgcctgtaat cccagcactt tgggaggccg aggcgggcag atcacgaggt caggagatcg   25320
agaccatcct ggctaacacg gtgaaaccct gtctctacta aaaatacaaa aagagaaaag   25380
```

```
aattagccgg gcgtggtggc aggcacagga gaatggcgtg aacccgggag gcagagcttg    25440
caatgagctg agatcgcgcc actgcacttc agcctgggcg acagagcaag actccatctc    25500
aaaaaaaaaa aaaaaagaaa gaaagcaatg gaagatggaa tgttgagttg caggatcttt    25560
acagagtagc cgtgaggaag gccgtcagaa atccagcaaa ccagccttca gaggagactc    25620
aggggaaagg ggggcagatc ctggggagaa gaagagtgtg ggcaaaggct ctgtcccaga    25680
tgagcagagg ctggccccaa agctgaaggg agcctactct gatgagagta acaggtgtgg    25740
ggagaatgca tgggcttcag gtggcctagg aagtggcact gccttcataa agaacttgcc    25800
aggattaggc ttagacttga tgcagaacaa aagacgccat ggaaggtctc tgagccgggg    25860
gtgccgtgat caagacatcc tggcacattt tgttcagagg cgacagagac cagagtctca    25920
ggccatcctg ctgtgccctc cacccaccag ttggaaattc cctgtgtctt gctggggaac    25980
ccctgggcag agggctttgg gggcatgctg gcaggcctcc accatttatt ccacaacatt    26040
cacgcctctg ctctgccagg ccctgtgtcc ccatggtagg tatgaacagc ccagagcccc    26100
tgtcctgagg agctcacagg gcagtgggga gacagattgc taatcacagt agggcaagtg    26160
cctcggtcca ggtatgtgca ggggtgtcac agagacacaa agaggtagtg cttggtgcta    26220
aggggatggg gcaagaccag gcagtcgagg cttcccagag aagggagaga ggaaagtaga    26280
gagattggga accacatgag caggtgagca gaggccagaa ggaggcaaac tggagctggg    26340
gttgggagca ggtgggacgc tgagtgacaa gacagaagag gccagcaggc atcatataac    26400
acagggcctc ccatgccagg ctaagggttt gaggcttttc tccacatgtg atggaaagcc    26460
atggctgaaa tgtacaaggg tctgaggata ccgcaagtca ccacagggcc tctaaaccca    26520
ggtccaagta ctctgaccct gaaggactca gcttccctgt gccaacctct gggctgggct    26580
gtagacactc aaagacaggt aagacagggc cactattctc aaggaccag agcatagaga    26640 acacagttgc tgtcccccag aggggcatgg gcagactcag gcactcagtt accagacagg    26700
tcatttcatt tgtctttcat tttttaattt ttaacatcct aacatttatt ttcttttttaa    26760 aaaatacacc tggaactgaa tggacagatg atttcttttt tttttttttt ttttttttg    26820 agacagaatc tcgctctgtt gcccaggctg gagtgcagtg gcacgatctc agctcactgc    26880
aacctctgcc tcccgggta agcgattctc ctgcctcagc ctccctagta gctgggatta    26940
caagcacccg ccaccacgcc tggcttgttt ttgtattttt agtagagaca gggtttcaac    27000
atgttggccg ggctggtctc gaactcctga cctcaggtga tccacccacc tcggcctccc    27060
aaagtgctgg ggttacaggc atgagccacc acacccagct gatttcttga gcacctacta    27120
ggtaccaggt actgttctca gaggggagag agggcaggga ggcagacatt gtcctcacgg    27180
agctgccgtc cgatgggaga acgagcagat attgctgagt gaggcgtttt attacatttg    27240
aggcatgatg tggactggtc aacttgatct agtctgggt gatgaacctt tctgaagct    27300 cccagaaaca caaagccttg tgcaacccca ccccagatg ctccagtggt ggttgtccca    27360
gggactgact gccagagatt cccagccctg ggcccaccca gggcaaagct ctagagattt    27420
tatccagtaa aatcagaggg gaagagcctt caaagaaatc tggctggtgg agccgctgca    27480
ctctactccc cagcgcgggc tggagccagg cctgcctaac tggccactgt cccatgcggg    27540
ataccttccc ggcagcacgg ctccctgctg ccctctcctg gagatccagg gaaatggccc    27600
tgaagagagc aacccaggct ggcttcagca agggaggaaa ggaagcaccc ttattgttga    27660
gcacctacta ggtgccaggc atgttatcta agtagatatt agtatccata ttttcagact    27720
```

```
cagaaactgc cgtttagagg ttaaggagct aggcagcagt cgctgtatca gaatctgtgt   27780
gtgttgcgcc cgtctggtgc tgctgttgct gggtgtgccg gggtgaatta ggtggggggtg   27840 gctgtgcagg tgtttagtcc acactctcca atgacccttt ggacagctgc gcgatctcac   27900
tggagtgcca caaaaaccct gttaggtagc ttgtgtaggg attttaaaaa tcaccatttt   27960
acaaatgagg gaagctaatc aaaagtaaga tgaagagact ctaaagcgag agaagctcaa   28020
acggcagatt tctgagccca tgtctgcctc tcacccactc acccttctca ctcagggtcc   28080 tccctccct cgccaccctc ttcacaatct tgccttccag tccctgtgc tggtctgata   28140 cctgctactg ggtcctaaac tcgtgaccag gccttctcac ctctgcggtc cctgtggggc   28200
ccagctcctg tcccccaggg tcttcatggc agctctggag tcacacagac tcctcccaaa   28260
tcctggctct gtcgcatatt agctgtggcc ttgggaggtc gttcacagtc atttgtccat   28320
gaaattgggc agtcgtgata cctacctggt tttaaagaca aaatgagata atgcagccta   28380
aatcactaag actgctgata ggagctcagg cagcacaacc acagccctg tgggacctgt   28440 tcctgagggt cctgttctca aggcactcac cacctggccg gggaaataag atttgtcatg   28500
tggagacatt tttaaagcaa cgcagagtaa ttctggagat gtcatgtgtc aagaggtcac   28560
ttgtaaatac gttgggttcc aaatgtcctt aggctgtttg atctcaaaag catgtggtcc   28620
aaaaccaaaa ccaaacaaaa aacagaatat gatgccctaa aaataaagct agaattcatc   28680
atttggtttc caggctagcc ttttaaactc ttcagtccct aacactgtaa cgctatattc   28740
ttgcagtcaa aaataatata ggccaggtgc ggtggctcat gcctgtaatc ccagcacttt   28800
gggaggctga ggcaggagga ttgcttgagc ccaggcattc gagaccagcc tgggcaatat   28860
ggcgatacca tatctctaca aaaaatacaa aaattagttg gcatggtgg tgcacacatg   28920 tagtcccatc tactcgggag gctgaggtgg gaggatcgat tgagactggg aggtcgaggc   28980
tgcagtgagc catgattgtg ccattgcact ccagcctggg ctatagagca agaccctgtc   29040
tcaataataa taatataaaa cactacctgt ttagcatata tggttagaca aagtattaaa   29100
aaatccttca ggccaggcgt ggtggctcac gcctgtaatc ccagcacttt gggaggctga   29160
ggcaggtggg tcacctgagg tcaggagttt gagaccagcc tggccaacat ggtgaaatcc   29220
ccatctctcc taaaaataca aaaattagcc cagcgtattg gtgcatacct gtaatcccag   29280
ctactcggga ggctgaggca ggagaatcgc ttgaacctgg gagacggagg ttgcagtgag   29340
cccagatcgc acgaatgcac tccagcctgg gtgacagagc aagactgtgt caaaaaaaaa   29400
aaaaatcctt caaacaagaa atggtttctt tactttgaat gctggtgctg gaggtagagc   29460
agttgttctt tgccctcttc cctgagggct ggggagatgc ccctgcaggc ctgtatgccc   29520
agcacttagc acaggcccgg gcacgtaaat gtctgattga tcaaaagatc acagctggta   29580
tgacataggg tgccagatgg agccacccag aggggagaaa tttgggtcca atctttttt   29640 tttttttttt ttttttgag attggacttt tgctttgttg cccaggctag agtgcagtgg   29700
cacaatctcc actccctgca acctccacct cctgggttca agcagttctc ctgcctcagc   29760
ctcccgagta gctgggatta caggcacccg ccatcatggc cggctaattt ttgtagagac   29820
ggggtttcac catattggcc aggctggtct tgaactcctg acttcaggtg atccacccac   29880
cacggcctcc caaagtgctg ggattacagg tgtgagccac cacacccagc cagggtccaa   29940 tcttttactga gcattccact gcttccctca atttatcaga gatagagcta attggtgcac   30000
gtgaaatgct cactggtggc ttcctggagg aggtgacacc tgacagaatg aggaaaaggc   30060
attcctgaag ggagaagtgt gcaaacaagg acctgggctg agcccaactg gggacaagga   30120
```

```
gatctcctcg cccaggaact aggaagacca cccaagcctg gggtgtggcc tccaggagcc   30180
cttgaagggc ctgggaaagg ctgcagagca gtggactgtg ttgggctccc caggggctgc   30240
agcaggtgga ggggactggg ccggccaggg ctgggcccct gaagtagctc ccatgtcaca   30300
caaggtggct gctgggacct catgacaaag gagggtacag cccgggtggg ccctgggcct   30360
tgggaatttg ttgctgggca gcggcggctg gccctcagtg acagagtctc cccttcccag   30420
gctgtacgtg ctgaagctgt cagatgacat tgggaacttt ggggaggtgc ggctgcccct   30480
ccttggctgc ctcggtgtct cctggttggt cgtcttcctc tgcctcatcc gagggtcaa   30540 gtcttcaggg aaagcaagta cccctcccca gcagggtctg tgcccaccca gaaagaccct   30600
gccccctacc tgggttatgt gtgtattgca gggaggggat gctgaaggga ctccggagcc   30660
ggagagggac caggggctg tggtgatta gggagccagg gtggtggtgc ccaggggagg   30720
ggagagccca gaagagtcca tggagccctc ttgtgccagg tggtgtactt cacgccacg   30780 ttcccctacg tggtgctgac cattctgttt gtccgcggag tgaccctgga gggagccttt   30840
gacggcatca tgtactacct aaccccgcag tgggacaaga tcctggaggc caaggtggga   30900
agtgagggaa accggaaggg ggctggggag gggccaggga ggtgcctgcc tctgcccaca   30960
gctcctcacc caccggtcct tccctgcagg tgtggggtga tgctgcctcc cagatcttct   31020
actcactggg ctgcgcgtgg ggaggcctca tcaccatggc ttcctacaac aagttccaca   31080
ataactgtta ccggtgagtg ctccctgctg ggctgaggct gcccccttcc tgcactctct   31140
gcagcctgat ctcagctcca gtgcagccat gggcccacga ggcctccttt ccctcatga   31200 tcttgaggtt ctgggaatac tggttctgga taaagttgtt ggagaatgag gagagaggtt   31260
taggcaggag agagaagaga gatagggaca gtgatgtccc aggggtctgt gaggactcag   31320
gcagctcagg ctccttaaaa atgcccagaa cagaccagaa aaggagttgg gggccaggct   31380
cagtgcttca cgccgtaatc ccagcacttt gagaggccaa ggcgggagga tcacttgagc   31440
ccaggaattc aagacaagcc tgggcagcat agtgagaccc catctttctt tataaaacat   31500
aaaaaagaaa attagctggg tgtggtggca cacacctgta gtcccagcta cttaggaggc   31560
tgaggtggga ggattgcttg agaccaagag gtcaaggcta cagttagctg tgatagcgcc   31620
attgcactcc atcctggaca acagagtgag accctgtctc ccactccaaa aaaaagagt   31680 tgggggtgcc tttgtaccta gaactttccg tgtctccatg tctcctcttg gcccaaattg   31740
gggagaggga agctgaactc tgttttcctc cccatcaggg acagtgtcat catcagcatc   31800
accaactgtg ccaccagcgt ctatgctggc ttcgtcatct tctccatcct cggcttcatg   31860
gccaatcacc tgggcgtgga tgtgtcccgt gtggcagacc acggccctgg cctgccttc   31920 gtggcttacc ccgaggccct cacactactt cccatctccc cgctgtggtc tctgctcttc   31980
ttcttcatgc ttatcctgct ggggctgggc actcaggtac gaggtgcagg acgtggaccg   32040
gaggcttggg gaagggaggg gacaggaaca aggggcaggt ctccgatctg acagccacat   32100
cctgcagttc tgcctcctgg agacgctggt cacagccatt gtggatgagg tgggaatga   32160 gtggatcctg cagaaaaaga cctatgtgac cttgggcgtg gctgtggctg gcttcctgct   32220
gggcatcccc ctcaccagcc aggtaagagc tgcgtaaggg aagggctggc ccagagttgc   32280
caggacgtgc agggaagggt tggggagccc gggctgcagg cgcctccac agctgcccgc   32340 tgttccccag gcaggcatct attggctgct gctgatggac aactatgcgg ccagcttctc   32400
cttggtggtc atctcctgca tcatgtgtgt ggccatcatg tacatctacg gtgagcactc   32460
```

-continued

```
gagcctccgg cctcccgcga cccggccctt ggcccgccca ctctgtcctg cgggtctgct   32520
gaccccccat ctctccaggg caccggaact acttccagga catccagatg atgctgggat   32580
tcccaccacc cctcttcttt cagatctgct ggcgcttcgt ctctcccgcc atcatcttcg   32640
tgagttccct ggccggcccc tcccttcccc cgctgccccat tggccatgtg tccatctctt   32700
gggacccagc ggagggacag tgggagctcc cgcacctggc cggagctcca tacccatgac   32760
tctggccttt ggaggctga gggaggttgg agagagtcag agaggcgtgt ggcgactcag     32820
agctgcctgg gccctggcct caggttagga ggggagtgcc acagccttta tttgactgca   32880
gacgttgctc aggcattcct gcctggcacc cccggggact caggagtcaa tatcgatagc   32940
gtgtcagcct ctgcctgctg gccttatctc ccatccctcc agggagggtg ttccagggcc   33000
ttggctatgt ggtgggaacc agtgttccag cagcagccca aggctggtag accagactgt   33060
ggagtcagag gtcagctctg catggggggca actttgcaag ccttccaggc agtgaggtgg   33120
gtggcttggg aaggggagtt ccaggtttta tgaatattca acagctgaga aattcccatc   33180
agggagctga attggtggaa ggaatccacc atggcaagga agcaggcact ttccacacac   33240
cattcccatg taacccgtga tagagctctc caaggtgtca ttgttgtccc cactttacag   33300
atgaggaaac tgaggcatgg ggatgttaag taattggccc atggtcacac agctaataag   33360
aggcagagcc acaattcaaa tcaggttgtc caattccaag cctgggccag cgccacacta   33420
gaaacacctc tgcaggaggg aggaatggtc caggggccaa aaccgtatga cttggctcct   33480
tcctgtttgg ggtgggattc ggggaaggca ggtattgaca gtgtaatggt cactccacag   33540
aggacaggca aggccacctc tgagtgatag tcagagggct ggcccagtgg cccggccagt   33600
gttcagagcc acactcttgt catgtttaat gcctcggtgg cacaggggggc tcagcaccag   33660 acttcccctg tggctcatgt ttctgaataa aggcccgtgg agggctgagg cctctacccg   33720
gtaggttgtg ggatgttccc gagcctggca caggctcccc gctctggcca ctggcccagc   33780
tttgaaacag gaggaacgga agtctcagtg gtgggaggca ggggagggca ggcaccacca   33840
ccccagagtg ccatgccttc tggggctatg gcccaagggg agctcagcct ctgcggctca   33900
gagggtctcc cagcattcag actagattga tgtcctgggg agagaccagg gggcacctgc   33960
caagggcagt ggggaggaag gagacaagca caagaaggat ctgtaggggc aaccttggct   34020
gggatctggt gtctccacaa gattgaggca cagcgggcgg ggctcttcct gtgcccagga   34080
agccaggctg gagttacctt taggggagcc tagagtcctc tccttggggt aactccagcc   34140
tggctttctg ggctgttgtg ttttctctgg gggctttcct ttttcatatt tctgaaaagc   34200 tcttttttgac aaaactccacc cttctgtcag ctcaaatgag ggatttgtcc acacgtaggt   34260
caggatctgt tccattcagg aaacctgtta taagctccca tcgtgtgcag tgtctccgga   34320
gggtccccca atttggatgt gggtcttgca ttctagaata tggccctgtg ctccaggatg   34380
tggctggagg ctcaggagga gggtgctggg actgccccc ccttcccccc gccaggccct   34440
ctgggtggcc cgccagccac tgcctgtgtt tctgcctcct ttcactcctt ttgttactgc   34500
agccacaagt tttatttcca atctcactca tctctttcca aggaggttcc ctagagcacc   34560
gcagcctgac actcaccatt tctagcccat ggagcttccc caggctgaat gtccctgtct   34620
ccacggccat agacaggcag ggctttgccc taccctcttt ccatcctcct ctgcctctct   34680
gcacaaatca gttcaaatca acacaagaga ctgtggcagg cactgtactg ggcactgcac   34740
ccccagagtt gatgcaattc caggagctct caggtctatg ggaacgttaa accaagtcac   34800
tctaagggaa gcaggtggaa aacgccgtgg ggaggccctg cagaaggaaa tggaggaaat   34860
```

```
ctgggatggc tttttgaagg agagggcact gacatagggt ttgacagagg aagatgcaga    34920
ggatgattcc ccagaataaa tgaagagtgg gtgggaaaca ctgggtgtga ctgaaacact    34980
gagggcggag tagtgtggcc ggcaagacaa tttgaggtca cactgccagg tgacagccta    35040
aaggcccagg atgtggcctt acttcagtta gccatgggga gccatagcga gcagaactga    35100
ctgattccaa aggcggcagc agctctactg tgcttggcca gttcaggact gtggcaaaga    35160
cagacttctc ccttccgcag agccttccca ctcaccgcgc tccggccccc ggccctgcct    35220
gcttcttcca cggcccagat gttgacagct gtccctgttc tgccccaaat gcccttttct    35280
agtttgggaa accagagagg aaagggtgct ggtagaggga tggcctgggg tctgggctct    35340
gggtcggcct cacgcccact cccacacctg ccccgtgcag tttattctag ttttcactgt    35400
gatccagtac cagccgatca cctacaacca ctaccagtac ccaggctggg ccgtggccat    35460
tggcttcctc atggctctgt cctccgtcct ctgcatcccc ctctacgcca tgttccggct    35520
ctgccgcaca gacggggaca ccctcctcca ggtgagggca gggacaggct gggtagccag    35580
gcaaaatggg aggggccagc tggaagggge ttaaggcgct cctcctgacg tgccctgccc    35640
ctgtgcccca tgcctacctc atgcagcgtt tgaaaaatgc cacaaagcca agcagagact    35700
ggggccctgc cctcctggag caccggacag ggcgctacgc ccccaccata gcccctctc    35760
ctgaggacgg cttcgaggtc cagccactgc acccggacaa ggcgcagatc cccattgtgg    35820
gcagtaatgg ctccagccgc ctccaggact cccggatatg agcacagctg caggggagt    35880
ggccccaccc ccacccgtg ctcccaccgc agagactggt gaggcagagg ccaggtgtct    35940
ctgcctgccc cctgccacgc cctggccagg acggctgctg tcaccttggt caccactgct    36000
agtgcagtca ttcatgctca tgtccccagt gtttacatgt cctttggatg ccaagatagc    36060
agctgggggg aggggtggga gtggagggtt gctgggaggt ccaaagcact ttggagggt    36120
ctcgggccag gtccccagca gcctggatgg ctttacgtgg cctccgatac ccttatacc    36180
tgccctgagc tgaggttctg ggtgggcctc cagccccatg actagtgctc ctgccctcag    36240
agccgacccc agcctctgcc aggcacattt ggctattcct ccctaggggc aggatgaagg    36300
gctgggggac tgcccagtgt tacttgtcag gctgtgctgc ccagccctgt ttatctgtgt    36360
aattatttt gtaaacattg tattctctgt ggtcgccacc tcctcgcccc cagcctcggg    36420
ttcagtctgt cttccaggcc tgcttgcacc tcactgggct gctccggggt ctctgcccct    36480
cattccaggc ctggctgtca ggcccagcca gcagggccc gtgacccagc agcctgccca    36540
aagcatttgt ttctggggga tggggtgggg gctgctccac aggaggtttg agcccagcac    36600
cctggggaag gggaccctgc acgacacccc cttgccctcc ctccatgagg ctaaaggccc    36660
agtcttccca aatgtgctgc cctcgttcat gtgccaaatg gccccagccc acatgcccct    36720
cccctctctg gagtgggagc cccttctgaa gtgtctgaat ccctgaagtg ttcatttgtc    36780
cgtcctctgt gcagtgacag ccccggccaa gccacctcta atcctctgta gcaataacgg    36840
tgcgccgccc atccctgccc attgtgcacc actaggattt taaagtccat agattttaat    36900
gaaatttcta ttcctgtctc tgagcggctg ctgtgctttg tctgggtccc ccaggggaca    36960
agagtcaggc tggaatgaga cctctgtctg ccaggccttt gtggaggcct gggaggagaa    37020
aggccaaagg ctttgatgct tgggaccgat gcccggccac tcagctccag acaccaggga    37080
tctggcaagg gggtgggca agggccagac agaccaacag ccttgggtc ctggcgagag    37140
ctcgccaaga ccagatctga agctggctgg gccaaagcag ctgaggcggc agcggcagac    37200
```

```
aggtgcgctg tggcagaagc cagagcctac tcggtgacca gcccttcagg ctggggcttg    37260
gggtgctgca ctggacatgg gtgtggaagc tggcccttcc ctggggctgc actgaagctg    37320
ccgtccccag cggtgggtag ccgactggcc tcgaggtcga aggtagggct ccagaggagg    37380
tgcaggcagg cagcactgga gaggtgcaac cccgcagagg ggaagcgggg gtctgaggcc    37440
ctgtgtggag gaccccaagg gccgctgcct ggacaagaaa gagtaactgt gaggggtggt    37500
ggtctgatcc ttcagtccac cctgccctgt gtctactgtt gtggtttacc tgtggttggg    37560
agagacacaa gaaggcccca cagatgcctg cagctcctgc tccatggcct tcttctgttc    37620
ctttagctct gaaggagaga ttgggctgag acagtgccca gctcttctag ggtgtgtaca    37680
agtgtggggt gggagcagga ggctgggtgt tctgggccct gctccgtgtc ctcacctgcc    37740
agggtgggct ccagggctgc ctcagagggg tggcaaggcc tcaaatactc ctcttccagg    37800
cagcgctgca gggagagctg cgtcagtgcc cagactcaag gcaggggtgg ggcaaggcag    37860
gatacagagg ccaagatccc cagggcagg                                      37889

<210> SEQ ID NO 2
<211> LENGTH: 106
<212> TYPE: DNA
<213> ORGANISM: Homo sapiens

<400> SEQUENCE: 2
aacattttcc agggtccagg gcaagtgccc gcatgggctg ggagccggtg tgtcctcatc    60
cctggacgcc ggggacgggt ggagatgtca gcggatgaca gcgagg                   106

<210> SEQ ID NO 3
<211> LENGTH: 225
<212> TYPE: DNA
<213> ORGANISM: Homo sapiens

<400> SEQUENCE: 3
acagcagtgc tgagatacca agagtggaag tggcttgccc agggctctac tggaggagcg    60
ggccctagag caccagggct ctcacctgca ccggtgtccc gcctctgcca agcccagggc    120
tgagtgggag atctggattc tgccctcgga gctgagcagc cttaattcca ggggctcagc    180
cagagcagta aataagccaa gcagagggct gtgtaaagga cttat                    225

<210> SEQ ID NO 4
<211> LENGTH: 94
<212> TYPE: DNA
<213> ORGANISM: Homo sapiens

<400> SEQUENCE: 4
ggtccagggc aagtgcccgc atgggctggg agccggtgtg tcctcatccc tggacgccgg    60
ggacgggtgg agatgtcarc ggatggcarc gagg                                94

<210> SEQ ID NO 5
<211> LENGTH: 155
<212> TYPE: DNA
<213> ORGANISM: Homo sapiens

<400> SEQUENCE: 5
ggtccagggc aagtgcccgc atgggctggg agccggtgtg tcctcatccc tggacgccgg    60
ggacgggtgg agatgtcagc ggatggcagc gagggtgagg agactcgaaa gctacacttc    120
tcccctgtag gacatcctga cttgaccttc aaaag                               155
```

<210> SEQ ID NO 6
<211> LENGTH: 74
<212> TYPE: DNA
<213> ORGANISM: Homo sapiens

<400> SEQUENCE: 6
aatggtgctg tgcccagcga ggccaccaag agggaccaga acctcaaacg gggcaactgg    60
ggcaaccaga tcga                                                      74

<210> SEQ ID NO 7
<211> LENGTH: 71
<212> TYPE: DNA
<213> ORGANISM: Homo sapiens

<400> SEQUENCE: 7
aatctcgctc tgttgcccag gctggagtgc agtggcacga tctcagctca ctgcaacctc    60
tgcctcccgg g                                                         71

<210> SEQ ID NO 8
<211> LENGTH: 96
<212> TYPE: DNA
<213> ORGANISM: Homo sapiens

<400> SEQUENCE: 8
gcatctattg gctgctgctg atggacaact atgcggccag cttctccttg gtggtcatct    60
cctgcatcat gtgtgtggcc atcatgtaca tctacg                              96

<210> SEQ ID NO 9
<211> LENGTH: 371
<212> TYPE: DNA
<213> ORGANISM: Homo sapiens

<400> SEQUENCE: 9
agccttccca ctcaccgcgc tccggccccc ggccctgcct gcttcttcca cggcccagat    60
gttgacagct gtccctgttc tgccccaaat gccttttct agtttgggaa accagagagg    120
aaagggtgct ggtagaggga tggcctgggg tctgggctct gggtcggcct cacgcccact   180
cccacacctg ccccgtgcag tttattctag ttttcactgt gatccagtac cagccgatca   240
cctacaacca ctaccagtac ccaggctggg ccgtggccat tggcttcctc atggctctgt   300
cctccgtcct ctgcatcccc ctctacgcca tgttccggct ctgccgcaca gacggggaca   360
ccctcctcca g                                                        371

<210> SEQ ID NO 10
<211> LENGTH: 2136
<212> TYPE: DNA
<213> ORGANISM: Homo sapiens
<220> FEATURE:
<221> NAME/KEY: 5'UTR
<222> LOCATION: 1..182
<220> FEATURE:
<221> NAME/KEY: CDS
<222> LOCATION: 183..2084
<220> FEATURE:
<221> NAME/KEY: 3'UTR
<222> LOCATION: 2085..2104

<400> SEQUENCE: 10
agagcctcgg gaggctgatg caactttccc tttaagaaag ccacctgggc gcaccgcggt    60
gcggacccag cacgcctggg ccggggggctg cagcatgctc ttgagatctg tggcctgaaa   120
ggcgctggaa gcagagcctg taagtgtggt ccccgtcacc agagccccaa cccaccgccg   180

-continued

```
cc atg gta gga aaa ggt gcc aaa ggg atg ctg aat ggt gct gtg ccc        227
   Met Val Gly Lys Gly Ala Lys Gly Met Leu Asn Gly Ala Val Pro
   1               5                  10                 15 agc gag gcc acc aag agg gac cag aac ctc aaa cgg ggc aac tgg ggc       275
Ser Glu Ala Thr Lys Arg Asp Gln Asn Leu Lys Arg Gly Asn Trp Gly
                20                 25                 30 aac cag atc gag ttt gta ctg acg agc gtg ggc tat gcc gtg ggc ctg       323
Asn Gln Ile Glu Phe Val Leu Thr Ser Val Gly Tyr Ala Val Gly Leu
            35                 40                 45 ggc aat gtc tgg cgc ttc cca tac ctc tgc tat cgc aac ggg gga ggc       371
Gly Asn Val Trp Arg Phe Pro Tyr Leu Cys Tyr Arg Asn Gly Gly Gly
        50                 55                 60 gcc ttc atg ttc ccc tac ttc atc atg ctc atc ttc tgc ggg atc ccc       419
Ala Phe Met Phe Pro Tyr Phe Ile Met Leu Ile Phe Cys Gly Ile Pro
    65                 70                 75 ctc ttc ttc atg gag ctc tcc ttc ggc cag ttt gca agc cag ggg tgc       467
Leu Phe Phe Met Glu Leu Ser Phe Gly Gln Phe Ala Ser Gln Gly Cys
80                 85                 90                 95 ctg ggg gtc tgg agg atc agc ccc atg ttc aaa gga gtg ggc tat ggt       515
Leu Gly Val Trp Arg Ile Ser Pro Met Phe Lys Gly Val Gly Tyr Gly
                   100                105                110 atg atg gtg gtg tcc acc tac atc ggc atc tac tac aat gtg gtc atc       563
Met Met Val Val Ser Thr Tyr Ile Gly Ile Tyr Tyr Asn Val Val Ile
               115                120                125 tgc atc gcc ttc tac tac ttc ttc tcg tcc atg acg cac gtg ctg ccc       611
Cys Ile Ala Phe Tyr Tyr Phe Phe Ser Ser Met Thr His Val Leu Pro
           130                135                140 tgg gcc tac tgc aat aac ccc tgg aac acg cat gac tgc gcc ggt gta       659
Trp Ala Tyr Cys Asn Asn Pro Trp Asn Thr His Asp Cys Ala Gly Val
       145                150                155 ctg gac gcc tcc aac ctc acc aat ggc tct cgg cca gcc gcc ttg ccc       707
Leu Asp Ala Ser Asn Leu Thr Asn Gly Ser Arg Pro Ala Ala Leu Pro
160                165                170                175 agc aac ctc tcc cac ctg ctc aac cac agc ctc cag agg acc agc ccc       755
Ser Asn Leu Ser His Leu Leu Asn His Ser Leu Gln Arg Thr Ser Pro
                   180                185                190 agc gag gag tac tgg agg ctg tac gtg ctg aag ctg tca gat gac att       803
Ser Glu Glu Tyr Trp Arg Leu Tyr Val Leu Lys Leu Ser Asp Asp Ile
               195                200                205 ggg aac ttt ggg gag gtg cgg ctg ccc ctc ctt ggc tgc ctc ggt gtc       851
Gly Asn Phe Gly Glu Val Arg Leu Pro Leu Leu Gly Cys Leu Gly Val
           210                215                220 tcc tgg ttg gtc gtc ttc ctc tgc ctc atc cga ggg gtc aag tct tca       899
Ser Trp Leu Val Val Phe Leu Cys Leu Ile Arg Gly Val Lys Ser Ser
       225                230                235 ggg aaa gtg gtg tac ttc acg gcc acg ttc ccc tac gtg gtg ctg acc       947
Gly Lys Val Val Tyr Phe Thr Ala Thr Phe Pro Tyr Val Val Leu Thr
240                245                250                255 att ctg ttt gtc cgc gga gtg acc ctg gag gga gcc ttt gac ggc atc       995
Ile Leu Phe Val Arg Gly Val Thr Leu Glu Gly Ala Phe Asp Gly Ile
                   260                265                270 atg tac tac cta acc ccg cag tgg gac aag atc ctg gag gcc aag gtg      1043
Met Tyr Tyr Leu Thr Pro Gln Trp Asp Lys Ile Leu Glu Ala Lys Val
               275                280                285 tgg ggt gat gct gcc tcc cag atc ttc tac tca ctg gcg tgc gcg tgg      1091
Trp Gly Asp Ala Ala Ser Gln Ile Phe Tyr Ser Leu Ala Cys Ala Trp
           290                295                300 gga ggc ctc atc acc atg gct tcc tac aac aag ttc cac aat aac tgt      1139
Gly Gly Leu Ile Thr Met Ala Ser Tyr Asn Lys Phe His Asn Asn Cys
```

-continued

|     |     |     | 305 |     |     |     |     | 310 |     |     |     |     | 315 |     |     |     |      |
|-----|-----|-----|-----|-----|-----|-----|-----|-----|-----|-----|-----|-----|-----|-----|-----|-----|------|
| tac | cgg | gac | agt | gtc | atc | atc | agc | atc | acc | aac | tgt | gcc | acc | agc | gtc |     | 1187 |
| Tyr | Arg | Asp | Ser | Val | Ile | Ile | Ser | Ile | Thr | Asn | Cys | Ala | Thr | Ser | Val |     |      |
| 320 |     |     |     |     | 325 |     |     |     |     | 330 |     |     |     |     | 335 |     |      |

```
tat gct ggc ttc gtc atc ttc tcc atc ctc ggc ttc atg gcc aat cac       1235
Tyr Ala Gly Phe Val Ile Phe Ser Ile Leu Gly Phe Met Ala Asn His
                340                 345                 350 ctg ggc gtg gat gtg tcc cgt gtg gca gac cac ggc cct ggc ctg gcc       1283
Leu Gly Val Asp Val Ser Arg Val Ala Asp His Gly Pro Gly Leu Ala
        355                 360                 365 ttc gtg gct tac ccc gag gcc ctc aca cta ctt ccc atc tcc ccg ctg       1331
Phe Val Ala Tyr Pro Glu Ala Leu Thr Leu Leu Pro Ile Ser Pro Leu
    370                 375                 380 tgg tct ctg ctc ttc ttc atg ctt atc ctg ctg ggg ctg ggc act           1379
Trp Ser Leu Leu Phe Phe Phe Met Leu Ile Leu Leu Gly Leu Gly Thr
385                 390                 395 cag ttc tgc ctc ctg gag acg ctg gtc aca gcc att gtg gat gag gtg       1427
Gln Phe Cys Leu Leu Glu Thr Leu Val Thr Ala Ile Val Asp Glu Val
400                 405                 410                 415 ggg aat gag tgg atc ctg cag aaa aag acc tat gtg acc ttg ggc gtg       1475
Gly Asn Glu Trp Ile Leu Gln Lys Lys Thr Tyr Val Thr Leu Gly Val
                420                 425                 430 gct gtg gct ggc ttc ctg ctg ggc atc ccc ctc acc agc cag gca ggc       1523
Ala Val Ala Gly Phe Leu Leu Gly Ile Pro Leu Thr Ser Gln Ala Gly
            435                 440                 445 atc tat tgg ctg ctg ctg atg gac aac tat gcg gcc agc ttc tcc ttg       1571
Ile Tyr Trp Leu Leu Leu Met Asp Asn Tyr Ala Ala Ser Phe Ser Leu
        450                 455                 460 gtg gtc atc tcc tgc atc atg tgt gtg gcc atc atg tac atc tac ggg       1619
Val Val Ile Ser Cys Ile Met Cys Val Ala Ile Met Tyr Ile Tyr Gly
    465                 470                 475 cac cgg aac tac ttc cag gac atc cag atg atg ctg gga ttc cca cca       1667
His Arg Asn Tyr Phe Gln Asp Ile Gln Met Met Leu Gly Phe Pro Pro
480                 485                 490                 495 ccc ctc ttc ttt cag atc tgc tgg cgc ttc gtc tct ccc gcc atc atc       1715
Pro Leu Phe Phe Gln Ile Cys Trp Arg Phe Val Ser Pro Ala Ile Ile
                500                 505                 510 ttc ttt att cta gtt ttc act gtg atc cag tac cag ccg atc acc tac       1763
Phe Phe Ile Leu Val Phe Thr Val Ile Gln Tyr Gln Pro Ile Thr Tyr
            515                 520                 525 aac cac tac cag tac cca ggc tgg gcc gtg gcc att ggc ttc ctc atg       1811
Asn His Tyr Gln Tyr Pro Gly Trp Ala Val Ala Ile Gly Phe Leu Met
        530                 535                 540 gct ctg tcc tcc gtc ctc tgc atc ccc ctc tac gcc atg ttc cgg ctc       1859
Ala Leu Ser Ser Val Leu Cys Ile Pro Leu Tyr Ala Met Phe Arg Leu
545                 550                 555 tgc cgc aca gac ggg gac acc ctc ctc cag cgt ttg aaa aat gcc aca       1907
Cys Arg Thr Asp Gly Asp Thr Leu Leu Gln Arg Leu Lys Asn Ala Thr
560                 565                 570                 575 aag cca agc aga gac tgg ggc cct gcc ctc ctg gag cac cgg aca ggg       1955
Lys Pro Ser Arg Asp Trp Gly Pro Ala Leu Leu Glu His Arg Thr Gly
                580                 585                 590 cgc tac gcc ccc acc ata gcc ccc tct cct gag gac ggc ttc gag gtc       2003
Arg Tyr Ala Pro Thr Ile Ala Pro Ser Pro Glu Asp Gly Phe Glu Val
            595                 600                 605 cag tca ctg cac ccg gac aag gcg cag atc ccc att gtg ggc agt aat       2051
Gln Ser Leu His Pro Asp Lys Ala Gln Ile Pro Ile Val Gly Ser Asn
        610                 615                 620 ggc tcc agc cgc ctc cag gac tcc cgg ata tag cacagctgcc aggggagtgc    2104
Gly Ser Ser Arg Leu Gln Asp Ser Arg Ile
```

```
Gly Ser Ser Arg Leu Gln Asp Ser Arg Ile *
    625                 630 cacccacccc gtgctccacg agagactgtg ag                                      2136

<210> SEQ ID NO 11
<211> LENGTH: 2199
<212> TYPE: DNA
<213> ORGANISM: Homo sapiens
<220> FEATURE:
<221> NAME/KEY: 5'UTR
<222> LOCATION: 1..105
<220> FEATURE:
<221> NAME/KEY: CDS
<222> LOCATION: 106..2169
<220> FEATURE:
<221> NAME/KEY: 3'UTR
<222> LOCATION: 2170..2189

<400> SEQUENCE: 11
gggccggggg ctgcagcatg ctcttgagat ctgtggcctg aaaggcgctg gaagcagagc        60
ctgtgagtgt ggtccccgtc accagagccc caacccaccg ccgcc atg gta gga aaa      117
                                                    Met Val Gly Lys
                                                      1 ggt gcc aaa ggg atg ctg gtg acg ctt ctc cct gtt cag aga tcc ttc        165
Gly Ala Lys Gly Met Leu Val Thr Leu Leu Pro Val Gln Arg Ser Phe
  5              10                  15                  20 ttc ctg cca ccc ttt tct gga gcc act ccc tct act tcc cta gca gag        213
Phe Leu Pro Pro Phe Ser Gly Ala Thr Pro Ser Thr Ser Leu Ala Glu
                 25                  30                  35 tct gtc ctc aaa gtc tgg cat ggg gcc tac aac tct ggt ctc ctt ccc        261
Ser Val Leu Lys Val Trp His Gly Ala Tyr Asn Ser Gly Leu Leu Pro
             40                  45                  50 caa ctc atg gcc cag cac tcc cta gcc atg gcc cag aat ggt gct gtg        309
Gln Leu Met Ala Gln His Ser Leu Ala Met Ala Gln Asn Gly Ala Val
         55                  60                  65 ccc agc gag gcc acc aag agg gac cag aac ctc aaa cgg ggc aac tgg        357
Pro Ser Glu Ala Thr Lys Arg Asp Gln Asn Leu Lys Arg Gly Asn Trp
     70                  75                  80 ggc aac cag atc gag ttt gta ctg acg agc gtg ggc tat gcc gtg ggc        405
Gly Asn Gln Ile Glu Phe Val Leu Thr Ser Val Gly Tyr Ala Val Gly
 85                  90                  95                 100 ctg ggc aat gtc tgg cgc ttc cca tac ctc tgc tat cgc aac ggg gga        453
Leu Gly Asn Val Trp Arg Phe Pro Tyr Leu Cys Tyr Arg Asn Gly Gly
                105                 110                 115 ggc gcc ttc atg ttc ccc tac ttc atc atg ctc atc ttc tgc ggg atc        501
Gly Ala Phe Met Phe Pro Tyr Phe Ile Met Leu Ile Phe Cys Gly Ile
            120                 125                 130 ccc ctc ttc ttc atg gag ctc tcc ttc ggc cag ttt gca agc cag ggg        549
Pro Leu Phe Phe Met Glu Leu Ser Phe Gly Gln Phe Ala Ser Gln Gly
        135                 140                 145 tgc ctg ggg gtc tgg agg atc agc ccc atg ttc aaa gga gtg ggc tat        597
Cys Leu Gly Val Trp Arg Ile Ser Pro Met Phe Lys Gly Val Gly Tyr
    150                 155                 160 ggt atg atg gtg gtg tcc acc tac atc ggc atc tac tac aat gtg gtc        645
Gly Met Met Val Val Ser Thr Tyr Ile Gly Ile Tyr Tyr Asn Val Val
165                 170                 175                 180 atc tgc atc gcc ttc tac tac ttc ttc tcg tcc atg acg cac gtg ctg        693
Ile Cys Ile Ala Phe Tyr Tyr Phe Phe Ser Ser Met Thr His Val Leu
                185                 190                 195 ccc tgg gcc tac tgc aat aac ccc tgg aac acg cat gac tgc gcc ggt        741
Pro Trp Ala Tyr Cys Asn Asn Pro Trp Asn Thr His Asp Cys Ala Gly
            200                 205                 210
```

-continued

| | |
|---|---|
| gta ctg gac gcc tcc aac ctc acc aat ggc tct cgg cca gcc gcc ttg<br>Val Leu Asp Ala Ser Asn Leu Thr Asn Gly Ser Arg Pro Ala Ala Leu<br>215                    220                    225 | 789 |
| ccc agc aac ctc tcc cac ctg ctc aac cac agc ctc cag agg acc agc<br>Pro Ser Asn Leu Ser His Leu Leu Asn His Ser Leu Gln Arg Thr Ser<br>230                    235                    240 | 837 |
| ccc agc gag gag tac tgg agg ctg tac gtg ctg aag ctg tca gat gac<br>Pro Ser Glu Glu Tyr Trp Arg Leu Tyr Val Leu Lys Leu Ser Asp Asp<br>245                    250                    255                    260 | 885 |
| att ggg aac ttt ggg gag gtg cgg ctg ccc ctc ctt ggc tgc ctc ggt<br>Ile Gly Asn Phe Gly Glu Val Arg Leu Pro Leu Leu Gly Cys Leu Gly<br>                  265                    270                    275 | 933 |
| gtc tcc tgg ttg gtc gtc ttc ctc tgc ctc atc cga ggg gtc aag tct<br>Val Ser Trp Leu Val Val Phe Leu Cys Leu Ile Arg Gly Val Lys Ser<br>            280                    285                    290 | 981 |
| tca ggg aaa gtg gtg tac ttc acg gcc acg ttc ccc tac gtg gtg ctg<br>Ser Gly Lys Val Val Tyr Phe Thr Ala Thr Phe Pro Tyr Val Val Leu<br>                  295                    300                    305 | 1029 |
| acc att ctg ttt gtc cgc gga gtg acc ctg gag gga gcc ttt gac ggc<br>Thr Ile Leu Phe Val Arg Gly Val Thr Leu Glu Gly Ala Phe Asp Gly<br>310                    315                    320 | 1077 |
| atc atg tac tac cta acc ccg cag tgg gac aag atc ctg gag gcc aag<br>Ile Met Tyr Tyr Leu Thr Pro Gln Trp Asp Lys Ile Leu Glu Ala Lys<br>325                    330                    335                    340 | 1125 |
| gtg tgg ggt gat gct gcc tcc cag atc ttc tac tca ctg gcg tgc gcg<br>Val Trp Gly Asp Ala Ala Ser Gln Ile Phe Tyr Ser Leu Ala Cys Ala<br>                  345                    350                    355 | 1173 |
| tgg gga ggc ctc atc acc atg gct tcc tac aac aag ttc cac aat aac<br>Trp Gly Gly Leu Ile Thr Met Ala Ser Tyr Asn Lys Phe His Asn Asn<br>            360                    365                    370 | 1221 |
| tgt tac cgg gac agt gtc atc atc agc atc acc aac tgt gcc acc agc<br>Cys Tyr Arg Asp Ser Val Ile Ile Ser Ile Thr Asn Cys Ala Thr Ser<br>                  375                    380                    385 | 1269 |
| gtc tat gct ggc ttc gtc atc ttc tcc atc ctc ggc ttc atg gcc aat<br>Val Tyr Ala Gly Phe Val Ile Phe Ser Ile Leu Gly Phe Met Ala Asn<br>390                    395                    400 | 1317 |
| cac ctg ggc gtg gat gtg tcc cgt gtg gca gac cac ggc cct ggc ctg<br>His Leu Gly Val Asp Val Ser Arg Val Ala Asp His Gly Pro Gly Leu<br>405                    410                    415                    420 | 1365 |
| gcc ttc gtg gct tac ccc gag gcc ctc aca cta ctt ccc atc tcc ccg<br>Ala Phe Val Ala Tyr Pro Glu Ala Leu Thr Leu Leu Pro Ile Ser Pro<br>                  425                    430                    435 | 1413 |
| ctg tgg tct ctg ctc ttc ttc atg ctt atc ctg ggg ctg ggc<br>Leu Trp Ser Leu Leu Phe Phe Phe Met Leu Ile Leu Gly Leu Gly<br>            440                    445                    450 | 1461 |
| act cag ttc tgc ctc ctg gag acg ctg ggc aca gcc att gtg gat gag<br>Thr Gln Phe Cys Leu Leu Glu Thr Leu Gly Thr Ala Ile Val Asp Glu<br>                  455                    460                    465 | 1509 |
| gtg ggg aat gag tgg atc ctg cag aaa aag acc aat atg acc ttg ggg<br>Val Gly Asn Glu Trp Ile Leu Gln Lys Lys Thr Asn Met Thr Leu Gly<br>470                    475                    480 | 1557 |
| cgt gct gtg gct ggc ttc ctg ctg ggc atc ccc ctc acc agc cag gca<br>Arg Ala Val Ala Gly Phe Leu Leu Gly Ile Pro Leu Thr Ser Gln Ala<br>485                    490                    495                    500 | 1605 |
| ggc atc tat tgg ctg ctg ctg atg gac aac tat gcg gcc agc ttc tcc<br>Gly Ile Tyr Trp Leu Leu Leu Met Asp Asn Tyr Ala Ala Ser Phe Ser<br>                  505                    510                    515 | 1653 |
| ttg gtg gtc atc tcc tgc atc atg tgt gtg gcc atc atg tac atc tac<br>Leu Val Val Ile Ser Cys Ile Met Cys Val Ala Ile Met Tyr Ile Tyr | 1701 |

-continued

```
                 520                 525                 530
ggg cac cgg aac tac ttc cag gac atc cag atg atg ctg gga ttc cca      1749
Gly His Arg Asn Tyr Phe Gln Asp Ile Gln Met Met Leu Gly Phe Pro
        535                 540                 545 cca ccc ctc ttc ttt cag atc tgc tgg cgc ttc gtc tct ccc gcc atc      1797
Pro Pro Leu Phe Phe Gln Ile Cys Trp Arg Phe Val Ser Pro Ala Ile
550                 555                 560 atc ttc ttt att cta gtt ttc act gtg atc cag tac cag ccg atc acc      1845
Ile Phe Phe Ile Leu Val Phe Thr Val Ile Gln Tyr Gln Pro Ile Thr
565                 570                 575                 580 tac aac cac tac cag tac cca ggc tgg gcc gtg gcc att ggc ttc ctc      1893
Tyr Asn His Tyr Gln Tyr Pro Gly Trp Ala Val Ala Ile Gly Phe Leu
                585                 590                 595 atg gct ctg tcc tcc gtc ctc tgc atc ccc ctc tac gcc atg ttc cgg      1941
Met Ala Leu Ser Ser Val Leu Cys Ile Pro Leu Tyr Ala Met Phe Arg
            600                 605                 610 ctc tgc cgc aca gac ggg gac acc ctc ctc cag cgt ttg aaa aat gcc      1989
Leu Cys Arg Thr Asp Gly Asp Thr Leu Leu Gln Arg Leu Lys Asn Ala
        615                 620                 625 aca aag cca agc aga gac tgg ggc cct gcc ctc ctg gag cac cgg aca      2037
Thr Lys Pro Ser Arg Asp Trp Gly Pro Ala Leu Leu Glu His Arg Thr
    630                 635                 640 ggg cgc tac gcc ccc acc ata gcc ccc tct cct gag gac ggc ttc gag      2085
Gly Arg Tyr Ala Pro Thr Ile Ala Pro Ser Pro Glu Asp Gly Phe Glu
645                 650                 655                 660 gtc cag tca ctg cac ccg gac aag gcg cag atc ccc att gtg ggc agt      2133
Val Gln Ser Leu His Pro Asp Lys Ala Gln Ile Pro Ile Val Gly Ser
                665                 670                 675 aat ggc tca cgc cgc ctc cag gac tcc cgg ata tag cacagctgcc          2179
Asn Gly Ser Arg Arg Leu Gln Asp Ser Arg Ile *
            680                 685 agggagtgc cacctctaga                                                 2199

<210> SEQ ID NO 12
<211> LENGTH: 2202
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..2151
<220> FEATURE:
<221> NAME/KEY: 3'UTR
<222> LOCATION: 2152..2171

<400> SEQUENCE: 12
gcccacacac cccactccag ctccggagca cccgtgctgg gctgcatggg gactggccgg      60
aggggcaggg ccaggggagc gggtaggcag agcttcggga ggagatgagg tgaaagtaat    120
tgacgctgcc cagcccggca gtgggagagg caggggatgc gtcagtgtcg cgctggagct    180
ggcagaggtg atgagcggcg gagacacgcg gggctgcgat cgctcgcccc agg atg      236
                                                              Met
                                                               1 gcc gcg gct cat gga cct gtg gcc ccc tct tcc cca gaa cag aat ggt      284
Ala Ala Ala His Gly Pro Val Ala Pro Ser Ser Pro Glu Gln Asn Gly
        5                   10                  15 gct gtg ccc agc gag gcc acc aag agg gac cag aac ctc aaa cgg ggc      332
Ala Val Pro Ser Glu Ala Thr Lys Arg Asp Gln Asn Leu Lys Arg Gly
    20                  25                  30
```

-continued

```
aac tgg ggc aac cag atc gag ttt gta ctg acg agc gtg ggc tat gcc        380
Asn Trp Gly Asn Gln Ile Glu Phe Val Leu Thr Ser Val Gly Tyr Ala
         35                  40                  45 gtg ggc ctg ggc aat gtc tgg cgc ttc cca tac ctc tgc tat cgc aac        428
Val Gly Leu Gly Asn Val Trp Arg Phe Pro Tyr Leu Cys Tyr Arg Asn
 50                  55                  60                  65 ggg gga ggc gcc ttc atg ttc ccc tac ttc atc atg ctc atc ttc tgc        476
Gly Gly Gly Ala Phe Met Phe Pro Tyr Phe Ile Met Leu Ile Phe Cys
                     70                  75                  80 ggg atc ccc ctc ttc ttc atg gag ctc tcc ttc ggc cag ttt gca agc        524
Gly Ile Pro Leu Phe Phe Met Glu Leu Ser Phe Gly Gln Phe Ala Ser
             85                  90                  95 cag ggg tgc ctg ggg gtc tgg agg atc agc ccc atg ttc aaa gga gtg        572
Gln Gly Cys Leu Gly Val Trp Arg Ile Ser Pro Met Phe Lys Gly Val
                100                 105                 110 ggc tat ggt atg atg gtg gtg tcc acc tac atc ggc atc tac tac aat        620
Gly Tyr Gly Met Met Val Val Ser Thr Tyr Ile Gly Ile Tyr Tyr Asn
        115                 120                 125 gtg gtc atc tgc atc gcc ttc tac tac ttc ttc tcg tcc atg acg cac        668
Val Val Ile Cys Ile Ala Phe Tyr Tyr Phe Phe Ser Ser Met Thr His
130                 135                 140                 145 gtg ctg ccc tgg gcc tac tgc aat aac ccc tgg aac acg cat gac tgc        716
Val Leu Pro Trp Ala Tyr Cys Asn Asn Pro Trp Asn Thr His Asp Cys
                    150                 155                 160 gcc ggt gta ctg gac gcc tcc aac ctc acc aat ggc tct cgg cca gcc        764
Ala Gly Val Leu Asp Ala Ser Asn Leu Thr Asn Gly Ser Arg Pro Ala
                165                 170                 175 gcc ttg ccc agc aac ctc tcc cac ctg ctc aac cac agc ctc cag agg        812
Ala Leu Pro Ser Asn Leu Ser His Leu Leu Asn His Ser Leu Gln Arg
            180                 185                 190 acc agc ccc agc gag gag tac tgg agg ctg tac gtg ctg aag ctg tca        860
Thr Ser Pro Ser Glu Glu Tyr Trp Arg Leu Tyr Val Leu Lys Leu Ser
        195                 200                 205 gat gac att ggg aac ttt ggg gag gtg cgg ctg ccc ctc ctt ggc tgc        908
Asp Asp Ile Gly Asn Phe Gly Glu Val Arg Leu Pro Leu Leu Gly Cys
210                 215                 220                 225 ctc ggt gtc tcc tgg ttg gtc gtc ttc ctc tgc ctc atc cga ggg gtc        956
Leu Gly Val Ser Trp Leu Val Val Phe Leu Cys Leu Ile Arg Gly Val
                    230                 235                 240 aag tct tca ggg aaa gtg gtg tac ttc acg gcc acg ttc ccc tac gtg       1004
Lys Ser Ser Gly Lys Val Val Tyr Phe Thr Ala Thr Phe Pro Tyr Val
                245                 250                 255 gtg ctg acc att ctg ttt gtc cgc gga gtg acc ctg gag gga gcc ttt       1052
Val Leu Thr Ile Leu Phe Val Arg Gly Val Thr Leu Glu Gly Ala Phe
            260                 265                 270 gac ggc atc atg tac tac cta acc ccg cag tgg gac aag atc ctg gag       1100
Asp Gly Ile Met Tyr Tyr Leu Thr Pro Gln Trp Asp Lys Ile Leu Glu
275                 280                 285 gcc aag gtg tgg ggt gat gct gcc tcc cag atc ttc tac tca ctg gcg       1148
Ala Lys Val Trp Gly Asp Ala Ala Ser Gln Ile Phe Tyr Ser Leu Ala
        290                 295                 300                 305 tgc gcg tgg gga ggc ctc atc acc atg gct tcc tac aac aag ttc cac       1196
Cys Ala Trp Gly Gly Leu Ile Thr Met Ala Ser Tyr Asn Lys Phe His
                    310                 315                 320 aat aac tgt tac cgg gac agt gtc atc atc agc atc acc aac tgt gcc       1244
Asn Asn Cys Tyr Arg Asp Ser Val Ile Ile Ser Ile Thr Asn Cys Ala
                325                 330                 335 acc agc gtc tat gct ggc ttc gtc atc ttc tcc atc ctc ggc ttc atg       1292
Thr Ser Val Tyr Ala Gly Phe Val Ile Phe Ser Ile Leu Gly Phe Met
            340                 345                 350
```

```
gcc aat cac ctg ggc gtg gat gtg tcc cgt gtg gca gac cac ggc cct    1340
Ala Asn His Leu Gly Val Asp Val Ser Arg Val Ala Asp His Gly Pro
355                 360                 365 ggc ctg gcc ttc gtg gct tac ccc gag gcc ctc aca cta ctt ccc atc    1388
Gly Leu Ala Phe Val Ala Tyr Pro Glu Ala Leu Thr Leu Leu Pro Ile
370                 375                 380                 385 tcc ccg ctg tgg tct ctg ctc ttc ttc atg ctt atc ctg ctg ggg        1436
Ser Pro Leu Trp Ser Leu Leu Phe Phe Phe Met Leu Ile Leu Leu Gly
                390                 395                 400 ctg ggc act cag ttc tgc ctc ctg gag acg ctg gtc aca gcc att gtg    1484
Leu Gly Thr Gln Phe Cys Leu Leu Glu Thr Leu Val Thr Ala Ile Val
            405                 410                 415 gat gag gtg ggg aat gag tgg atc ctg cag aaa aag acc tat gtg acc    1532
Asp Glu Val Gly Asn Glu Trp Ile Leu Gln Lys Lys Thr Tyr Val Thr
420                 425                 430 ttg ggc gtg gct gtg gct ggc ttc ctg ctg ggc atc ccc ctc acc agc    1580
Leu Gly Val Ala Val Ala Gly Phe Leu Leu Gly Ile Pro Leu Thr Ser
435                 440                 445 cag gca ggc atc tat tgg ctg ctg ctg atg gac aac tat gcg gcc agc    1628
Gln Ala Gly Ile Tyr Trp Leu Leu Leu Met Asp Asn Tyr Ala Ala Ser
450                 455                 460                 465 ttc tcc ttg gtg gtc atc tcc tgc atc atg tgt gtg gcc atc atg tac    1676
Phe Ser Leu Val Val Ile Ser Cys Ile Met Cys Val Ala Ile Met Tyr
                470                 475                 480 atc tac ggg cac cgg aac tac ttc cag gac atc cag atg atg ctg gga    1724
Ile Tyr Gly His Arg Asn Tyr Phe Gln Asp Ile Gln Met Met Leu Gly
            485                 490                 495 ttc cca cca ccc ctc ttc ttt cag atc tgc tgg cgc ttc gtc tct ccc    1772
Phe Pro Pro Pro Leu Phe Phe Gln Ile Cys Trp Arg Phe Val Ser Pro
500                 505                 510 gcc atc atc ttc ttt att cta gtt ttc act gtg atc cag tac cag ccg    1820
Ala Ile Ile Phe Phe Ile Leu Val Phe Thr Val Ile Gln Tyr Gln Pro
515                 520                 525 atc acc tac aac cac tac cag tac cca ggc tgg gcc gtg gcc att ggc    1868
Ile Thr Tyr Asn His Tyr Gln Tyr Pro Gly Trp Ala Val Ala Ile Gly
530                 535                 540                 545 ttc ctc atg gct ctg tcc tcc gtc ctc tgc atc ccc ctc tac gcc atg    1916
Phe Leu Met Ala Leu Ser Ser Val Leu Cys Ile Pro Leu Tyr Ala Met
                550                 555                 560 ttc cgg ctc tgc cgc aca gac ggg gac acc ctc ctc cag cgt ttg aaa    1964
Phe Arg Leu Cys Arg Thr Asp Gly Asp Thr Leu Leu Gln Arg Leu Lys
            565                 570                 575 aat gcc aca aag cca agc aga gac tgg ggc cct gcc ctc ctg gag cac    2012
Asn Ala Thr Lys Pro Ser Arg Asp Trp Gly Pro Ala Leu Leu Glu His
580                 585                 590 cgg aca ggg cgc tac gcc ccc acc ata gcc ccc tct cct gag gac ggc    2060
Arg Thr Gly Arg Tyr Ala Pro Thr Ile Ala Pro Ser Pro Glu Asp Gly
595                 600                 605 ttc gag gtc cag tca ctg cac ccg gac aag gcg cag atc ccc att gtg    2108
Phe Glu Val Gln Ser Leu His Pro Asp Lys Ala Gln Ile Pro Ile Val
610                 615                 620                 625 ggc agt aat ggc tcc agc cgc ctc cag gac tcc cgg ata tag            2150
Gly Ser Asn Gly Ser Ser Arg Leu Gln Asp Ser Arg Ile *
                630                 635 cacagctgcc aggggagtgc caccccaccc gtgctccacg agagactgtg ag          2202

<210> SEQ ID NO 13
<211> LENGTH: 2364
<212> TYPE: DNA
```

```
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..2313
<220> FEATURE:
<221> NAME/KEY: 3'UTR
<222> LOCATION: 2314..2333

<400> SEQUENCE: 13
gcccacacac cccactccag ctccggagca cccgtgctgg gctgcatggg gactggccgg      60
aggggcaggg ccaggggagc gggtaggcag agcttcggga ggagatgagg tgaaagtaat     120
tgacgctgcc cagcccggca gtgggagagg caggggatgc gtcagtgtcg cgctggagct     180
ggcagaggtg atgagcggcg gagacacgcg gggctgcgat cgctcgcccc agg atg       236
                                                              Met
                                                               1 gcc gcg gct cat gga cct gtg gcc ccc tct tcc cca gaa cag gtg acg       284
Ala Ala Ala His Gly Pro Val Ala Pro Ser Ser Pro Glu Gln Val Thr
             5                  10                  15 ctt ctc cct gtt cag aga tcc ttc ttc ctg cca ccc ttt tct gga gcc       332
Leu Leu Pro Val Gln Arg Ser Phe Phe Leu Pro Pro Phe Ser Gly Ala
         20                  25                  30 act ccc tct act tcc cta gca gag tct gtc ctc aaa gtc tgg cat ggg       380
Thr Pro Ser Thr Ser Leu Ala Glu Ser Val Leu Lys Val Trp His Gly
     35                  40                  45 gcc tac aac tct ggt ctc ctt ccc caa ctc atg gcc cag cac tcc cta       428
Ala Tyr Asn Ser Gly Leu Leu Pro Gln Leu Met Ala Gln His Ser Leu
 50                  55                  60                  65 gcc atg gcc cag aat ggt gct gtg ccc agc gag gcc acc aag agg gac       476
Ala Met Ala Gln Asn Gly Ala Val Pro Ser Glu Ala Thr Lys Arg Asp
                 70                  75                  80 cag aac ctc aaa cgg ggc aac tgg ggc aac cag atc gag ttt gta ctg       524
Gln Asn Leu Lys Arg Gly Asn Trp Gly Asn Gln Ile Glu Phe Val Leu
             85                  90                  95 acg agc gtg ggc tat gcc gtg ggc ctg ggc aat gtc tgg cgc ttc cca       572
Thr Ser Val Gly Tyr Ala Val Gly Leu Gly Asn Val Trp Arg Phe Pro
        100                 105                 110 tac ctc tgc tat cgc aac ggg gga ggc gcc ttc atg ttc ccc tac ttc       620
Tyr Leu Cys Tyr Arg Asn Gly Gly Gly Ala Phe Met Phe Pro Tyr Phe
    115                 120                 125 atc atg ctc atc ttc tgc ggg atc ccc ctc ttc ttc atg gag ctc tcc       668
Ile Met Leu Ile Phe Cys Gly Ile Pro Leu Phe Phe Met Glu Leu Ser
130                 135                 140                 145 ttc ggc cag ttt gca agc cag ggg tgc ctg ggg gtc tgg agg atc agc       716
Phe Gly Gln Phe Ala Ser Gln Gly Cys Leu Gly Val Trp Arg Ile Ser
                150                 155                 160 ccc atg ttc aaa gga gtg ggc tat ggt atg atg gtg gtg tcc acc tac       764
Pro Met Phe Lys Gly Val Gly Tyr Gly Met Met Val Val Ser Thr Tyr
            165                 170                 175 atc ggc atc tac tac aat gtg gtc atc tgc atc gcc ttc tac tac ttc       812
Ile Gly Ile Tyr Tyr Asn Val Val Ile Cys Ile Ala Phe Tyr Tyr Phe
        180                 185                 190 ttc tcg tcc atg acg cac gtg ctg ccc tgg gcc tac tgc aat aac ccc       860
Phe Ser Ser Met Thr His Val Leu Pro Trp Ala Tyr Cys Asn Asn Pro
    195                 200                 205 tgg aac acg cat gac tgc gcc ggt gta ctg gac gcc tcc aac ctc acc       908
Trp Asn Thr His Asp Cys Ala Gly Val Leu Asp Ala Ser Asn Leu Thr
210                 215                 220                 225
```

```
aat ggc tct cgg cca gcc gcc ttg ccc agc aac ctc tcc cac ctg ctc     956
Asn Gly Ser Arg Pro Ala Ala Leu Pro Ser Asn Leu Ser His Leu Leu
            230                 235                 240 aac cac agc ctc cag agg acc agc ccc agc gag gag tac tgg agg ctg    1004
Asn His Ser Leu Gln Arg Thr Ser Pro Ser Glu Glu Tyr Trp Arg Leu
        245                 250                 255 tac gtg ctg aag ctg tca gat gac att ggg aac ttt ggg gag gtg cgg    1052
Tyr Val Leu Lys Leu Ser Asp Asp Ile Gly Asn Phe Gly Glu Val Arg
    260                 265                 270 ctg ccc ctc ctt ggc tgc ctc ggt gtc tcc tgg ttg gtc gtc ttc ctc    1100
Leu Pro Leu Leu Gly Cys Leu Gly Val Ser Trp Leu Val Val Phe Leu
275                 280                 285 tgc ctc atc cga ggg gtc aag tct tca ggg aaa gtg gtg tac ttc acg    1148
Cys Leu Ile Arg Gly Val Lys Ser Ser Gly Lys Val Val Tyr Phe Thr
290                 295                 300                 305 gcc acg ttc ccc tac gtg gtg ctg acc att ctg ttt gtc cgc gga gtg    1196
Ala Thr Phe Pro Tyr Val Val Leu Thr Ile Leu Phe Val Arg Gly Val
            310                 315                 320 acc ctg gag gga gcc ttt gac ggc atc atg tac tac cta acc ccg cag    1244
Thr Leu Glu Gly Ala Phe Asp Gly Ile Met Tyr Tyr Leu Thr Pro Gln
        325                 330                 335 tgg gac aag atc ctg gag gcc aag gtg tgg ggt gat gct gcc tcc cag    1292
Trp Asp Lys Ile Leu Glu Ala Lys Val Trp Gly Asp Ala Ala Ser Gln
    340                 345                 350 atc ttc tac tca ctg gcg tgc gcg tgg gga ggc ctc atc acc atg gct    1340
Ile Phe Tyr Ser Leu Ala Cys Ala Trp Gly Gly Leu Ile Thr Met Ala
355                 360                 365 tcc tac aac aag ttc cac aat aac tgt tac cgg gac agt gtc atc atc    1388
Ser Tyr Asn Lys Phe His Asn Asn Cys Tyr Arg Asp Ser Val Ile Ile
370                 375                 380                 385 agc atc acc aac tgt gcc acc agc gtc tat gct ggc ttc gtc atc ttc    1436
Ser Ile Thr Asn Cys Ala Thr Ser Val Tyr Ala Gly Phe Val Ile Phe
            390                 395                 400 tcc atc ctc ggc ttc atg gcc aat cac ctg ggc gtg gat gtg tcc cgt    1484
Ser Ile Leu Gly Phe Met Ala Asn His Leu Gly Val Asp Val Ser Arg
        405                 410                 415 gtg gca gac cac ggc cct ggc ctg gcc ttc gtg gct tac ccc gag gcc    1532
Val Ala Asp His Gly Pro Gly Leu Ala Phe Val Ala Tyr Pro Glu Ala
    420                 425                 430 ctc aca cta ctt ccc atc tcc ccg ctg tgg tct ctg ctc ttc ttc ttc    1580
Leu Thr Leu Leu Pro Ile Ser Pro Leu Trp Ser Leu Leu Phe Phe Phe
435                 440                 445 atg ctt atc ctg ctg ggg ctg ggc act cag ttc tgc ctc ctg gag acg    1628
Met Leu Ile Leu Leu Gly Leu Gly Thr Gln Phe Cys Leu Leu Glu Thr
450                 455                 460                 465 ctg gtc aca gcc att gtg gat gag gtg ggg aat gag tgg atc ctg cag    1676
Leu Val Thr Ala Ile Val Asp Glu Val Gly Asn Glu Trp Ile Leu Gln
            470                 475                 480 aaa aag acc tat gtg acc ttg ggc gtg gct gtg gct ggc ttc ctg ctg    1724
Lys Lys Thr Tyr Val Thr Leu Gly Val Ala Val Ala Gly Phe Leu Leu
        485                 490                 495 ggc atc ccc ctc acc agc cag gca ggc atc tat tgg ctg ctg ctg atg    1772
Gly Ile Pro Leu Thr Ser Gln Ala Gly Ile Tyr Trp Leu Leu Leu Met
    500                 505                 510 gac aac tat gcg gcc agc ttc tcc ttg gtg gtc atc tcc tgc atc atg    1820
Asp Asn Tyr Ala Ala Ser Phe Ser Leu Val Val Ile Ser Cys Ile Met
515                 520                 525 tgt gtg gcc atc atg tac atc tac ggg cac cgg aac tac ttc cag gac    1868
Cys Val Ala Ile Met Tyr Ile Tyr Gly His Arg Asn Tyr Phe Gln Asp
530                 535                 540                 545
```

| | | |
|---|---|---|
| atc cag atg atg ctg gga ttc cca cca ccc ctc ttc ttt cag atc tgc<br>Ile Gln Met Met Leu Gly Phe Pro Pro Pro Leu Phe Phe Gln Ile Cys<br>550 555 560 | | 1916 |
| tgg cgc ttc gtc tct ccc gcc atc atc ttc ttt att cta gtt ttc act<br>Trp Arg Phe Val Ser Pro Ala Ile Ile Phe Phe Ile Leu Val Phe Thr<br>565 570 575 | | 1964 |
| gtg atc cag tac cag ccg atc acc tac aac cac tac cag tac cca ggc<br>Val Ile Gln Tyr Gln Pro Ile Thr Tyr Asn His Tyr Gln Tyr Pro Gly<br>580 585 590 | | 2012 |
| tgg gcc gtg gcc att ggc ttc ctc atg gct ctg tcc tcc gtc ctc tgc<br>Trp Ala Val Ala Ile Gly Phe Leu Met Ala Leu Ser Ser Val Leu Cys<br>595 600 605 | | 2060 |
| atc ccc ctc tac gcc atg ttc cgg ctc tgc cgc aca gac ggg gac acc<br>Ile Pro Leu Tyr Ala Met Phe Arg Leu Cys Arg Thr Asp Gly Asp Thr<br>610 615 620 625 | | 2108 |
| ctc ctc cag cgt ttg aaa aat gcc aca aag cca agc aga gac tgg ggc<br>Leu Leu Gln Arg Leu Lys Asn Ala Thr Lys Pro Ser Arg Asp Trp Gly<br>630 635 640 | | 2156 |
| cct gcc ctc ctg gag cac cgg aca ggg cgc tac gcc ccc acc ata gcc<br>Pro Ala Leu Leu Glu His Arg Thr Gly Arg Tyr Ala Pro Thr Ile Ala<br>645 650 655 | | 2204 |
| ccc tct cct gag gac ggc ttc gag gtc cag tca ctg cac ccg gac aag<br>Pro Ser Pro Glu Asp Gly Phe Glu Val Gln Ser Leu His Pro Asp Lys<br>660 665 670 | | 2252 |
| gcg cag atc ccc att gtg ggc agt aat ggc tcc agc cgc ctc cag gac<br>Ala Gln Ile Pro Ile Val Gly Ser Asn Gly Ser Ser Arg Leu Gln Asp<br>675 680 685 | | 2300 |
| tcc cgg ata tag cacagctgcc aggggagtgc caccccaccc gtgctccacg<br>Ser Arg Ile *<br>690 | | 2352 |
| agagactgtg ag | | 2364 |

<210> SEQ ID NO 14
<211> LENGTH: 2299
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..789
<220> FEATURE:
<221> NAME/KEY: 3'UTR
<222> LOCATION: 790..2265

<400> SEQUENCE: 14

| | |
|---|---|
| cccacacacc ccactccagc tccggagcac ccgtgctggg ctgcatgggg actggccgga | 60 |
| ggggcagggc caggggagcg ggtaggcaga gcttcgggag gagatgaggt gaaagtaatt | 120 |
| gacgctgccc agcccggcag tgggagaggc agggatgcc tcagtgtcgc gctggagctg | 180 |
| gcagaggtgt gaatgagcgg cggagacacg cgggctgcga tcgctcgccc cagg atg<br>Met<br>1 | 237 |
| gcc gcg gct cat gga cct gtg gcc ccc tct tcc cca gaa cag ggt cca<br>Ala Ala Ala His Gly Pro Val Ala Pro Ser Ser Pro Glu Gln Gly Pro<br>5 10 15 | 285 |
| ggg caa gtg ccc gca tgg gct ggg agc cgg tgt gtc ctc atc cct gga<br>Gly Gln Val Pro Ala Trp Ala Gly Ser Arg Cys Val Leu Ile Pro Gly<br>20 25 30 | 333 |
| cgc cgg gga cgg gtg gag atg tca rcg gat ggc arc gag gaa tgg tgc | 381 |

```
                Arg Arg Gly Arg Val Glu Met Ser Xaa Asp Gly Xaa Glu Glu Trp Cys
                             35                  40                  45 tgt gcc cag cga ggc cac caa gag gga cca gaa cct caa acg ggg caa         429
Cys Ala Gln Arg Gly His Gln Glu Gly Pro Glu Pro Gln Thr Gly Gln
 50                  55                  60                  65 ctg ggg caa cca gat cga gtt tgt act gac gag cgt ggg cta tgc cgt         477
Leu Gly Gln Pro Asp Arg Val Cys Thr Asp Glu Arg Gly Leu Cys Arg
                 70                  75                  80 ggg cct ggg caa tgt ctg gcg ctt ccc ata cct ctg cta tcg caa cgg         525
Gly Pro Gly Gln Cys Leu Ala Leu Pro Ile Pro Leu Leu Ser Gln Arg
             85                  90                  95 ggg agg cgc ctt cat gtt ccc cta ctt cat cat gct cat ctt ctg cgg         573
Gly Arg Arg Leu His Val Pro Leu Leu His His Ala His Leu Leu Arg
         100                 105                 110 gat ccc cct ctt ctt cat gga gct ctc ctt cgg cca gtt tgc aag cca         621
Asp Pro Pro Leu Leu His Gly Ala Leu Leu Arg Pro Val Cys Lys Pro
     115                 120                 125 ggg gtg cct ggg ggt ctg gag gat cag ccc cat gtt caa agg agt ggg         669
Gly Val Pro Gly Gly Leu Glu Asp Gln Pro His Val Gln Arg Ser Gly
130                 135                 140                 145 cta tgg tat gat ggt ggt gtc cac cta cat cgg cat cta cta caa tgt         717
Leu Trp Tyr Asp Gly Gly Val His Leu His Arg His Leu Leu Gln Cys
                 150                 155                 160 ggt cat ctg cat cgc ctt cta cta ctt ctt ctc gtc cat gac gca cgt         765
Gly His Leu His Arg Leu Leu Leu Leu Leu Val His Asp Ala Arg
             165                 170                 175 gct gcc ctg ggc cta ctg caa taa ccc ctggaac acgcatgact gcgccggtgt      819
Ala Ala Leu Gly Leu Leu Gln  *
         180                 185 actggacgcc tccaacctca ccaatggctc tcggccagcc gccttgccca gcaacctctc      879
ccacctgctc aaccacagcc tccagaggac cagccccagc gaggagtact ggaggctgta      939
cgtgctgaag ctgtcagatg acattgggaa ctttggggag gtgcggctgc cctccttgg      999 ctgcctcggt gtctcctggt tggtcgtctt cctctgcctc atccgagggg tcaagtcttc     1059
agggaaagtg gtgtacttca cggccacgtt ccccctacgtg gtgctgacca ttctgtttgt    1119
ccgcggagtg accctggagg gagcctttga cggcatcatg tactacctaa ccccgcagtg     1179
ggacaagatc ctggaggcca aggtgtgggg tgatgctgcc tcccagatct tctactcact    1239
gggctgcgcg tggggaggcc tcatcaccat ggcttcctac aacaagttcc acaataactg    1299
ttaccgggac agtgtcatca tcagcatcac caactgtgcc accagcgtct atgctggctt    1359
cgtcatcttc tccatcctcg gcttcatggc caatcacctg gcgtggatg tgtcccgtgt    1419 ggcagaccac ggccctggcc tggccttcgt ggcttacccc gaggccctca cactacttcc    1479
catctccccg ctgtggtctc tgctcttctt cttcatgctt atcctgctgg ggctgggcac    1539
tcagttctgc ctcctggaga cgctggtcac agccattgtg gatgaggtgg ggaatgagtg    1599
gatcctgcag aaaaagacct atgtgacctt gggcgtggct gtggctggct tcctgctggg    1659 catcccctc accagccagg caggcatcta ttggctgctg ctgatggaca actatgcggc    1719
cagcttctcc ttggtggtca tctcctgcat catgtgtgtg gccatcatgt acatctacgg    1779
gcaccggaac tacttccagg acatccagat gatgctggga ttcccaccac ccctcttctt    1839
tcagatctgc tggcgcttcg tctctcccgc catcatcttc tttattctag ttttcactgt    1899
gatccagtac cagccgatca cctacaacca ctaccagtac ccaggctggg ccgtggccat    1959
tggcttcctc atggctctgt cctccgtcct ctgcatcccc ctctacgcca tgttccggct    2019
```

| | |
|---|---|
| ctgccgcaca gacggggaca ccctcctcca gcgtttgaaa aatgccacaa agccaagcag | 2079 |
| agactggggc cctgccctcc tggagcaccg gacaggcgc tacgccccca ccatagcccc | 2139 |
| ctctcctgag gacggcttcg aggtccagcc actgcacccg gacaaggcgc agatccccat | 2199 |
| tgtgggcagt aatggctcca gccgcctcca ggactcccgg atatgagcac agctgccagg | 2259 |
| ggagtggccc cacccccacc ccgtgctcca cgagagactg | 2299 |

```
<210> SEQ ID NO 15
<211> LENGTH: 2129
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..612
<220> FEATURE:
<221> NAME/KEY: 3'UTR
<222> LOCATION: 613..2088

<400> SEQUENCE: 15
```

| | |
|---|---|
| cccacacacc ccactccagc tccggagcac ccgtgctggg ctgcatgggg actggccgga | 60 |
| ggggcagggc caggggagcg ggtaggcaga gcttcgggag gagatgaggt gaaagtaatt | 120 |
| gacgctgccc agcccggcag tgggagaggc agggatgcg tcagtgtcgc gctggagctg | 180 |
| gcagaggtgt gaatgagcgg cggagacacg cgggctgcga tcgctcgccc cagg atg | 237 |
| | Met |
| | 1 |

| | | |
|---|---|---|
| gcc gcg gct cat gga cct gtg gcc ccc tct tcc cca gaa cag aat ggt | | 285 |
| Ala Ala Ala His Gly Pro Val Ala Pro Ser Ser Pro Glu Gln Asn Gly | | |
| 5 10 15 | | |
| gct gtg ccc agc gag gcc acc aag agg gac cag aac ctc aaa cgg ggc | | 333 |
| Ala Val Pro Ser Glu Ala Thr Lys Arg Asp Gln Asn Leu Lys Arg Gly | | |
| 20 25 30 | | |
| aac tgg ggc aac cag atc gag cgc ctt cat gtt ccc cta ctt cat cat | | 381 |
| Asn Trp Gly Asn Gln Ile Glu Arg Leu His Val Pro Leu Leu His His | | |
| 35 40 45 | | |
| gct cat ctt ctg cgg gat ccc cct ctt ctt cat gga gct ctc ctt cgg | | 429 |
| Ala His Leu Leu Arg Asp Pro Pro Leu Leu His Gly Ala Leu Leu Arg | | |
| 50 55 60 65 | | |
| cca gtt tgc aag cca ggg gtg cct ggg ggt ctg gag gat cag ccc cat | | 477 |
| Pro Val Cys Lys Pro Gly Val Pro Gly Gly Leu Glu Asp Gln Pro His | | |
| 70 75 80 | | |
| gtt caa agg agt ggg cta tgg tat gat ggt ggt gtc cac cta cat cgg | | 525 |
| Val Gln Arg Ser Gly Leu Trp Tyr Asp Gly Gly Val His Leu His Arg | | |
| 85 90 95 | | |
| cat cta cta caa tgt ggt cat ctg cat cgc ctt cta cta ctt ctt ctc | | 573 |
| His Leu Leu Gln Cys Gly His Leu His Arg Leu Leu Leu Leu Leu Leu | | |
| 100 105 110 | | |
| gtc cat gac gca cgt gct gcc ctg ggc cta ctg caa taa cccctggaac | | 622 |
| Val His Asp Ala Arg Ala Ala Leu Gly Leu Leu Gln * | | |
| 115 120 125 | | |

| | |
|---|---|
| acgcatgact gcgccggtgt actggacgcc tccaacctca ccaatggctc tcggccagcc | 682 |
| gccttgccca gcaacctctc ccacctgctc aaccacagcc tccagaggac cagcccccagc | 742 |
| gaggagtact ggaggctgta cgtgctgaag ctgtcagatg acattgggaa ctttggggag | 802 |
| gtgcggctgc ccctccttgg ctgcctcggt gtcctctggt tggtcgtctt cctctgcctc | 862 |
| atccgagggg tcaagtcttc agggaaagtg gtgtacttca cggccacgtt ccccctacgtg | 922 |

-continued

```
gtgctgacca ttctgtttgt ccgcggagtg accctggagg gagcctttga cggcatcatg      982
tactacctaa ccccgcagtg ggacaagatc ctggaggcca aggtgtgggg tgatgctgcc     1042
tcccagatct tctactcact gggctgcgcg tggggaggcc tcatcaccat ggcttcctac     1102
aacaagttcc acaataactg ttaccgggac agtgtcatca tcagcatcac caactgtgcc     1162
accagcgtct atgctggctt cgtcatcttc tccatcctcg gcttcatggc caatcacctg     1222
ggcgtggatg tgtcccgtgt ggcagaccac ggccctggcc tggccttcgt ggcttacccc     1282
gaggccctca cactacttcc catctccccg ctgtggtctc tgctcttctt cttcatgctt     1342
atcctgctgg ggctgggcac tcagttctgc ctcctggaga cgctggtcac agccattgtg     1402
gatgaggtgg ggaatgagtg gatcctgcag aaaaagacct atgtgacctt gggcgtggct     1462
gtggctggct tcctgctggg catcccccctc accagccagg caggcatcta ttggctgctg     1522
ctgatggaca ctatgcggc cagcttctcc ttggtggtca tctcctgcat catgtgtgtg     1582
gccatcatgt acatctacgg gcaccggaac tacttccagg acatccagat gatgctggga     1642
ttcccaccac ccctcttctt tcagatctgc tggcgcttcg tctctcccgc catcatcttc     1702
tttattctag ttttcactgt gatccagtac cagccgatca cctacaacca ctaccagtac     1762
ccaggctggg ccgtggccat tggcttcctc atggctctgt cctccgtcct ctgcatcccc     1822
ctctacgcca tgttccggct ctgccgcaca gacggggaca ccctcctcca gcgtttgaaa     1882
aatgccacaa agccaagcag agactggggc cctgccctcc tggagcaccg gacagggcgc     1942
tacgccccca ccatagcccc ctctcctgag gacggcttcg aggtccagcc actgcacccg     2002
gacaaggcgc agatccccat tgtgggcagt aatggctcca gccgcctcca ggactcccgg     2062
atatgagcac agctgccagg ggagtggccc cacccccacc ccgtgctcca cgagagactg     2122
tggggct                                                             2129
```

```
<210> SEQ ID NO 16
<211> LENGTH: 2014
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..429
<220> FEATURE:
<221> NAME/KEY: 3'UTR
<222> LOCATION: 430..2014

<400> SEQUENCE: 16
cccacacacc ccactccagc tccggagcac ccgtgctggg ctgcatgggg actggccgga      60
ggggcagggc caggggagcg ggtaggcaga gcttcgggag gagatgaggt gaaagtaatt    120
gacgctgccc agcccggcag tgggagaggc agggatgcg tcagtgtcgc gctgagctg     180 gcagaggtgt gaatgagcgg cggagacacg cgggctgcga tcgctcgccc cagg atg      237
                                                             Met
                                                              1 gcc gcg gct cat gga cct gtg gcc ccc tct tcc cca gaa cag gcg cct      285
Ala Ala Ala His Gly Pro Val Ala Pro Ser Ser Pro Glu Gln Ala Pro
          5                  10                 15 tca tgt tcc cct act tca tca tgc tca tct tct gcg gga tcc ccc tct      333
Ser Cys Ser Pro Thr Ser Ser Cys Ser Ser Ser Ala Gly Ser Pro Ser
     20                  25                  30 tct tca tgg agc tct cct tcg gcc agt ttg caa gcc agg ggt gcc tgg      381
Ser Ser Trp Ser Ser Pro Ser Ala Ser Leu Gln Ala Arg Gly Ala Trp
```

|  |  |  |  |  |  |  |  |  |  |  |  |  |
|---|---|---|---|---|---|---|---|---|---|---|---|---|
|  | 35 |  |  |  | 40 |  |  |  | 45 |  |  |  |

| ggg | tct | gga | gga | tca | gcc | cca | tgt | tca | aag | gag | tgg | gct | atg | gta | tga | 429 |
|---|---|---|---|---|---|---|---|---|---|---|---|---|---|---|---|---|
| Gly | Ser | Gly | Gly | Ser | Ala | Pro | Cys | Ser | Lys | Glu | Trp | Ala | Met | Val | * |  |
| 50 |  |  |  | 55 |  |  |  | 60 |  |  |  | 65 |  |  |  |  |

```
tggtggtgtc cacctacatc ggcatctact acaatgtggt catctgcatc gccttctact    489
acttcttctc gtccatgacg cacgtgctgc cctgggccta ctgcaataac ccctggaaca    549
cgcatgactg cgccggtgta ctggacgcct ccaacctcac caatggctct cggccagccg    609
ccttgcccag caacctctcc cacctgctca accacagcct ccagaggacc agccccagcg    669
aggagtactg gaggctgtac gtgctgaagc tgtcagatga cattgggaac tttggggagg    729
tgcggctgcc cctccttggc tgcctcggtg tctcctggtt ggtcgtcttc ctctgcctca    789
tccgaggggt caagtcttca gggaaagtgg tgtacttcac ggccacgttc ccctacgtgg    849
tgctgaccat tctgtttgtc cgcggagtga ccctggaggg agcctttgac ggcatcatgt    909
actacctaac cccgcagtgg gacaagatcc tggaggccaa ggtgtggggt gatgctgcct    969
cccagatctt ctactcactg ggctgcgcgt ggggaggcct catcaccatg cttcctaca    1029
acaagttcca caataactgt taccgggaca gtgtcatcat cagcatcacc aactgtgcca    1089
ccagcgtcta tgctggcttc gtcatcttct ccatcctcgg cttcatggcc aatcacctgg    1149
gcgtggatgt gtcccgtgtg gcagaccacg gccctggcct ggccttcgtg gcttaccccg    1209
aggccctcac actacttccc atctccccgc tgtggtctct gctcttcttc ttcatgctta    1269
tcctgctggg gctgggcact cagttctgcc tcctggagac gctggtcaca gccattgtgg    1329
atgaggtggg gaatgagtgg atcctgcaga aaaagaccta tgtgaccttg ggcgtggctg    1389
tggctggctt cctgctgggc atccccctca ccagccaggc aggcatctat ggctgctgc    1449
tgatggacaa ctatgcggcc agcttctcct tggtggtcat ctcctgcatc atgtgtgtgg    1509
ccatcatgta catctacggg caccggaact acttccagga catccagatg atgctgggat    1569
tcccaccacc cctcttcttt cagatctgct ggcgcttcgt ctctcccgcc atcatcttct    1629
ttattctagt tttcactgtg atccagtacc agccgatcac ctacaaccac taccagtacc    1689
caggctgggc cgtggccatt ggcttcctca tggctctgtc ctccgtcctc tgcatccccc    1749
tctacgccat gttccggctc tgccgcacag acgggacac cctcctccag cgtttgaaaa    1809
atgccacaaa gccaagcaga gactgggcc ctgccctcct ggagcaccgg acagggcgct    1869
acgcccccac catagccccc tctcctgagg acggcttcga ggtccagcca ctgcacccgg    1929
acaaggcgca gatccccatt gtgggcagta atggctccag ccgcctccag gactcccgga    1989
tatgagcaca gctgccaggg gagtg                                          2014
```

<210> SEQ ID NO 17
<211> LENGTH: 2278
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..924
<220> FEATURE:
<221> NAME/KEY: 3'UTR
<222> LOCATION: 925..2242

<400> SEQUENCE: 17

```
cccacacacc ccactccagc tccggagcac ccgtgctggg ctgcatgggg actggccgga     60
```

```
                                                      -continued ggggcagggc caggggagcg ggtaggcaga gcttcgggag gagatgaggt gaaagtaatt       120
gacgctgccc agcccggcag tgggagaggc aggggatgcg tcagtgtcgc gctggagctg       180
gcagaggtgt gaatgagcgg cggagacacg cgggctgcga tcgctcgccc cagg atg        237
                                                              Met
                                                              1 gcc gcg gct cat gga cct gtg gcc ccc tct tcc cca gaa cag aat ggt        285
Ala Ala Ala His Gly Pro Val Ala Pro Ser Ser Pro Glu Gln Asn Gly
            5                   10                  15 gct gtg ccc agc gag gcc acc aag agg gac cag aac ctc aaa cgg ggc        333
Ala Val Pro Ser Glu Ala Thr Lys Arg Asp Gln Asn Leu Lys Arg Gly
        20                  25                  30 aac tgg ggc aac cag atc gag ttt gta ctg acg agc gtg ggc tat gcc        381
Asn Trp Gly Asn Gln Ile Glu Phe Val Leu Thr Ser Val Gly Tyr Ala
 35                  40                  45 gtg ggc ctg ggc aat gtc tgg cgc ttc cca tac ctc tgc tat cgc aac        429
Val Gly Leu Gly Asn Val Trp Arg Phe Pro Tyr Leu Cys Tyr Arg Asn
 50                  55                  60                  65 ggg gga ggc gcc ttc atg ttc ccc tac ttc atc atg ctc atc ttc tgc        477
Gly Gly Gly Ala Phe Met Phe Pro Tyr Phe Ile Met Leu Ile Phe Cys
                 70                  75                  80 ggg atc ccc ctc ttc ttc atg gag ctc tcc ttc ggc cag ttt gca agc        525
Gly Ile Pro Leu Phe Phe Met Glu Leu Ser Phe Gly Gln Phe Ala Ser
             85                  90                  95 cag ggg tgc ctg ggg gtc tgg agg atc agc ccc atg ttc aaa gga gtg        573
Gln Gly Cys Leu Gly Val Trp Arg Ile Ser Pro Met Phe Lys Gly Val
        100                 105                 110 ggc tat ggt atg atg gtg gtg tcc acc tac atc ggc atc tac tac aat        621
Gly Tyr Gly Met Met Val Val Ser Thr Tyr Ile Gly Ile Tyr Tyr Asn
115                 120                 125 gtg gtc atc tgc atc gcc ttc tac tac ttc ttc tcg tcc atg acg cac        669
Val Val Ile Cys Ile Ala Phe Tyr Tyr Phe Phe Ser Ser Met Thr His
130                 135                 140                 145 gtg ctg ccc tgg gcc tac tgc aat aac ccc tgg aac acg cat gac tgc        717
Val Leu Pro Trp Ala Tyr Cys Asn Asn Pro Trp Asn Thr His Asp Cys
             150                 155                 160 gcc ggt gta ctg gac gcc tcc aac ctc acc aat ggc tct cgg cca gcc        765
Ala Gly Val Leu Asp Ala Ser Asn Leu Thr Asn Gly Ser Arg Pro Ala
        165                 170                 175 gcc ttg ccc agc aac ctc tcc cac ctg ctc aac cac agc ctc cag agg        813
Ala Leu Pro Ser Asn Leu Ser His Leu Leu Asn His Ser Leu Gln Arg
180                 185                 190 acc agc ccc agc gag gag tac tgg aga atc tcg ctc tgt tgc cca ggc        861
Thr Ser Pro Ser Glu Glu Tyr Trp Arg Ile Ser Leu Cys Cys Pro Gly
    195                 200                 205 tgg agt gca gtg gca cga tct cag ctc act gca acc tct gcc tcc cgg        909
Trp Ser Ala Val Ala Arg Ser Gln Leu Thr Ala Thr Ser Ala Ser Arg
210                 215                 220                 225 ggc tgt acg tgc tga agctgtcaga tgacattggg aactttgggg aggtgcggct        964
Gly Cys Thr Cys  *
                230 gcccctcctt ggctgcctcg gtgtctcctg gttggtcgtc ttcctctgcc tcatccgagg      1024 ggtcaagtct tcagggaaag tggtgtactt cacggccacg ttcccctacg tggtgctgac      1084 cattctgttt gtccgcggag tgaccctgga gggagccttt gacggcatca tgtactacct      1144 aaccccgcag tgggacaaga tcctggaggc caaggtgtgg ggtgatgctg cctcccagat      1204 cttctactca ctgggctgcg cgtggggagg cctcatcacc atggcttcct acaacaagtt      1264 ccacaataac tgttaccggg acagtgtcat catcagcatc accaactgtg ccaccagcgt      1324
```

-continued

| | |
|---|---|
| ctatgctggc ttcgtcatct tctccatcct cggcttcatg ccaatcacc tgggcgtgga | 1384 |
| tgtgtcccgt gtggcagacc acggccctgg cctggccttc gtggcttacc ccgaggccct | 1444 |
| cacactactt cccatctccc cgctgtggtc tctgctcttc ttcttcatgc ttatcctgct | 1504 |
| ggggctgggc actcagttct gcctcctgga cacgctggtc acagccattg tggatgaggt | 1564 |
| ggggaatgag tggatcctgc agaaaaagac ctatgtgacc ttgggcgtgg ctgtggctgg | 1624 |
| cttcctgctg ggcatccccc tcaccagcca ggcaggcatc tattggctgc tgctgatgga | 1684 |
| caactatgcg ccagcttct ccttggtggt catctcctgc atcatgtgtg tggccatcat | 1744 |
| gtacatctac gggcaccgga actacttcca ggacatccag atgatgctgg gattcccacc | 1804 |
| acccctcttc tttcagatct gctggcgctt cgtctctccc gccatcatct tctttattct | 1864 |
| agttttcact gtgatccagt accagccgat cacctacaac cactaccagt acccaggctg | 1924 |
| ggccgtggcc attggcttcc tcatggctct gtcctccgtc ctctgcatcc ccctctacgc | 1984 |
| catgttccgg ctctgccgca cagacgggga cacctcctc cagcgtttga aaaatgccac | 2044 |
| aaagccaagc agagactggg gccctgccct cctggagcac cggacagggc gctacgcccc | 2104 |
| caccatagcc ccctctcctg aggacggctt cgaggtccag ccactgcacc cggacaaggc | 2164 |
| gcagatcccc attgtgggca gtaatggctc cagccgcctc caggactccc ggatatgagc | 2224 |
| acagctgcca ggggagtggc cccacccca ccccgtgctc cacgagtgac tgtg | 2278 |

<210> SEQ ID NO 18
<211> LENGTH: 2358
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..519
<220> FEATURE:
<221> NAME/KEY: 3'UTR
<222> LOCATION: 520..2322

<400> SEQUENCE: 18

| | |
|---|---|
| cccacacacc ccactccagc tccggagcac ccgtgctggg ctgcatgggg actggccgga | 60 |
| ggggcagggc caggggagcg ggtaggcaga gcttcgggag gagatgaggt gaaagtaatt | 120 |
| gacgctgccc agcccggcag tgggagaggc aggggatgcg tcagtgtcgc gctggagctg | 180 |
| gcagaggtgt gaatgagcgg cggagacacg cgggctgcga tcgctcgccc cagg atg | 237 |
| | Met |
| | 1 |

| | | | | | | | | | | | | | | |
|---|---|---|---|---|---|---|---|---|---|---|---|---|---|---|
| gcc | gcg | gct | cat | gga | cct | gtg | gcc | ccc | tct | tcc | cca | gaa | cag | ggt | cca | 285 |
| Ala | Ala | Ala | His | Gly | Pro | Val | Ala | Pro | Ser | Ser | Pro | Glu | Gln | Gly | Pro |
| | 5 | | | | 10 | | | | | 15 | | | | | |

| | | | | | | | | | | | | | | | |
|---|---|---|---|---|---|---|---|---|---|---|---|---|---|---|---|
| ggg | caa | gtg | ccc | gca | tgg | gct | ggg | agc | cgg | tgt | gtc | ctc | atc | cct | gga | 333 |
| Gly | Gln | Val | Pro | Ala | Trp | Ala | Gly | Ser | Arg | Cys | Val | Leu | Ile | Pro | Gly |
| | | 20 | | | | | 25 | | | | | 30 | | | |

| | | | | | | | | | | | | | | | |
|---|---|---|---|---|---|---|---|---|---|---|---|---|---|---|---|
| cgc | cgg | gga | cgg | gtg | gag | atg | tca | gcg | gat | ggc | agc | gag | ggt | gag | gag | 381 |
| Arg | Arg | Gly | Arg | Val | Glu | Met | Ser | Ala | Asp | Gly | Ser | Glu | Gly | Glu | Glu |
| 35 | | | | | 40 | | | | | 45 | | | | | |

| | | | | | | | | | | | | | | | |
|---|---|---|---|---|---|---|---|---|---|---|---|---|---|---|---|
| act | cga | aag | cta | cac | ttc | tcc | cct | gta | gga | cat | cct | gac | ttg | acc | ttc | 429 |
| Thr | Arg | Lys | Leu | His | Phe | Ser | Pro | Val | Gly | His | Pro | Asp | Leu | Thr | Phe |
| 50 | | | | | 55 | | | | | 60 | | | | | 65 |

| | | | | | | | | | | | | | | |
|---|---|---|---|---|---|---|---|---|---|---|---|---|---|---|
| aaa | aga | atg | gtg | ctg | tgc | cca | gcg | agg | cca | cca | aga | ggg | acc | aga | acc | 477 |
| Lys | Arg | Met | Val | Leu | Cys | Pro | Ala | Arg | Pro | Pro | Arg | Gly | Thr | Arg | Thr |
| | | | 70 | | | | | 75 | | | | | 80 | | |

```
tca aac ggg gca act ggg gca acc aga tcg agt ttg tac tga        519
Ser Asn Gly Ala Thr Gly Ala Thr Arg Ser Ser Leu Tyr *
         85                  90                  95 cgagcgtggg ctatgccgtg ggcctgggca atgtctggcg cttcccatac ctctgctatc   579
gcaacgggg aggcgccttc atgttcccct acttcatcat gctcatcttc tgcgggatcc   639
ccctcttctt catggagctc tccttcggcc agtttgcaag ccaggggtgc ctggggggtct   699
ggaggatcag ccccatgttc aaaggagtgg gctatggtat gatggtggtg tccacctaca   759
tcggcatcta ctacaatgtg gtcatctgca tcgccttcta ctacttcttc tcgtccatga   819
cgcacgtgct gccctgggcc tactgcaata accctggaa cacgcatgac tgcgccggtg   879
tactggacgc ctccaacctc accaatggct ctcggccagc cgccttgccc agcaaacctct   939
cccacctgct caaccacagc ctccagagga ccagcccag cgaggagtac tggaggctgt   999
acgtgctgaa gctgtcagat gacattggga actttgggga ggtgcggctg ccctccttg   1059
gctgcctcgg tgtctcctgg ttggtcgtct tcctctgcct catccgaggg gtcaagtctt   1119
cagggaaagt ggtgtacttc acggccacgt tccctacgt ggtgctgacc attctgtttg   1179
tccgcggagt gaccctggag ggagcctttg acggcatcat gtactaccta accccgcagt   1239
gggacaagat cctggaggcc aaggtgtggg gtgatgctgc ctcccagatc ttctactcac   1299
tgggctgcgc gtggggaggc ctcatcacca tggcttccta acaagttc cacaataact   1359
gttaccggga cagtgtcatc atcagcatca ccaactgtgc caccagcgtc tatgctggct   1419
tcgtcatctt ctccatcctc ggcttcatgg ccaatcacct gggcgtggat gtgtcccgtg   1479
tggcagacca cggccctggc ctggccttcg tggcttaccc cgaggccctc acactacttc   1539
ccatctcccc gctgtggtct ctgctcttct tcttcatgct tatcctgctg gggctgggca   1599
ctcagttctg cctcctggag acgctggtca cagccattgt ggatgaggtg gggaatgagt   1659
ggatcctgca gaaaaagacc tatgtgacct tgggcgtggc tgtggctggc ttcctgctgg   1719
gcatcccct caccagccag gcatctattg gctgctgctg atggacaact atgcggccag   1779
cttctccttg gtggtcatct cctgcatcat gtgtgtggcc atcatgtaca tctacgggca   1839
ccggaactac ttccaggaca tccagatgat gctgggattc ccaccacccc tcttctttca   1899
gatctgctgg cgcttcgtct ctcccgccat catcttcttt attctagttt tcactgtgat   1959
ccagtaccag ccgatcacct acaaccacta ccagtaccca ggctgggccg tggccattgg   2019
cttcctcatg gctctgtcct ccgtcctctg catccccctc tacgccatgt tccggctctg   2079
ccgcacagac ggggacaccc tcctccagcg ttttgaaaaat gccacaaagc caagcagaga   2139
ctggggccct gccctcctgg agcaccggac agggcgctac gccccacca tagccccctc   2199
tcctgaggac ggcttcgagg tccagccact gcacccggac aaggcgcaga tccccattgt   2259
gggcagtaat ggctccagcc gcctccagga ctcccggata tgagcacagc tgccagggga   2319
gtggccccac cccacccccg tgctccacga tagactgtg                          2358

<210> SEQ ID NO 19
<211> LENGTH: 2200
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..1605
<220> FEATURE:
```

<221> NAME/KEY: 3'UTR
<222> LOCATION: 1606..2167

<400> SEQUENCE: 19

| | | |
|---|---|---|
| cccacacacc ccactccagc tccggagcac ccgtgctggg ctgcatgggg actggccgga | 60 | |
| ggggcagggc caggggagcg ggtaggcaga gcttcgggag gagatgaggt gaaagtaatt | 120 | |
| gacgctgccc agcccggcag tgggagaggc aggggatgcg tcagtgtcgc gctgagctg | 180 | |
| gcagaggtgt gaatgagcgg cggagacacg cgggctgcga tcgctcgccc cagg atg<br>                                                                                                                   Met | 237 | |
| | | 1 |
| gcc gcg gct cat gga cct gtg gcc ccc tct tcc cca gaa cag aat ggt<br>Ala Ala Ala His Gly Pro Val Ala Pro Ser Ser Pro Glu Gln Asn Gly | 285 | |
|              5                       10                       15 | | |
| gct gtg ccc agc gag gcc acc aag agg gac cag aac ctc aaa cgg ggc<br>Ala Val Pro Ser Glu Ala Thr Lys Arg Asp Gln Asn Leu Lys Arg Gly | 333 | |
|           20                    25                      30 | | |
| aac tgg ggc aac cag atc gag ttt gta ctg acg agc gtg ggc tat gcc<br>Asn Trp Gly Asn Gln Ile Glu Phe Val Leu Thr Ser Val Gly Tyr Ala | 381 | |
|  35                    40                       45 | | |
| gtg ggc ctg ggc aat gtc tgg cgc ttc cca tac ctc tgc tat cgc aac<br>Val Gly Leu Gly Asn Val Trp Arg Phe Pro Tyr Leu Cys Tyr Arg Asn | 429 | |
| 50                  55                       60                       65 | | |
| ggg gga ggc gcc ttc atg ttc ccc tac ttc atc atg ctc atc ttc tgc<br>Gly Gly Gly Ala Phe Met Phe Pro Tyr Phe Ile Met Leu Ile Phe Cys | 477 | |
|                     70                       75                       80 | | |
| ggg atc ccc ctc ttc ttc atg gag ctc tcc ttc ggc cag ttt gca agc<br>Gly Ile Pro Leu Phe Phe Met Glu Leu Ser Phe Gly Gln Phe Ala Ser | 525 | |
|           85                    90                       95 | | |
| cag ggg tgc ctg ggg gtc tgg agg atc agc ccc atg ttc aaa gga gtg<br>Gln Gly Cys Leu Gly Val Trp Arg Ile Ser Pro Met Phe Lys Gly Val | 573 | |
|              100                 105                 110 | | |
| ggc tat ggt atg atg gtg gtg tcc acc tac atc ggc atc tac tac aat<br>Gly Tyr Gly Met Met Val Val Ser Thr Tyr Ile Gly Ile Tyr Tyr Asn | 621 | |
|     115                 120                 125 | | |
| gtg gtc atc tgc atc gcc ttc tac tac ttc ttc tcg tcc atg acg cac<br>Val Val Ile Cys Ile Ala Phe Tyr Tyr Phe Phe Ser Ser Met Thr His | 669 | |
| 130                  135                 140                145 | | |
| gtg ctg ccc tgg gcc tac tgc aat aac ccc tgg aac acg cat gac tgc<br>Val Leu Pro Trp Ala Tyr Cys Asn Asn Pro Trp Asn Thr His Asp Cys | 717 | |
|                 150                 155                 160 | | |
| gcc ggt gta ctg gac gcc tcc aac ctc acc aat ggc tct cgg cca gcc<br>Ala Gly Val Leu Asp Ala Ser Asn Leu Thr Asn Gly Ser Arg Pro Ala | 765 | |
|              165                 170                 175 | | |
| gcc ttg ccc agc aac ctc tcc cac ctg ctc aac cac agc ctc cag agg<br>Ala Leu Pro Ser Asn Leu Ser His Leu Leu Asn His Ser Leu Gln Arg | 813 | |
|         180                  185                 190 | | |
| acc agc ccc agc gag gag tac tgg agg ctg tac gtg ctg aag ctg tca<br>Thr Ser Pro Ser Glu Glu Tyr Trp Arg Leu Tyr Val Leu Lys Leu Ser | 861 | |
|     195                 200                 205 | | |
| gat gac att ggg aac ttt ggg gag gtg cgg ctg ccc ctc ctt ggc tgc<br>Asp Asp Ile Gly Asn Phe Gly Glu Val Arg Leu Pro Leu Leu Gly Cys | 909 | |
| 210                  215                 220                225 | | |
| ctc ggt gtc tcc tgg ttg gtc gtc ttc ctc tgc ctc atc cga ggg gtc<br>Leu Gly Val Ser Trp Leu Val Val Phe Leu Cys Leu Ile Arg Gly Val | 957 | |
|                     230                 235                 240 | | |
| aag tct tca ggg aaa gtg gtg tac ttc acg gcc acg ttc ccc tac gtg<br>Lys Ser Ser Gly Lys Val Val Tyr Phe Thr Ala Thr Phe Pro Tyr Val | 1005 | |
|              245                 250                 255 | | |

```
gtg ctg acc att ctg ttt gtc cgc gga gtg acc ctg gag gga gcc ttt    1053
Val Leu Thr Ile Leu Phe Val Arg Gly Val Thr Leu Glu Gly Ala Phe
        260                 265                 270 gac ggc atc atg tac tac cta acc ccg cag tgg gac aag atc ctg gag    1101
Asp Gly Ile Met Tyr Tyr Leu Thr Pro Gln Trp Asp Lys Ile Leu Glu
275                 280                 285 gcc aag gtg tgg ggt gat gct gcc tcc cag atc ttc tac tca ctg ggc    1149
Ala Lys Val Trp Gly Asp Ala Ala Ser Gln Ile Phe Tyr Ser Leu Gly
290                 295                 300                 305 tgc gcg tgg gga ggc ctc atc acc atg gct tcc tac aac aag ttc cac    1197
Cys Ala Trp Gly Gly Leu Ile Thr Met Ala Ser Tyr Asn Lys Phe His
                310                 315                 320 aat aac tgt tac cgg gac agt gtc atc atc agc atc acc aac tgt gcc    1245
Asn Asn Cys Tyr Arg Asp Ser Val Ile Ile Ser Ile Thr Asn Cys Ala
            325                 330                 335 acc agc gtc tat gct ggc ttc gtc atc ttc tcc atc ctc ggc ttc atg    1293
Thr Ser Val Tyr Ala Gly Phe Val Ile Phe Ser Ile Leu Gly Phe Met
        340                 345                 350 gcc aat cac ctg ggc gtg gat gtg tcc cgt gtg gca gac cac ggc cct    1341
Ala Asn His Leu Gly Val Asp Val Ser Arg Val Ala Asp His Gly Pro
355                 360                 365 ggc ctg gcc ttc gtg gct tac ccc gag gcc ctc aca cta ctt ccc atc    1389
Gly Leu Ala Phe Val Ala Tyr Pro Glu Ala Leu Thr Leu Leu Pro Ile
370                 375                 380                 385 tcc ccg ctg tgg tct ctg ctc ttc ttc ttc atg ctt atc ctg ctg ggg    1437
Ser Pro Leu Trp Ser Leu Leu Phe Phe Phe Met Leu Ile Leu Leu Gly
                390                 395                 400 ctg ggc act cag ttc tgc ctc ctg gag acg ctg gtc aca gcc att gtg    1485
Leu Gly Thr Gln Phe Cys Leu Leu Glu Thr Leu Val Thr Ala Ile Val
            405                 410                 415 gat gag gtg ggg aat gag tgg atc ctg cag aaa aag acc tat gtg acc    1533
Asp Glu Val Gly Asn Glu Trp Ile Leu Gln Lys Lys Thr Tyr Val Thr
        420                 425                 430 ttg ggc gtg gct gtg gct ggc ttc ctg ctg ggc atc ccc ctc acc agc    1581
Leu Gly Val Ala Val Ala Gly Phe Leu Leu Gly Ile Pro Leu Thr Ser
435                 440                 445 cag gca tct att ggc tgc tgc tga tggacaacta tgcggccagc ttctccttgg   1635
Gln Ala Ser Ile Gly Cys Cys   *
450                 455 tggtcatctc ctgcatcatg tgtgtggcca tcatgtacat ctacgggcac cggaactact   1695
tccaggacat ccagatgatg ctgggattcc caccacccct cttctttcag atctgctggc   1755
gcttcgtctc tcccgccatc atcttcttta ttctagtttt cactgtgatc cagtaccagc   1815
cgatcaccta caaccactac cagtacccag ctgggccgt ggccattggc ttcctcatgg    1875
ctctgtcctc cgtcctctgc atcccccctct acgccatgtt ccggctctgc cgcacagacg   1935
gggacaccct cctccagcgt ttgaaaaatg ccacaaagcc aagcagagac tggggccctg   1995
ccctcctgga gcaccggaca gggcgctacg ccccccaccat agccccctct cctgaggacg   2055
gcttcgaggt ccagccactg cacccggaca aggcgcagat cccattgtg ggcagtaatg    2115 gctccagccg cctccaggac tcccggatat gagcacagct gccaggggag tggccccacc   2175 cccacccccgt gctccacgag agact                                        2200

<210> SEQ ID NO 20
<211> LENGTH: 2406
<212> TYPE: DNA
<213> ORGANISM: Homo sapiens
<220> FEATURE:
<221> NAME/KEY: 5'UTR
```

```
<222> LOCATION: 1..234
<220> FEATURE:
<221> NAME/KEY: CDS
<222> LOCATION: 235..1887
<220> FEATURE:
<221> NAME/KEY: 3'UTR
<222> LOCATION: 1888..2371

<400> SEQUENCE: 20
cccacacacc ccactccagc tccggagcac ccgtgctggg ctgcatgggg actggccgga      60
ggggcagggc caggggagcg ggtaggcaga gcttcgggag gagatgaggt gaaagtaatt     120
gacgctgccc agcccggcag tgggagaggc aggggatgcg tcagtgtcgc gctggagctg     180
gcagaggtgt gaatgagcgg cggagacacg cgggctgcga tcgctcgccc cagg atg      237
                                                                Met
                                                                 1 gcc gcg gct cat gga cct gtg gcc ccc tct tcc cca gaa cag aat ggt       285
Ala Ala Ala His Gly Pro Val Ala Pro Ser Ser Pro Glu Gln Asn Gly
        5                   10                  15 gct gtg ccc agc gag gcc acc aag agg gac cag aac ctc aaa cgg ggc       333
Ala Val Pro Ser Glu Ala Thr Lys Arg Asp Gln Asn Leu Lys Arg Gly
     20                  25                  30 aac tgg ggc aac cag atc gag ttt gta ctg acg agc gtg ggc tat gcc       381
Asn Trp Gly Asn Gln Ile Glu Phe Val Leu Thr Ser Val Gly Tyr Ala
 35                  40                  45 gtg ggc ctg ggc aat gtc tgg cgc ttc cca tac ctc tgc tat cgc aac       429
Val Gly Leu Gly Asn Val Trp Arg Phe Pro Tyr Leu Cys Tyr Arg Asn
 50                  55                  60                  65 ggg gga ggc gcc ttc atg ttc ccc tac ttc atc atg ctc atc ttc tgc       477
Gly Gly Gly Ala Phe Met Phe Pro Tyr Phe Ile Met Leu Ile Phe Cys
                 70                  75                  80 ggg atc ccc ctc ttc ttc atg gag ctc tcc ttc ggc cag ttt gca agc       525
Gly Ile Pro Leu Phe Phe Met Glu Leu Ser Phe Gly Gln Phe Ala Ser
             85                  90                  95 cag ggg tgc ctg ggg gtc tgg agg atc agc ccc atg ttc aaa gga gtg       573
Gln Gly Cys Leu Gly Val Trp Arg Ile Ser Pro Met Phe Lys Gly Val
        100                 105                 110 ggc tat ggt atg atg gtg gtg tcc acc tac atc ggc atc tac tac aat       621
Gly Tyr Gly Met Met Val Val Ser Thr Tyr Ile Gly Ile Tyr Tyr Asn
    115                 120                 125 gtc gtc atc tgc atc gcc ttc tac tac ttc ttc tcg tcc atg acg cac       669
Val Val Ile Cys Ile Ala Phe Tyr Tyr Phe Phe Ser Ser Met Thr His
130                 135                 140                 145 gtg ctg ccc tgg gcc tac tgc aat aac ccc tgg aac acg cat gac tgc       717
Val Leu Pro Trp Ala Tyr Cys Asn Asn Pro Trp Asn Thr His Asp Cys
                150                 155                 160 gcc ggt gta ctg gac gcc tcc aac ctc acc aat ggc tct cgg cca gcc       765
Ala Gly Val Leu Asp Ala Ser Asn Leu Thr Asn Gly Ser Arg Pro Ala
            165                 170                 175 gcc ttg ccc agc aac ctc tcc cac ctg ctc aac cac agc ctc cag agg       813
Ala Leu Pro Ser Asn Leu Ser His Leu Leu Asn His Ser Leu Gln Arg
        180                 185                 190 acc agc ccc agc gag gag tac tgg agg ctg tac gtg ctg aag ctg tca       861
Thr Ser Pro Ser Glu Glu Tyr Trp Arg Leu Tyr Val Leu Lys Leu Ser
    195                 200                 205 gat gac att ggg aac ttt ggg gag gtg cgg ctg ccc ctc ctt ggc tgc       909
Asp Asp Ile Gly Asn Phe Gly Glu Val Arg Leu Pro Leu Leu Gly Cys
210                 215                 220                 225 ctc ggt gtc tcc tgg ttg gtc gtc ttc ctc tgc ctc atc cga ggg gtc       957
Leu Gly Val Ser Trp Leu Val Val Phe Leu Cys Leu Ile Arg Gly Val
                230                 235                 240
```

```
aag tct tca ggg aaa gtg gtg tac ttc acg gcc acg ttc ccc tac gtg    1005
Lys Ser Ser Gly Lys Val Val Tyr Phe Thr Ala Thr Phe Pro Tyr Val
            245                 250                 255 gtg ctg acc att ctg ttt gtc cgc gga gtg acc ctg gag gga gcc ttt    1053
Val Leu Thr Ile Leu Phe Val Arg Gly Val Thr Leu Glu Gly Ala Phe
            260                 265                 270 gac ggc atc atg tac tac cta acc ccg cag tgg gac aag atc ctg gag    1101
Asp Gly Ile Met Tyr Tyr Leu Thr Pro Gln Trp Asp Lys Ile Leu Glu
            275                 280                 285 gcc aag gtg tgg ggt gat gct gcc tcc cag atc ttc tac tca ctg ggc    1149
Ala Lys Val Trp Gly Asp Ala Ala Ser Gln Ile Phe Tyr Ser Leu Gly
290                 295                 300                 305 tgc gcg tgg gga ggc ctc atc acc atg gct tcc tac aac aag ttc cac    1197
Cys Ala Trp Gly Gly Leu Ile Thr Met Ala Ser Tyr Asn Lys Phe His
                310                 315                 320 aat aac tgt tac cgg gac agt gtc atc atc agc atc acc aac tgt gcc    1245
Asn Asn Cys Tyr Arg Asp Ser Val Ile Ile Ser Ile Thr Asn Cys Ala
            325                 330                 335 acc agc gtc tat gct ggc ttc gtc atc ttc tcc atc ctc ggc ttc atg    1293
Thr Ser Val Tyr Ala Gly Phe Val Ile Phe Ser Ile Leu Gly Phe Met
            340                 345                 350 gcc aat cac ctg ggc gtg gat gtg tcc cgt gtg gca gac cac ggc cct    1341
Ala Asn His Leu Gly Val Asp Val Ser Arg Val Ala Asp His Gly Pro
355                 360                 365 ggc ctg gcc ttc gtg gct tac ccc gag gcc ctc aca cta ctt ccc atc    1389
Gly Leu Ala Phe Val Ala Tyr Pro Glu Ala Leu Thr Leu Leu Pro Ile
370                 375                 380                 385 tcc ccg ctg tgg tct ctg ctc ttc ttc atg ctt atc ctg ctg ggg        1437
Ser Pro Leu Trp Ser Leu Leu Phe Phe Met Leu Ile Leu Leu Gly
                390                 395                 400 ctg ggc act cag ttc tgc ctc ctg gag acg ctg gtc aca gcc att gtg    1485
Leu Gly Thr Gln Phe Cys Leu Leu Glu Thr Leu Val Thr Ala Ile Val
            405                 410                 415 gat gag gtg ggg aat gag tgg atc ctg cag aaa aag acc tat gtg acc    1533
Asp Glu Val Gly Asn Glu Trp Ile Leu Gln Lys Lys Thr Tyr Val Thr
                420                 425                 430 ttg ggc gtg gct gtg gct ggc ttc ctg ctg ggc atc ccc ctc acc agc    1581
Leu Gly Val Ala Val Ala Gly Phe Leu Leu Gly Ile Pro Leu Thr Ser
435                 440                 445 cag gca ggc atc tat tgg ctg ctg ctg atg gac aac tat gcg gcc agc    1629
Gln Ala Gly Ile Tyr Trp Leu Leu Leu Met Asp Asn Tyr Ala Ala Ser
450                 455                 460                 465 ttc tcc ttg gtg gtc atc tcc tgc atc atg tgt gtg gcc atc atg tac    1677
Phe Ser Leu Val Val Ile Ser Cys Ile Met Cys Val Ala Ile Met Tyr
                470                 475                 480 atc tac ggg cac cgg aac tac ttc cag gac atc cag atg atg ctg gga    1725
Ile Tyr Gly His Arg Asn Tyr Phe Gln Asp Ile Gln Met Met Leu Gly
            485                 490                 495 ttc cca cca ccc ctc ttc ttt cag atc tgc tgg cgc ttc gtc tct ccc    1773
Phe Pro Pro Pro Leu Phe Phe Gln Ile Cys Trp Arg Phe Val Ser Pro
            500                 505                 510 gcc atc atc ttc agc ctt ccc act cac cgc gct ccg gcc ccc ggc cct    1821
Ala Ile Ile Phe Ser Leu Pro Thr His Arg Ala Pro Ala Pro Gly Pro
515                 520                 525 gcc tgc ttc ttc cac ggc cca gat gtt gac agc tgt ccc tgt tct gcc    1869
Ala Cys Phe Phe His Gly Pro Asp Val Asp Ser Cys Pro Cys Ser Ala
530                 535                 540                 545 cca aat gcc ctt ttc tag tttgggaaac cagagaggaa agggtgctgg           1917
Pro Asn Ala Leu Phe  *
```

-continued

```
                       550
tagagggatg gcctggggtc tgggctctgg gtcggcctca cgcccactcc cacacctgcc    1977
ccgtgcagtt tattctagtt ttcactgtga tccagtacca gccgatcacc tacaaccact    2037
accagtaccc aggctgggcc gtggccattg gcttcctcat ggctctgtcc tccgtcctct    2097
gcatccccct ctacgccatg ttccggctct gccgcacaga cggggacacc ctcctccagc    2157
gtttgaaaaa tgccacaaag ccaagcagag actggggccc tgccctcctg gagcaccgga    2217
cagggcgcta cgcccccacc atagcccccT ctcctgagga cggcttcgag gtccagccac    2277
tgcacccgga caaggcgcag atccccattg tgggcagtaa tggctccagc cgcctccagg    2337
actcccggat atgagcacag ctgccagggg agtggcccca cccccacccc gtgctccacg    2397
agagactgt                                                            2406

<210> SEQ ID NO 21
<211> LENGTH: 2310
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..801
<220> FEATURE:
<221> NAME/KEY: 3'UTR
<222> LOCATION: 802..2277

<400> SEQUENCE: 21
cccacacacc ccactccagc tccggagcac ccgtgctggg ctgcatgggg actggccgga    60
ggggcagggc caggggagcg ggtaggcaga gcttcgggag gagatgaggt gaaagtaatt   120
gacgctgccc agcccggcag tgggagaggc aggggatgcg tcagtgtcgc gctggagctg   180
gcagaggtgt gaatgagcgg cggagacacg cgggctgcga tcgctcgccc cagg atg     237
                                                              Met
                                                              1 gcc gcg gct cat gga cct gtg gcc ccc tct tcc cca gaa cag aac att      285
Ala Ala Ala His Gly Pro Val Ala Pro Ser Ser Pro Glu Gln Asn Ile
        5                  10                  15 ttc cag ggt cca ggg caa gtg ccc gca tgg gct ggg agc cgg tgt gtc      333
Phe Gln Gly Pro Gly Gln Val Pro Ala Trp Ala Gly Ser Arg Cys Val
     20                  25                  30 ctc atc cct gga cgc cgg gga cgg gtg gag atg tca gcg gat gac agc      381
Leu Ile Pro Gly Arg Arg Gly Arg Val Glu Met Ser Ala Asp Asp Ser
 35                  40                  45 gag gaa tgg tgc tgt gcc cag cga ggc cac caa gag gga cca gaa cct      429
Glu Glu Trp Cys Cys Ala Gln Arg Gly His Gln Glu Gly Pro Glu Pro
 50                  55                  60                  65 caa acg ggg caa ctg ggg caa cca gat cga gtt tgt act gac gag cgt      477
Gln Thr Gly Gln Leu Gly Gln Pro Asp Arg Val Cys Thr Asp Glu Arg
             70                  75                  80 ggg cta tgc cgt ggg cct ggg caa tgt ctg gcg ctt ccc ata cct ctg      525
Gly Leu Cys Arg Gly Pro Gly Gln Cys Leu Ala Leu Pro Ile Pro Leu
         85                  90                  95 cta tcg caa cgg ggg agg cgc ctt cat gtt ccc cta ctt cat cat gct      573
Leu Ser Gln Arg Gly Arg Arg Leu His Val Pro Leu Leu His His Ala
        100                 105                 110 cat ctt ctg cgg gat ccc cct ctt ctt cat gga gct ctc ctt cgg cca      621
His Leu Leu Arg Asp Pro Pro Leu Leu His Gly Ala Leu Leu Arg Pro
    115                 120                 125
```

| | | | | | | | | | | | | | | |
|---|---|---|---|---|---|---|---|---|---|---|---|---|---|---|
| gtt | tgc | aag | cca | ggg | gtg | cct | ggg | ggt | ctg | gag | gat | cag | ccc | cat gtt | 669
| Val | Cys | Lys | Pro | Gly | Val | Pro | Gly | Gly | Leu | Glu | Asp | Gln | Pro | His Val |
| 130 | | | | 135 | | | | | 140 | | | | | 145 |

| | | | | | | | | | | | | | | |
|---|---|---|---|---|---|---|---|---|---|---|---|---|---|---|
| caa | agg | agt | ggg | cta | tgg | tat | gat | ggt | ggt | gtc | cac | cta | cat | cgg cat | 717
| Gln | Arg | Ser | Gly | Leu | Trp | Tyr | Asp | Gly | Gly | Val | His | Leu | His | Arg His |
| | | | | 150 | | | | | 155 | | | | | 160 |

| | | | | | | | | | | | | | | |
|---|---|---|---|---|---|---|---|---|---|---|---|---|---|---|
| cta | cta | caa | tgt | ggt | cat | ctg | cat | cgc | ctt | cta | ctt | ctc | gtc | | 765
| Leu | Leu | Gln | Cys | Gly | His | Leu | His | Arg | Leu | Leu | Leu | Leu | Val | |
| | | | 165 | | | | | 170 | | | | | 175 | |

| | | | | | | | | | | |
|---|---|---|---|---|---|---|---|---|---|---|
| cat | gac | gca | cgt | gct | gcc | ctg | ggc | cta | ctg | caa taa cccctggaac | 811
| His | Asp | Ala | Arg | Ala | Ala | Leu | Gly | Leu | Leu | Gln * |
| | | 180 | | | | | 185 | | | |

```
acgcatgact gcgccggtgt actggacgcc tccaacctca ccaatggctc tcggccagcc    871
gccttgccca gcaacctctc ccacctgctc aaccacagcc tccagaggac cagccccagc    931
gaggagtact ggaggctgta cgtgctgaag ctgtcagatg acattgggaa ctttggggag    991
gtgcggctgc ccctccttgg ctgcctcggt gtctcctggt tggtcgtctt cctctgcctc   1051
atccgagggg tcaagtcttc agggaaagtg gtgtacttca cggccacgtt ccctacgtg   1111
gtgctgacca ttctgtttgt ccgcggagtg accctggagg agcctttga cggcatcatg   1171
tactacctaa ccccgcagtg ggacaagatc ctggaggcca aggtgtgggg tgatgctgcc   1231
tcccagatct tctactcact gggctgcgcg tggggaggcc tcatcaccat ggcttcctac   1291
aacaagttcc acaataactg ttaccgggac agtgtcatca tcagcatcac caactgtgcc   1351
accagcgtct atgctggctt cgtcatcttc tccatcctcg gcttcatggc caataccctg   1411
ggcgtggatg tgtcccgtgt ggcagaccac ggccctggcc tggccttcgt ggcttacccc   1471
gaggccctca cactacttcc catctccccg ctgtggtctc tgctcttctt cttcatgctt   1531
atcctgctgg ggctgggcac tcagttctgc ctcctggaga cgctggtcac agccattgtg   1591
gatgaggtgg ggaatgagtg gatcctgcag aaaaagacct atgtgacctt gggcgtggct   1651
gtggctggct tcctgctggg catcccctc accagccagg caggcatcta ttggctgctg   1711
ctgatggaca actatgcggc cagcttctcc ttggtggtca tctcctgcat catgtgtgtg   1771
gccatcatgt acatctacgg gcaccggaac tacttccagg acatccagat gatgctggga   1831
ttcccaccac ccctcttctt tcagatctgc tggcgcttcg tctctcccgc catcatcttc   1891
tttattctag ttttcactgt gatccagtac cagccgatca cctacaacca ctaccagtac   1951
ccaggctggg ccgtgccat tggcttcctc atggctctgt cctccgtcct ctgcatcccc   2011
ctctacgcca tgttccgcct ctgccgcaca gacgggaca ccctcctcca gcgtttgaaa   2071
aatgccacaa agccaagcag agactggggc cctgccctcc tggagcaccg gacagggcgc   2131
tacgccccca ccatagcccc ctctcctgag gacggcttcg aggtccagcc actgcacccg   2191
gacaaggcgc agatccccat tgtgggcagt aatggctcca gccgcctcca ggactcccgg   2251
atatgagcac agctgccagg ggagtggccc caccccacc ccgtgctcca cgagagact   2310
```

<210> SEQ ID NO 22
<211> LENGTH: 633
<212> TYPE: PRT
<213> ORGANISM: Homo sapiens

<400> SEQUENCE: 22

| | | | | | | | | | | | | | | |
|---|---|---|---|---|---|---|---|---|---|---|---|---|---|---|
| Met | Val | Gly | Lys | Gly | Ala | Lys | Gly | Met | Leu | Asn | Gly | Ala | Val | Pro Ser |
| 1 | | | | 5 | | | | | 10 | | | | | 15 |

| | | | | | | | | | | | | | | |
|---|---|---|---|---|---|---|---|---|---|---|---|---|---|---|
| Glu | Ala | Thr | Lys | Arg | Asp | Gln | Asn | Leu | Lys | Arg | Gly | Asn | Trp | Gly Asn |
| | | | 20 | | | | | 25 | | | | | 30 | |

```
Gln Ile Glu Phe Val Leu Thr Ser Val Gly Tyr Ala Val Gly Leu Gly
            35                  40                  45

Asn Val Trp Arg Phe Pro Tyr Leu Cys Tyr Arg Asn Gly Gly Gly Ala
         50                  55                  60

Phe Met Phe Pro Tyr Phe Ile Met Leu Ile Phe Cys Gly Ile Pro Leu
 65                  70                  75                  80

Phe Phe Met Glu Leu Ser Phe Gly Gln Phe Ala Ser Gln Gly Cys Leu
                 85                  90                  95

Gly Val Trp Arg Ile Ser Pro Met Phe Lys Gly Val Gly Tyr Gly Met
                100                 105                 110

Met Val Val Ser Thr Tyr Ile Gly Ile Tyr Tyr Asn Val Val Ile Cys
                115                 120                 125

Ile Ala Phe Tyr Tyr Phe Phe Ser Ser Met Thr His Val Leu Pro Trp
            130                 135                 140

Ala Tyr Cys Asn Asn Pro Trp Asn Thr His Asp Cys Ala Gly Val Leu
145                 150                 155                 160

Asp Ala Ser Asn Leu Thr Asn Gly Ser Arg Pro Ala Ala Leu Pro Ser
                165                 170                 175

Asn Leu Ser His Leu Leu Asn His Ser Leu Gln Arg Thr Ser Pro Ser
                180                 185                 190

Glu Glu Tyr Trp Arg Leu Tyr Val Leu Lys Leu Ser Asp Asp Ile Gly
            195                 200                 205

Asn Phe Gly Glu Val Arg Leu Pro Leu Leu Gly Cys Leu Gly Val Ser
            210                 215                 220

Trp Leu Val Val Phe Leu Cys Leu Ile Arg Gly Val Lys Ser Ser Gly
225                 230                 235                 240

Lys Val Val Tyr Phe Thr Ala Thr Phe Pro Tyr Val Val Leu Thr Ile
                245                 250                 255

Leu Phe Val Arg Gly Val Thr Leu Glu Gly Ala Phe Asp Gly Ile Met
            260                 265                 270

Tyr Tyr Leu Thr Pro Gln Trp Asp Lys Ile Leu Glu Ala Lys Val Trp
            275                 280                 285

Gly Asp Ala Ala Ser Gln Ile Phe Tyr Ser Leu Ala Cys Ala Trp Gly
            290                 295                 300

Gly Leu Ile Thr Met Ala Ser Tyr Asn Lys Phe His Asn Asn Cys Tyr
305                 310                 315                 320

Arg Asp Ser Val Ile Ile Ser Ile Thr Asn Cys Ala Thr Ser Val Tyr
                325                 330                 335

Ala Gly Phe Val Ile Phe Ser Ile Leu Gly Phe Met Ala Asn His Leu
            340                 345                 350

Gly Val Asp Val Ser Arg Val Ala Asp His Gly Pro Gly Leu Ala Phe
            355                 360                 365

Val Ala Tyr Pro Glu Ala Leu Thr Leu Leu Pro Ile Ser Pro Leu Trp
            370                 375                 380

Ser Leu Leu Phe Phe Phe Met Leu Ile Leu Leu Gly Leu Gly Thr Gln
385                 390                 395                 400

Phe Cys Leu Leu Glu Thr Leu Val Thr Ala Ile Val Asp Glu Val Gly
                405                 410                 415

Asn Glu Trp Ile Leu Gln Lys Lys Thr Tyr Val Thr Leu Gly Val Ala
            420                 425                 430

Val Ala Gly Phe Leu Leu Gly Ile Pro Leu Thr Ser Gln Ala Gly Ile
            435                 440                 445
```

```
Tyr Trp Leu Leu Leu Met Asp Asn Tyr Ala Ala Ser Phe Ser Leu Val
        450                 455                 460

Val Ile Ser Cys Ile Met Cys Val Ala Ile Met Tyr Ile Tyr Gly His
465                 470                 475                 480

Arg Asn Tyr Phe Gln Asp Ile Gln Met Met Leu Gly Phe Pro Pro Pro
                485                 490                 495

Leu Phe Phe Gln Ile Cys Trp Arg Phe Val Ser Pro Ala Ile Ile Phe
                500                 505                 510

Phe Ile Leu Val Phe Thr Val Ile Gln Tyr Gln Pro Ile Thr Tyr Asn
            515                 520                 525

His Tyr Gln Tyr Pro Gly Trp Ala Val Ala Ile Gly Phe Leu Met Ala
        530                 535                 540

Leu Ser Ser Val Leu Cys Ile Pro Leu Tyr Ala Met Phe Arg Leu Cys
545                 550                 555                 560

Arg Thr Asp Gly Asp Thr Leu Leu Gln Arg Leu Lys Asn Ala Thr Lys
                565                 570                 575

Pro Ser Arg Asp Trp Gly Pro Ala Leu Leu Glu His Arg Thr Gly Arg
                580                 585                 590

Tyr Ala Pro Thr Ile Ala Pro Ser Pro Glu Asp Gly Phe Glu Val Gln
            595                 600                 605

Ser Leu His Pro Asp Lys Ala Gln Ile Pro Ile Val Gly Ser Asn Gly
        610                 615                 620

Ser Ser Arg Leu Gln Asp Ser Arg Ile
625                 630

<210> SEQ ID NO 23
<211> LENGTH: 687
<212> TYPE: PRT
<213> ORGANISM: Homo sapiens

<400> SEQUENCE: 23

Met Val Gly Lys Gly Ala Lys Gly Met Leu Val Thr Leu Leu Pro Val
1               5                   10                  15

Gln Arg Ser Phe Phe Leu Pro Pro Phe Ser Gly Ala Thr Pro Ser Thr
            20                  25                  30

Ser Leu Ala Glu Ser Val Leu Lys Val Trp His Gly Ala Tyr Asn Ser
        35                  40                  45

Gly Leu Leu Pro Gln Leu Met Ala Gln His Ser Leu Ala Met Ala Gln
    50                  55                  60

Asn Gly Ala Val Pro Ser Glu Ala Thr Lys Arg Asp Gln Asn Leu Lys
65                  70                  75                  80

Arg Gly Asn Trp Gly Asn Gln Ile Glu Phe Val Leu Thr Ser Val Gly
                85                  90                  95

Tyr Ala Val Gly Leu Gly Asn Val Trp Arg Phe Pro Tyr Leu Cys Tyr
            100                 105                 110

Arg Asn Gly Gly Gly Ala Phe Met Phe Pro Tyr Phe Ile Met Leu Ile
        115                 120                 125

Phe Cys Gly Ile Pro Leu Phe Phe Met Glu Leu Ser Phe Gly Gln Phe
    130                 135                 140

Ala Ser Gln Gly Cys Leu Gly Val Trp Arg Ile Ser Pro Met Phe Lys
145                 150                 155                 160

Gly Val Gly Tyr Gly Met Met Val Val Ser Thr Tyr Ile Gly Ile Tyr
                165                 170                 175

Tyr Asn Val Val Ile Cys Ile Ala Phe Tyr Tyr Phe Phe Ser Ser Met
            180                 185                 190
```

-continued

```
Thr His Val Leu Pro Trp Ala Tyr Cys Asn Asn Pro Trp Asn Thr His
            195                 200                 205
Asp Cys Ala Gly Val Leu Asp Ala Ser Asn Leu Thr Asn Gly Ser Arg
            210                 215                 220
Pro Ala Ala Leu Pro Ser Asn Leu Ser His Leu Leu Asn His Ser Leu
225                 230                 235                 240
Gln Arg Thr Ser Pro Ser Glu Glu Tyr Trp Arg Leu Tyr Val Leu Lys
            245                 250                 255
Leu Ser Asp Asp Ile Gly Asn Phe Gly Glu Val Arg Leu Pro Leu Leu
            260                 265                 270
Gly Cys Leu Gly Val Ser Trp Leu Val Phe Leu Cys Leu Ile Arg
            275                 280                 285
Gly Val Lys Ser Ser Gly Lys Val Val Tyr Phe Thr Ala Thr Phe Pro
            290                 295                 300
Tyr Val Leu Thr Ile Leu Phe Val Arg Gly Val Thr Leu Glu Gly
305                 310                 315                 320
Ala Phe Asp Gly Ile Met Tyr Tyr Leu Thr Pro Gln Trp Asp Lys Ile
            325                 330                 335
Leu Glu Ala Lys Val Trp Gly Asp Ala Ala Ser Gln Ile Phe Tyr Ser
            340                 345                 350
Leu Ala Cys Ala Trp Gly Gly Leu Ile Thr Met Ala Ser Tyr Asn Lys
            355                 360                 365
Phe His Asn Asn Cys Tyr Arg Asp Ser Val Ile Ile Ser Ile Thr Asn
            370                 375                 380
Cys Ala Thr Ser Val Tyr Ala Gly Phe Val Ile Phe Ser Ile Leu Gly
385                 390                 395                 400
Phe Met Ala Asn His Leu Gly Val Asp Val Ser Arg Val Ala Asp His
            405                 410                 415
Gly Pro Gly Leu Ala Phe Val Ala Tyr Pro Glu Ala Leu Thr Leu Leu
            420                 425                 430
Pro Ile Ser Pro Leu Trp Ser Leu Leu Phe Phe Phe Met Leu Ile Leu
            435                 440                 445
Leu Gly Leu Gly Thr Gln Phe Cys Leu Leu Glu Thr Leu Gly Thr Ala
            450                 455                 460
Ile Val Asp Glu Val Gly Asn Glu Trp Ile Leu Gln Lys Lys Thr Asn
465                 470                 475                 480
Met Thr Leu Gly Arg Ala Val Ala Gly Phe Leu Leu Gly Ile Pro Leu
            485                 490                 495
Thr Ser Gln Ala Gly Ile Tyr Trp Leu Leu Leu Met Asp Asn Tyr Ala
            500                 505                 510
Ala Ser Phe Ser Leu Val Val Ile Ser Cys Ile Met Cys Val Ala Ile
            515                 520                 525
Met Tyr Ile Tyr Gly His Arg Asn Tyr Phe Gln Asp Ile Gln Met Met
            530                 535                 540
Leu Gly Phe Pro Pro Leu Phe Phe Gln Ile Cys Trp Arg Phe Val
545                 550                 555                 560
Ser Pro Ala Ile Ile Phe Phe Ile Leu Val Phe Thr Val Ile Gln Tyr
            565                 570                 575
Gln Pro Ile Thr Tyr Asn His Tyr Gln Tyr Pro Gly Trp Ala Val Ala
            580                 585                 590
Ile Gly Phe Leu Met Ala Leu Ser Ser Val Leu Cys Ile Pro Leu Tyr
            595                 600                 605
```

```
Ala Met Phe Arg Leu Cys Arg Thr Asp Gly Asp Thr Leu Leu Gln Arg
    610                 615                 620

Leu Lys Asn Ala Thr Lys Pro Ser Arg Asp Trp Gly Pro Ala Leu Leu
625                 630                 635                 640

Glu His Arg Thr Gly Arg Tyr Ala Pro Thr Ile Ala Pro Ser Pro Glu
                645                 650                 655

Asp Gly Phe Glu Val Gln Ser Leu His Pro Asp Lys Ala Gln Ile Pro
            660                 665                 670

Ile Val Gly Ser Asn Gly Ser Arg Arg Leu Gln Asp Ser Arg Ile
        675                 680                 685

<210> SEQ ID NO 24
<211> LENGTH: 638
<212> TYPE: PRT
<213> ORGANISM: Homo sapiens

<400> SEQUENCE: 24

Met Ala Ala Ala His Gly Pro Val Ala Pro Ser Ser Pro Glu Gln Asn
1               5                   10                  15

Gly Ala Val Pro Ser Glu Ala Thr Lys Arg Asp Gln Asn Leu Lys Arg
            20                  25                  30

Gly Asn Trp Gly Asn Gln Ile Glu Phe Val Leu Thr Ser Val Gly Tyr
        35                  40                  45

Ala Val Gly Leu Gly Asn Val Trp Arg Phe Pro Tyr Leu Cys Tyr Arg
    50                  55                  60

Asn Gly Gly Gly Ala Phe Met Phe Pro Tyr Phe Ile Met Leu Ile Phe
65                  70                  75                  80

Cys Gly Ile Pro Leu Phe Phe Met Glu Leu Ser Phe Gly Gln Phe Ala
                85                  90                  95

Ser Gln Gly Cys Leu Gly Val Trp Arg Ile Ser Pro Met Phe Lys Gly
            100                 105                 110

Val Gly Tyr Gly Met Met Val Val Ser Thr Tyr Ile Gly Ile Tyr Tyr
        115                 120                 125

Asn Val Val Ile Cys Ile Ala Phe Tyr Tyr Phe Phe Ser Ser Met Thr
    130                 135                 140

His Val Leu Pro Trp Ala Tyr Cys Asn Asn Pro Trp Asn Thr His Asp
145                 150                 155                 160

Cys Ala Gly Val Leu Asp Ala Ser Asn Leu Thr Asn Gly Ser Arg Pro
                165                 170                 175

Ala Ala Leu Pro Ser Asn Leu Ser His Leu Leu Asn His Ser Leu Gln
            180                 185                 190

Arg Thr Ser Pro Ser Glu Glu Tyr Trp Arg Leu Tyr Val Leu Lys Leu
        195                 200                 205

Ser Asp Asp Ile Gly Asn Phe Gly Glu Val Arg Leu Pro Leu Leu Gly
    210                 215                 220

Cys Leu Gly Val Ser Trp Leu Val Val Phe Leu Cys Leu Ile Arg Gly
225                 230                 235                 240

Val Lys Ser Ser Gly Lys Val Val Tyr Phe Thr Ala Thr Phe Pro Tyr
                245                 250                 255

Val Val Leu Thr Ile Leu Phe Val Arg Gly Val Thr Leu Glu Gly Ala
            260                 265                 270

Phe Asp Gly Ile Met Tyr Tyr Leu Thr Pro Gln Trp Asp Lys Ile Leu
        275                 280                 285

Glu Ala Lys Val Trp Gly Asp Ala Ala Ser Gln Ile Phe Tyr Ser Leu
    290                 295                 300
```

```
Ala Cys Ala Trp Gly Gly Leu Ile Thr Met Ala Ser Tyr Asn Lys Phe
305                 310                 315                 320

His Asn Asn Cys Tyr Arg Asp Ser Val Ile Ile Ser Ile Thr Asn Cys
                325                 330                 335

Ala Thr Ser Val Tyr Ala Gly Phe Val Ile Phe Ser Ile Leu Gly Phe
            340                 345                 350

Met Ala Asn His Leu Gly Val Asp Val Ser Arg Val Ala Asp His Gly
        355                 360                 365

Pro Gly Leu Ala Phe Val Ala Tyr Pro Glu Ala Leu Thr Leu Leu Pro
370                 375                 380

Ile Ser Pro Leu Trp Ser Leu Phe Phe Phe Met Leu Ile Leu Leu
385                 390                 395                 400

Gly Leu Gly Thr Gln Phe Cys Leu Leu Glu Thr Leu Val Thr Ala Ile
                405                 410                 415

Val Asp Glu Val Gly Asn Glu Trp Ile Leu Gln Lys Lys Thr Tyr Val
            420                 425                 430

Thr Leu Gly Val Ala Val Ala Gly Phe Leu Leu Gly Ile Pro Leu Thr
        435                 440                 445

Ser Gln Ala Gly Ile Tyr Trp Leu Leu Leu Met Asp Asn Tyr Ala Ala
    450                 455                 460

Ser Phe Ser Leu Val Val Ile Ser Cys Ile Met Cys Val Ala Ile Met
465                 470                 475                 480

Tyr Ile Tyr Gly His Arg Asn Tyr Phe Gln Asp Ile Gln Met Met Leu
                485                 490                 495

Gly Phe Pro Pro Pro Leu Phe Phe Gln Ile Cys Trp Arg Phe Val Ser
            500                 505                 510

Pro Ala Ile Ile Phe Phe Ile Leu Val Phe Thr Val Ile Gln Tyr Gln
        515                 520                 525

Pro Ile Thr Tyr Asn His Tyr Gln Tyr Pro Gly Trp Ala Val Ala Ile
    530                 535                 540

Gly Phe Leu Met Ala Leu Ser Ser Val Leu Cys Ile Pro Leu Tyr Ala
545                 550                 555                 560

Met Phe Arg Leu Cys Arg Thr Asp Gly Asp Thr Leu Leu Gln Arg Leu
                565                 570                 575

Lys Asn Ala Thr Lys Pro Ser Arg Asp Trp Gly Pro Ala Leu Leu Glu
            580                 585                 590

His Arg Thr Gly Arg Tyr Ala Pro Thr Ile Ala Pro Ser Pro Glu Asp
        595                 600                 605

Gly Phe Glu Val Gln Ser Leu His Pro Asp Lys Ala Gln Ile Pro Ile
610                 615                 620

Val Gly Ser Asn Gly Ser Ser Arg Leu Gln Asp Ser Arg Ile
625                 630                 635

<210> SEQ ID NO 25
<211> LENGTH: 692
<212> TYPE: PRT
<213> ORGANISM: Homo sapiens

<400> SEQUENCE: 25

Met Ala Ala Ala His Gly Pro Val Ala Pro Ser Ser Pro Glu Gln Val
1               5                   10                  15

Thr Leu Leu Pro Val Gln Arg Ser Phe Phe Leu Pro Pro Phe Ser Gly
            20                  25                  30

Ala Thr Pro Ser Thr Ser Leu Ala Glu Ser Val Leu Lys Val Trp His
```

-continued

```
                35                  40                  45
Gly Ala Tyr Asn Ser Gly Leu Leu Pro Gln Leu Met Ala Gln His Ser
 50                  55                  60
Leu Ala Met Ala Gln Asn Gly Ala Val Pro Ser Glu Ala Thr Lys Arg
 65                  70                  75                  80
Asp Gln Asn Leu Lys Arg Gly Asn Trp Gly Asn Gln Ile Glu Phe Val
                 85                  90                  95
Leu Thr Ser Val Gly Tyr Ala Val Gly Leu Gly Asn Val Trp Arg Phe
                100                 105                 110
Pro Tyr Leu Cys Tyr Arg Asn Gly Gly Ala Phe Met Phe Pro Tyr
                115                 120                 125
Phe Ile Met Leu Ile Phe Cys Gly Ile Pro Leu Phe Phe Met Glu Leu
130                 135                 140
Ser Phe Gly Gln Phe Ala Ser Gln Gly Cys Leu Gly Val Trp Arg Ile
145                 150                 155                 160
Ser Pro Met Phe Lys Gly Val Gly Tyr Gly Met Met Val Val Ser Thr
                165                 170                 175
Tyr Ile Gly Ile Tyr Tyr Asn Val Val Ile Cys Ile Ala Phe Tyr Tyr
                180                 185                 190
Phe Phe Ser Ser Met Thr His Val Leu Pro Trp Ala Tyr Cys Asn Asn
                195                 200                 205
Pro Trp Asn Thr His Asp Cys Ala Gly Val Leu Asp Ala Ser Asn Leu
210                 215                 220
Thr Asn Gly Ser Arg Pro Ala Ala Leu Pro Ser Asn Leu Ser His Leu
225                 230                 235                 240
Leu Asn His Ser Leu Gln Arg Thr Ser Pro Ser Glu Glu Tyr Trp Arg
                245                 250                 255
Leu Tyr Val Leu Lys Leu Ser Asp Asp Ile Gly Asn Phe Gly Glu Val
                260                 265                 270
Arg Leu Pro Leu Leu Gly Cys Leu Gly Val Ser Trp Leu Val Val Phe
                275                 280                 285
Leu Cys Leu Ile Arg Gly Val Lys Ser Ser Gly Lys Val Val Tyr Phe
290                 295                 300
Thr Ala Thr Phe Pro Tyr Val Val Leu Thr Ile Leu Phe Val Arg Gly
305                 310                 315                 320
Val Thr Leu Glu Gly Ala Phe Asp Gly Ile Met Tyr Tyr Leu Thr Pro
                325                 330                 335
Gln Trp Asp Lys Ile Leu Glu Ala Lys Val Trp Gly Asp Ala Ala Ser
                340                 345                 350
Gln Ile Phe Tyr Ser Leu Ala Cys Ala Trp Gly Gly Leu Ile Thr Met
                355                 360                 365
Ala Ser Tyr Asn Lys Phe His Asn Asn Cys Tyr Arg Asp Ser Val Ile
370                 375                 380
Ile Ser Ile Thr Asn Cys Ala Thr Ser Val Tyr Ala Gly Phe Val Ile
385                 390                 395                 400
Phe Ser Ile Leu Gly Phe Met Ala Asn His Leu Gly Val Asp Val Ser
                405                 410                 415
Arg Val Ala Asp His Gly Pro Gly Leu Ala Phe Val Ala Tyr Pro Glu
                420                 425                 430
Ala Leu Thr Leu Leu Pro Ile Ser Pro Leu Trp Ser Leu Leu Phe Phe
                435                 440                 445
Phe Met Leu Ile Leu Leu Gly Leu Gly Thr Gln Phe Cys Leu Leu Glu
450                 455                 460
```

```
Thr Leu Val Thr Ala Ile Val Asp Glu Val Gly Asn Glu Trp Ile Leu
465                 470                 475                 480

Gln Lys Lys Thr Tyr Val Thr Leu Gly Val Ala Val Ala Gly Phe Leu
                485                 490                 495

Leu Gly Ile Pro Leu Thr Ser Gln Ala Gly Ile Tyr Trp Leu Leu Leu
            500                 505                 510

Met Asp Asn Tyr Ala Ala Ser Phe Ser Leu Val Val Ile Ser Cys Ile
            515                 520                 525

Met Cys Val Ala Ile Met Tyr Ile Tyr Gly His Arg Asn Tyr Phe Gln
        530                 535                 540

Asp Ile Gln Met Met Leu Gly Phe Pro Pro Leu Phe Phe Gln Ile
545                 550                 555                 560

Cys Trp Arg Phe Val Ser Pro Ala Ile Ile Phe Phe Ile Leu Val Phe
                565                 570                 575

Thr Val Ile Gln Tyr Gln Pro Ile Thr Tyr Asn His Tyr Gln Tyr Pro
            580                 585                 590

Gly Trp Ala Val Ala Ile Gly Phe Leu Met Ala Leu Ser Ser Val Leu
        595                 600                 605

Cys Ile Pro Leu Tyr Ala Met Phe Arg Leu Cys Arg Thr Asp Gly Asp
610                 615                 620

Thr Leu Leu Gln Arg Leu Lys Asn Ala Thr Lys Pro Ser Arg Asp Trp
625                 630                 635                 640

Gly Pro Ala Leu Leu Glu His Arg Thr Gly Arg Tyr Ala Pro Thr Ile
                645                 650                 655

Ala Pro Ser Pro Glu Asp Gly Phe Glu Val Gln Ser Leu His Pro Asp
                660                 665                 670

Lys Ala Gln Ile Pro Ile Val Gly Ser Asn Gly Ser Ser Arg Leu Gln
            675                 680                 685

Asp Ser Arg Ile
    690

<210> SEQ ID NO 26
<211> LENGTH: 184
<212> TYPE: PRT
<213> ORGANISM: Homo sapiens

<400> SEQUENCE: 26

Met Ala Ala Ala His Gly Pro Val Ala Pro Ser Ser Pro Glu Gln Gly
1               5                   10                  15

Pro Gly Gln Val Pro Ala Trp Ala Gly Ser Arg Cys Val Leu Ile Pro
            20                  25                  30

Gly Arg Arg Gly Arg Val Glu Met Ser Xaa Asp Gly Xaa Glu Glu Trp
        35                  40                  45

Cys Cys Ala Gln Arg Gly His Gln Glu Gly Pro Glu Pro Gln Thr Gly
    50                  55                  60

Gln Leu Gly Gln Pro Asp Arg Val Cys Thr Asp Glu Arg Gly Leu Cys
65                  70                  75                  80

Arg Gly Pro Gly Gln Cys Leu Ala Leu Pro Ile Pro Leu Leu Ser Gln
                85                  90                  95

Arg Gly Arg Arg Leu His Val Pro Leu Leu His Ala His Leu Leu
            100                 105                 110

Arg Asp Pro Pro Leu Leu His Gly Ala Leu Leu Arg Pro Val Cys Lys
        115                 120                 125

Pro Gly Val Pro Gly Gly Leu Glu Asp Gln Pro His Val Gln Arg Ser
```

```
                130                 135                 140
Gly Leu Trp Tyr Asp Gly Gly Val His Leu His Arg His Leu Leu Gln
145                 150                 155                 160

Cys Gly His Leu His Arg Leu Leu Leu Leu Leu Val His Asp Ala
                165                 170                 175

Arg Ala Ala Leu Gly Leu Leu Gln
            180

<210> SEQ ID NO 27
<211> LENGTH: 125
<212> TYPE: PRT
<213> ORGANISM: Homo sapiens

<400> SEQUENCE: 27

Met Ala Ala Ala His Gly Pro Val Ala Pro Ser Ser Pro Glu Gln Asn
1               5                   10                  15

Gly Ala Val Pro Ser Glu Ala Thr Lys Arg Asp Gln Asn Leu Lys Arg
            20                  25                  30

Gly Asn Trp Gly Asn Gln Ile Glu Arg Leu His Val Pro Leu Leu His
        35                  40                  45

His Ala His Leu Leu Arg Asp Pro Pro Leu Leu His Gly Ala Leu Leu
    50                  55                  60

Arg Pro Val Cys Lys Pro Gly Val Pro Gly Leu Glu Asp Gln Pro
65                  70                  75                  80

His Val Gln Arg Ser Gly Leu Trp Tyr Asp Gly Gly Val His Leu His
                85                  90                  95

Arg His Leu Leu Gln Cys Gly His Leu His Arg Leu Leu Leu Leu
            100                 105                 110

Leu Val His Asp Ala Arg Ala Ala Leu Gly Leu Leu Gln
        115                 120                 125

<210> SEQ ID NO 28
<211> LENGTH: 64
<212> TYPE: PRT
<213> ORGANISM: Homo sapiens

<400> SEQUENCE: 28

Met Ala Ala Ala His Gly Pro Val Ala Pro Ser Ser Pro Glu Gln Ala
1               5                   10                  15

Pro Ser Cys Ser Pro Thr Ser Ser Cys Ser Ser Ser Ala Gly Ser Pro
            20                  25                  30

Ser Ser Ser Trp Ser Pro Ser Ala Ser Leu Gln Ala Arg Gly Ala
        35                  40                  45

Trp Gly Ser Gly Gly Ser Ala Pro Cys Ser Lys Glu Trp Ala Met Val
    50                  55                  60

<210> SEQ ID NO 29
<211> LENGTH: 229
<212> TYPE: PRT
<213> ORGANISM: Homo sapiens

<400> SEQUENCE: 29

Met Ala Ala Ala His Gly Pro Val Ala Pro Ser Ser Pro Glu Gln Asn
1               5                   10                  15

Gly Ala Val Pro Ser Glu Ala Thr Lys Arg Asp Gln Asn Leu Lys Arg
            20                  25                  30

Gly Asn Trp Gly Asn Gln Ile Glu Phe Val Leu Thr Ser Val Gly Tyr
        35                  40                  45
```

Ala Val Gly Leu Gly Asn Val Trp Arg Phe Pro Tyr Leu Cys Tyr Arg
    50                  55                  60

Asn Gly Gly Gly Ala Phe Met Phe Pro Tyr Phe Ile Met Leu Ile Phe
65                  70                  75                  80

Cys Gly Ile Pro Leu Phe Phe Met Glu Leu Ser Phe Gly Gln Phe Ala
                85                  90                  95

Ser Gln Gly Cys Leu Gly Val Trp Arg Ile Ser Pro Met Phe Lys Gly
            100                 105                 110

Val Gly Tyr Gly Met Met Val Val Ser Thr Tyr Ile Gly Ile Tyr Tyr
        115                 120                 125

Asn Val Val Ile Cys Ile Ala Phe Tyr Tyr Phe Phe Ser Ser Met Thr
    130                 135                 140

His Val Leu Pro Trp Ala Tyr Cys Asn Asn Pro Trp Asn Thr His Asp
145                 150                 155                 160

Cys Ala Gly Val Leu Asp Ala Ser Asn Leu Thr Asn Gly Ser Arg Pro
                165                 170                 175

Ala Ala Leu Pro Ser Asn Leu Ser His Leu Leu Asn His Ser Leu Gln
            180                 185                 190

Arg Thr Ser Pro Ser Glu Glu Tyr Trp Arg Ile Ser Leu Cys Cys Pro
        195                 200                 205

Gly Trp Ser Ala Val Ala Arg Ser Gln Leu Thr Ala Thr Ser Ala Ser
    210                 215                 220

Arg Gly Cys Thr Cys
225

<210> SEQ ID NO 30
<211> LENGTH: 94
<212> TYPE: PRT
<213> ORGANISM: Homo sapiens

<400> SEQUENCE: 30

Met Ala Ala Ala His Gly Pro Val Ala Pro Ser Ser Pro Glu Gln Gly
1               5                   10                  15

Pro Gly Gln Val Pro Ala Trp Ala Gly Ser Arg Cys Val Leu Ile Pro
            20                  25                  30

Gly Arg Arg Gly Arg Val Glu Met Ser Ala Asp Gly Ser Glu Gly Glu
        35                  40                  45

Glu Thr Arg Lys Leu His Phe Ser Pro Val Gly His Pro Asp Leu Thr
    50                  55                  60

Phe Lys Arg Met Val Leu Cys Pro Ala Arg Pro Pro Arg Gly Thr Arg
65                  70                  75                  80

Thr Ser Asn Gly Ala Thr Gly Ala Thr Arg Ser Ser Leu Tyr
                85                  90

<210> SEQ ID NO 31
<211> LENGTH: 456
<212> TYPE: PRT
<213> ORGANISM: Homo sapiens

<400> SEQUENCE: 31

Met Ala Ala Ala His Gly Pro Val Ala Pro Ser Ser Pro Glu Gln Asn
1               5                   10                  15

Gly Ala Val Pro Ser Glu Ala Thr Lys Arg Asp Gln Asn Leu Lys Arg
            20                  25                  30

Gly Asn Trp Gly Asn Gln Ile Glu Phe Val Leu Thr Ser Val Gly Tyr
        35                  40                  45

-continued

```
Ala Val Gly Leu Gly Asn Val Trp Arg Phe Pro Tyr Leu Cys Tyr Arg
         50                  55                  60
Asn Gly Gly Gly Ala Phe Met Phe Pro Tyr Phe Ile Met Leu Ile Phe
 65                  70                  75                  80
Cys Gly Ile Pro Leu Phe Phe Met Glu Leu Ser Phe Gly Gln Phe Ala
                 85                  90                  95
Ser Gln Gly Cys Leu Gly Val Trp Arg Ile Ser Pro Met Phe Lys Gly
             100                 105                 110
Val Gly Tyr Gly Met Met Val Val Ser Thr Tyr Ile Gly Ile Tyr Tyr
             115                 120                 125
Asn Val Val Ile Cys Ile Ala Phe Tyr Tyr Phe Phe Ser Ser Met Thr
         130                 135                 140
His Val Leu Pro Trp Ala Tyr Cys Asn Asn Pro Trp Asn Thr His Asp
145                 150                 155                 160
Cys Ala Gly Val Leu Asp Ala Ser Asn Leu Thr Asn Gly Ser Arg Pro
                 165                 170                 175
Ala Ala Leu Pro Ser Asn Leu Ser His Leu Leu Asn His Ser Leu Gln
             180                 185                 190
Arg Thr Ser Pro Ser Glu Glu Tyr Trp Arg Leu Tyr Val Leu Lys Leu
         195                 200                 205
Ser Asp Asp Ile Gly Asn Phe Gly Glu Val Arg Leu Pro Leu Leu Gly
210                 215                 220
Cys Leu Gly Val Ser Trp Leu Val Val Phe Leu Cys Leu Ile Arg Gly
225                 230                 235                 240
Val Lys Ser Ser Gly Lys Val Val Tyr Phe Thr Ala Thr Phe Pro Tyr
                 245                 250                 255
Val Val Leu Thr Ile Leu Phe Val Arg Gly Val Thr Leu Glu Gly Ala
             260                 265                 270
Phe Asp Gly Ile Met Tyr Tyr Leu Thr Pro Gln Trp Asp Lys Ile Leu
         275                 280                 285
Glu Ala Lys Val Trp Gly Asp Ala Ala Ser Gln Ile Phe Tyr Ser Leu
290                 295                 300
Gly Cys Ala Trp Gly Gly Leu Ile Thr Met Ala Ser Tyr Asn Lys Phe
305                 310                 315                 320
His Asn Asn Cys Tyr Arg Asp Ser Val Ile Ile Ser Ile Thr Asn Cys
                 325                 330                 335
Ala Thr Ser Val Tyr Ala Gly Phe Val Ile Phe Ser Ile Leu Gly Phe
             340                 345                 350
Met Ala Asn His Leu Gly Val Asp Val Ser Arg Val Ala Asp His Gly
         355                 360                 365
Pro Gly Leu Ala Phe Val Ala Tyr Pro Glu Ala Leu Thr Leu Leu Pro
370                 375                 380
Ile Ser Pro Leu Trp Ser Leu Leu Phe Phe Met Leu Ile Leu Leu Leu
385                 390                 395                 400
Gly Leu Gly Thr Gln Phe Cys Leu Leu Glu Thr Leu Val Thr Ala Ile
                 405                 410                 415
Val Asp Glu Val Gly Asn Glu Trp Ile Leu Gln Lys Lys Thr Tyr Val
             420                 425                 430
Thr Leu Gly Val Ala Val Ala Gly Phe Leu Leu Gly Ile Pro Leu Thr
         435                 440                 445
Ser Gln Ala Ser Ile Gly Cys Cys
450                 455
```

<210> SEQ ID NO 32
<211> LENGTH: 550
<212> TYPE: PRT
<213> ORGANISM: Homo sapiens

<400> SEQUENCE: 32

```
Met Ala Ala His Gly Pro Val Ala Ser Ser Pro Glu Gln Asn
1               5                   10                  15

Gly Ala Val Pro Ser Glu Ala Thr Lys Arg Asp Gln Asn Leu Lys Arg
            20                  25                  30

Gly Asn Trp Gly Asn Gln Ile Glu Phe Val Leu Thr Ser Val Gly Tyr
        35                  40                  45

Ala Val Gly Leu Gly Asn Val Trp Arg Phe Pro Tyr Leu Cys Tyr Arg
    50                  55                  60

Asn Gly Gly Gly Ala Phe Met Phe Pro Tyr Phe Ile Met Leu Ile Phe
65                  70                  75                  80

Cys Gly Ile Pro Leu Phe Phe Met Glu Leu Ser Phe Gly Gln Phe Ala
                85                  90                  95

Ser Gln Gly Cys Leu Gly Val Trp Arg Ile Ser Pro Met Phe Lys Gly
            100                 105                 110

Val Gly Tyr Gly Met Met Val Val Ser Thr Tyr Ile Gly Ile Tyr Tyr
        115                 120                 125

Asn Val Val Ile Cys Ile Ala Phe Tyr Tyr Phe Phe Ser Ser Met Thr
130                 135                 140

His Val Leu Pro Trp Ala Tyr Cys Asn Asn Pro Trp Asn Thr His Asp
145                 150                 155                 160

Cys Ala Gly Val Leu Asp Ala Ser Asn Leu Thr Asn Gly Ser Arg Pro
                165                 170                 175

Ala Ala Leu Pro Ser Asn Leu Ser His Leu Leu Asn His Ser Leu Gln
            180                 185                 190

Arg Thr Ser Pro Ser Glu Glu Tyr Trp Arg Leu Tyr Val Leu Lys Leu
        195                 200                 205

Ser Asp Asp Ile Gly Asn Phe Gly Glu Val Arg Leu Pro Leu Leu Gly
    210                 215                 220

Cys Leu Gly Val Ser Trp Leu Val Val Phe Leu Cys Leu Ile Arg Gly
225                 230                 235                 240

Val Lys Ser Ser Gly Lys Val Val Tyr Phe Thr Ala Thr Phe Pro Tyr
                245                 250                 255

Val Val Leu Thr Ile Leu Phe Val Arg Gly Val Thr Leu Glu Gly Ala
            260                 265                 270

Phe Asp Gly Ile Met Tyr Tyr Leu Thr Pro Gln Trp Asp Lys Ile Leu
        275                 280                 285

Glu Ala Lys Val Trp Gly Asp Ala Ala Ser Gln Ile Phe Tyr Ser Leu
    290                 295                 300

Gly Cys Ala Trp Gly Gly Leu Ile Thr Met Ala Ser Tyr Asn Lys Phe
305                 310                 315                 320

His Asn Asn Cys Tyr Arg Asp Ser Val Ile Ile Ser Ile Thr Asn Cys
                325                 330                 335

Ala Thr Ser Val Tyr Ala Gly Phe Val Ile Phe Ser Ile Leu Gly Phe
            340                 345                 350

Met Ala Asn His Leu Gly Val Asp Val Ser Arg Val Ala Asp His Gly
        355                 360                 365

Pro Gly Leu Ala Phe Val Ala Tyr Pro Glu Ala Leu Thr Leu Leu Pro
    370                 375                 380
```

```
Ile Ser Pro Leu Trp Ser Leu Leu Phe Phe Met Leu Ile Leu Leu
385                 390                 395                 400

Gly Leu Gly Thr Gln Phe Cys Leu Leu Glu Thr Leu Val Thr Ala Ile
            405                 410                 415

Val Asp Glu Val Gly Asn Glu Trp Ile Leu Gln Lys Lys Thr Tyr Val
        420                 425                 430

Thr Leu Gly Val Ala Val Ala Gly Phe Leu Leu Gly Ile Pro Leu Thr
            435                 440                 445

Ser Gln Ala Gly Ile Tyr Trp Leu Leu Leu Met Asp Asn Tyr Ala Ala
        450                 455                 460

Ser Phe Ser Leu Val Val Ile Ser Cys Ile Met Cys Val Ala Ile Met
465                 470                 475                 480

Tyr Ile Tyr Gly His Arg Asn Tyr Phe Gln Asp Ile Gln Met Met Leu
            485                 490                 495

Gly Phe Pro Pro Leu Phe Phe Gln Ile Cys Trp Arg Phe Val Ser
                500                 505                 510

Pro Ala Ile Ile Phe Ser Leu Pro Thr His Arg Ala Pro Ala Pro Gly
            515                 520                 525

Pro Ala Cys Phe Phe His Gly Pro Asp Val Asp Ser Cys Pro Cys Ser
        530                 535                 540

Ala Pro Asn Ala Leu Phe
545                 550

<210> SEQ ID NO 33
<211> LENGTH: 188
<212> TYPE: PRT
<213> ORGANISM: Homo sapiens

<400> SEQUENCE: 33

Met Ala Ala Ala His Gly Pro Val Ala Pro Ser Ser Pro Glu Gln Asn
1               5                   10                  15

Ile Phe Gln Gly Pro Gly Gln Val Pro Ala Trp Ala Gly Ser Arg Cys
            20                  25                  30

Val Leu Ile Pro Gly Arg Arg Gly Arg Val Glu Met Ser Ala Asp Asp
        35                  40                  45

Ser Glu Glu Trp Cys Cys Ala Gln Arg Gly His Gln Glu Gly Pro Glu
    50                  55                  60

Pro Gln Thr Gly Gln Leu Gly Gln Pro Asp Arg Val Cys Thr Asp Glu
65              70                  75                  80

Arg Gly Leu Cys Arg Gly Pro Gly Gln Cys Leu Ala Leu Pro Ile Pro
            85                  90                  95

Leu Leu Ser Gln Arg Gly Arg Leu His Val Pro Leu Leu His His
            100                 105                 110

Ala His Leu Leu Arg Asp Pro Pro Leu Leu His Gly Ala Leu Leu Arg
        115                 120                 125

Pro Val Cys Lys Pro Gly Val Pro Gly Gly Leu Glu Asp Gln Pro His
        130                 135                 140

Val Gln Arg Ser Gly Leu Trp Tyr Asp Gly Gly Val His Leu His Arg
145                 150                 155                 160

His Leu Leu Gln Cys Gly His Leu His Arg Leu Leu Leu Leu Leu
                165                 170                 175

Val His Asp Ala Arg Ala Ala Leu Gly Leu Leu Gln
            180                 185
```

```
<210> SEQ ID NO 34
<211> LENGTH: 22
<212> TYPE: DNA
<213> ORGANISM: Artificial Sequence
<220> FEATURE:
<223> OTHER INFORMATION: oligonucleotide SLC6A9LF

<400> SEQUENCE: 34
gtgctgggct gcatggggac tg                                              22

<210> SEQ ID NO 35
<211> LENGTH: 23
<212> TYPE: DNA
<213> ORGANISM: Artificial Sequence
<220> FEATURE:
<223> OTHER INFORMATION: oligonucleotide SLC6A9LR

<400> SEQUENCE: 35
cacagtctct cgtggagcac ggg                                             23

<210> SEQ ID NO 36
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 36
tgtaaaacga cggccagt                                                   18

<210> SEQ ID NO 37
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 37
caggaaacag ctatgacc                                                   18
```